US007718614B2

(12) United States Patent
Itoh et al.

(10) Patent No.: US 7,718,614 B2
(45) Date of Patent: May 18, 2010

(54) COMBINATION THERAPY OF PEPTIDE VACCINATION AND ESTRAMUSTINE TREATMENT

(75) Inventors: Kyogo Itoh, Miyaki-gun (JP); Masanori Noguchi, Kurume (JP)

(73) Assignee: Kurume University, Fukuoka (JP)

( * ) Notice: Subject to any disclaimer, the term of this patent is extended or adjusted under 35 U.S.C. 154(b) by 68 days.

(21) Appl. No.: 11/412,874

(22) Filed: Apr. 28, 2006

(65) Prior Publication Data
US 2007/0048336 A1    Mar. 1, 2007

Related U.S. Application Data

(63) Continuation-in-part of application No. PCT/JP2004/016497, filed on Oct. 29, 2004, and a continuation-in-part of application No. PCT/JP03/14010, filed on Oct. 31, 2003.

(51) Int. Cl.
    *A61K 38/00*    (2006.01)
(52) U.S. Cl. .............................. 514/12; 514/13; 514/14; 514/15; 514/16; 514/17
(58) Field of Classification Search ........................ None
     See application file for complete search history.

(56) References Cited

U.S. PATENT DOCUMENTS 6,143,864 A * 11/2000 DeFeo-Jones et al. ....... 530/322

OTHER PUBLICATIONS

Verma et al. (Nature 1997, 389: 239-242).*
Amalfitano et al. (Current Gene Therapy 2002, 2: 111-133).*
The Department of Health and Human Services has released a memorandum dated Jan. 14, 2003.*
Pandha et al. (Current Opinion in Investigational Drugs 2000; 1 (1): 122-134).*
Burgess et al, Journal of Cell Biology vol. 111 Nov. 1990 2129-2138.*
Lazar et al Molecular and Cellular Biology Mar. 1988 vol. 8 No. 3 1247-1252.*
A. B. H. Bakker et al., "Melanocyte Lineage-Specific Antigen gp100 is Recognized by Melanoma-Derived Tumor-infiltrating Lymphocytes", The Journal of Experimental Medicine, vol. 179, pp. 1005-1009, Mar. 1994.
Y. Kawakami et al., "Cloning of the Gene Coding for a Shared Human Melanoma Antigen Recognized by Autologous T Cells Infiltrating into Tumor", Proc. Natl. Acad. Sci., vol. 91, pp. 3315-3519, Apr. 1994.
V. Brichard et al., "The Tyrosinase Gene Codes for an Antigen Recognized by Autologous Cytolytic T Lymphocytes on HLA-A2 Melanomas", J. Exp. Med., vol. 178, pp. 489-495, Aug. 1993.
B. Gaugler et al., "Human Gene MAGE-3 Codes for an Antigen Recognized on a Melanoma by Autologous Cytolytic T Lymphocytes", J. Exp. Med., vol. 179, pp. 921-930, Mar. 1994.
P. F. Robbins et al., "A Mutated β-Catenin Gene Encodes a Melanoma-Specific Antigen Recognized by Tumor Infiltrating Lymphocytes", J. Exp. Med., vol. 183, pp. 1185-1192, Mar. 1996.
T. Wolfel et al., "A $p16^{INK4a}$-Insensitive CDK4 Mutant Targeted by Cytolytic T Lymphocytes in a Human Melanoma", Science, vol. 269, pp. 1281-1285, Sep. 1, 1995.
B. Fisk et al., "Identification of an Immunodominant Peptide of HER-2/neu Protooncogene Recognized by Ovarian Tumor-Specific Cytotoxic T Lymphocyte Lines", J. Exp. Med., vol. 181, pp. 2109-2117, Jun. 1995.
M. Ropke et al., "Spontaneous Human Squamous Cell Carcinomas are Killed by a Human Cytotoxic T Lymphocyte Clone Recognizing a Wild-Type p53-Derived Peptide", Proc. Natl. Acad. Sci., vol. 93, pp. 14704-14707, Dec. 1996.
K. Y. Tsang et al., "Generation of Human Cytotoxic T Cells Specific for Human Carcinoembryonic Antigen Epitopès from Patients Immunized with Recombinant Vaccinia-CEA Vaccine", Journal of National Cancer Institute, vol. 87, No. 13, pp. 982-990, Jul. 5, 1995.
P. Correale et al., "In Vitro Generation of Human Cytotoxic T Lymphocytes Specific for Peptides Derived from Prostate-Specific Antigen", Journal of the National Cancer Institute, vol. 89, No. 4, pp. 293-300, Feb. 19, 1997.
M. E. Ressing et al., "Human CTL Epitopes Encoded by Human Papillomavirus Type 16 E6 and E7 Identified Through In Vivo and in Vitro Immunogenicity Studies of HLA-A*0201-Binding Peptides[1]", The Journal of Immunology, vol. 154, pp. 5934-5943, 1995.
G. Stuber et al., "HLA-A0201 and HLA-B7 Binding Peptides in the EBV-Encoded EBNA-1, EBNA-2 and BZLF-1 Proteins Detected in the MHC Class I Stabilization Assay. Low Proportion of Binding Motifs for Several HLA Class I Alleles in EBNA-1", International Immunology, vol. 7, No. 4, pp. 653-663, 1995.
T. Boon et al., "Tumor Antigens Recognized by T Cells", Immunology Today, vol. 18, No. 6, pp. 267-268, Jun. 1997.
T. Boon et al., "Human Tumor Antigens Recognized by T Lymphocytes", J. Exp. Med., vol. 183, pp. 725-729, Mar. 1996.
P. F. Robbins et al., "Human Tumor Antigens Recognized by T Cells", Current Opinion in Immunology, vol. 8, pp. 628-636, 1996.
M. Ito et al., "Molecular Basis of T Cell-Mediated Recognition of Pancreatic Cancer Cells[1]", Cancer Research, vol. 61, pp. 2038-2046, Mar. 1, 2001.
I. F. Tannock et al., "Chemotherapy with Mitoxantrone Plus Prednisone or Prednisone Alone for Symptomatic Hormone-Resistant Prostate Cancer: A Canadian Randomized Trial with Palliative End Points", Journal of Clinical Oncology, vol. 14, No. 6, pp. 1756-1764, Jun. 1996.
P. W. Kantoff et al., "Hydrocortisone with or without Mitoxantrone in Men with Hormone-Refractory Prostate Cancer: Results of the Cancer and Leukemia Group B 9182 Study", Journal of Clinical Oncology, vol. 17, No. 8, pp. 2506-2513, Aug. 1999.
G. Hudes et al., "Vinblastine Versus Vinblastine Plus Oral Estramustine Phosphate for Patients with Hormone-Refractory Prostate Cancer: A Hoosier Oncology Group and Fox Chase Network Phase III Trial", Journal of Clinical Oncology, vol. 17, No. 10, pp. 3160-3166, Oct. 1999.

(Continued)

*Primary Examiner*—Sheela J Huff
(74) *Attorney, Agent, or Firm*—Wenderoth, Lind & Ponack, L.L.P.

(57) ABSTRACT

A method for treating a prostate cancer, which comprises administering a therapeutically effective amount of a cancer antigen peptide-associated agent and a lower dose of an estramustine or a salt thereof to a patient in need thereof, and a pharmaceutical composition thereof are provided.

4 Claims, 40 Drawing Sheets

OTHER PUBLICATIONS

D. C. Smith et al., "Phase II Trial of Oral Estramustine, Oral Etoposide, and Intravenous Paclitaxel in Hormone-Refractory Prostate Cancer", Journal of Clinical Oncology, vol. 17, No. 6, pp. 1664-1671, Jun. 1999.

T. M. Beer et al., "Phase II Study of Weekly Docetaxel in Symptomatic Androgen-Independent Prostate Cancer", Annals of Oncology, vol. 12, pp. 1273-1279, 2001.

G. R. Hudes et al., Phase II Trial of 96-Hour Paclitaxel Plus Oral Estramustine Phosphate in Metastatic Hormone-refractory Prostate Cancer, Journal of Clinical Oncology, vol. 15, No. 9, pp. 3156-3163, Sep. 1997.

J. A. Ellerhorst et al., "Phase II Trial of Alternating Weekly Chemohormonal Therapy for Patients with Androgen-Independent Prostate Cancer[1]", Clinical Cancer Research, vol. 3, pp. 2371-2376, Dec. 1997.

W. K. Kelly et al., "Paclitaxel, Estramustine Phosphate, and Carboplatin in Patients with Advanced Prostate Cancer", Journal of Clinical Oncology, vol. 19, No. 1, pp. 44-53, Jan. 1, 2001.

P. Van Der Bruggen et al., "A Gene Encoding an Antigen Recognized by Cytolytic T Lymphocytes on a Human Melanoma", Science, vol. 254, pp. 1643-1647, Dec. 1991.

Y. Kawakami et al., "Identification of the Immunodominant Peptides of the MART-1 Human Melanoma Antigen Recognized by the Majority of HLA-A2-Restricted Tumor Infiltrating Lymphocytes", The Journal of Experimental Medicine, vol. 180, pp. 347-352, Jul. 1994.

B. A. Tjoa et al., "Evaluation of Phase I/II Clinical Trials in Prostate Cancer with Dendritic Cells and PSMA Peptides", The Prostate, vol. 36, pp. 39-44, 1998.

M. L. Salgaller et al., "Report of Immune Monitoring of Prostate Cancer Patients Undergoing T-Cell Therapy using Dendritic Cells Pulsed with HLA-A2-Specific Peptides from Prostate-Specific Membrane Antigen (PSMA)", The Prostate, vol. 35, No. 144-151, 1998.

t. Mine et al., "Immunological Evaluation of CTL Precursor-Oriented Vaccines for Advanced Lung Cancer Patients", Cancer Science, vol. 94, No. 6, pp. 548-556, Jun. 2003.

S. Tanaka et al., "Peptide Vaccination for Patients with Melanoma and Other Types of Cancer Based on PreExisting Peptide-Specific Cytotoxic T-Lymphocyte Precursors in the Periphery", Journal of Immunotherapy, vol. 26, No. 4, pp. 357-366, Jul./Aug. 2003.

M. Noguchi et al., "Induction of Cellular and Humoral Immune Responses to Tumor Cells and Peptides in HLA-A24 Positive Hormone-Refractory Prostate Cancer Patients by Peptide Vaccination", The Prostate, vol. 57, pp. 80-92, 2003.

C. M. Perry et al., "Estramustine Phosphate Sodium", Drug & Aging, vol. 7, No. 1, pp. 49-74, 1995.

S. Shichijo et al., "A Gene Encoding Antigenic Peptides of Human Squamous Cell Carcinoma Recognized by Cytotoxic T Lymphocytes", J. Exp. Med., vol. 187, No. 3, pp. 277-288, Feb. 2, 1998.

M. Nakao et al., "Identification of a Gene Coding for a New Squamous Cell Carcinoma Antigen Recognized by the CTL[1]", The Journal of Immunology, vol. 164, pp. 2565-2574, 2000.

D. Yang et al., "Identification of a Gene Coding for a Protein Possessing Shared Tumor Epitopes Capable of Inducing HLA-A24-Restricted Cytotoxic T Lymphocytes in Cancer Patients", Cancer Research, vol. 59, pp. 4056-4063, Aug. 15, 1999.

S. Gomi et al., "A Cyclophilin B Gene Encodes Antigenic Epitopes Recognized by LAA-A24-Restricted and Tumor-Specific CTLs[1]", The Journal of Immunology, vol. 163, pp. 4994-5004, 1999.

Y. Maeda et al., "Cleavage and Polyadenylation Specificity Factor (CPSF)-Derived Peptides can Induce HLA-A2-Restricted and Tumor-Specific CTLS in the Majority of Gastrointestinal Cancer Patients", Int. J. Cancer, vol. 99, pp. 409-417, 2002.

N. Suzuki et al., Detection of Peptide-Specific Cytotoxic T-Lymphocyte Precursors used for Specific Immunotherapy of Pancreatic Cancer, Int. J. Cancer, vol. 98, pp. 45-50, 2002.

Y. Miyagi et al., "Induction of Cellular Immune Responses to Tumor Cells and Peptides in Colorectal Cancer Patients by Vaccination with SART3 Peptides[1]", Clinical Cancer Research, vol. 7, pp. 3950-3962, Dec. 2001.

N. Hida et al., "A Simple Culture Protocol to Detect Peptide-Specific Cytotoxic T Lymphocyte Precursors in the Circulation", Cancer Immunol. Immunotherapy, vol. 51, pp. 219-228, 2002.

M. Noguchi et al., "Pyridinoline Cross-Linked Carboxyterminal Telopeptide of Type I Collagen as a Useful Marker for Monitoring Metastatic Bone Activity in Men with Prostate Cancer", The Journal of Urology, vol. 166, pp. 1106-1110, Sep. 2001.

M. Noguchi et al., "Percentage of the Positive Area of Bone Matastasis is an Independent Predictor of Disease Death in Advanced Prostate Cancer", British Journal of Cancer, vol. 88, pp. 195-201, 2003.

M. S. Mitchell, "Chemotherapy in Combination with Biomodulation: A 5-Year Experience with Cyclophosphamide and Interleukin-2", Seminars in Oncology, vol. 19, No. 2, Suppl. 4, pp. 80-87, Apr. 1992.

S. Zhang et al., "Selection of Tumor Antigens as Targets for Immune Attack Using Immunohistochemistry: I. Focus on Gangliosides", Int. J. Cancer, vol. 73, pp. 42-49, 1997.

S. Zhang et al., "Selection of Tumor Antigens as Targets for Immune Attack Using Immunohistochemistry: II. Blood Group-Related Antigens", Int. J. Cancer, vol. 73, pp. 50-56, 1997.

S. Zhang et al., "Expression of Potential Target Antigens for Immunotherapy on Primary and Metastatic Prostate Cancers[1]", Clinical Cancer Research, vol. 4, pp. 295-302, Feb. 1998.

R. A. Blades et al., "Loss of HLA Class I Expression in Prostate Cancer: Implications for Immunotherapy", Urology, vol. 46, No. 5, pp. 681-687, 1995.

M. Maffezzini et al., "Salvage Immunotherapy with Subcutaneous Recombinant Interleukin 2 (rIL-2) and Alpha-Interferon (A-IFN) for Stage D3 Prostate Carcinoma Failing Second-Line Hormonal Treatment", The Prostate, vol. 28, pp. 282-286, 1996.

M. Noguchi et al., "Serum Levels of Bone Turnover Markers Parallel the Results of Bone Scintigraphy in Monitoring Bone Activity of Prostate Cancer", Urology, vol. 61, pp. 993-998, 2003.

M. Noguchi et al., "Phase I Trial of Patient-Oriented Vaccination in HLA-A2-Positive Patients with Metastatic Hormone-Refractory Prostate Cancer", Cancer Science, vol. 95, No. 1, pp. 77-84, Jan. 2004.

M. Noguchi et al., "Immunological Monitoring During Combination of Patient-Oriented Peptide Vaccination and Estramustine Phosphate in Patients with Metastatic Hormone Refractory Prostate Cancer", The Prostate, vol. 60, pp. 32-45, 2004.

Y. Inoue et al., "Induction of Tumor Specific Cytotoxic T Lymphocytes in Prostate Cancer Using Prostatic Acid Phosphatase Derived HLA-A2402 Binding Peptide", The Journal of Urology, vol. 166, pp. 1508-1513, Oct. 2001.

M. Harada et al., "Prostate-Specific Antigen-Derived Epitopes Capable of Inducing Cellular and Humoral Responses in HLA-A24[+] Prostate Cancer Patients", The Prostate, vol. 57, pp. 152-159, 2003.

K. Kobayashi et al., "Identification of a Prostate-Specific Membrane Antigen-Derived Peptide Capable of Eliciting Both Cellular and Humoral Immune Responses in HLA-A24[+] Prostate Cancer Patients", Cancer Science, vol. 94, No. 7, pp. 622-627, Jul. 2003.

M. Harada et al., "Target Molecules in Specific Immunotherapy Against Prostate Cancer", Int. J. Clin. Oncol., vol. 8, pp. 193-199, 2003.

N. Harashima et al., "Recognition of the Lck Tyrosine Kinase as a Tumor Antigen by Cytotoxic T Lymphocytes of Cancer Patients with Distant Metastases", Eur. J. Immunol. vol. 31, pp. 323-332, 2001.

K. Kawano et al., "Identification of a New Endoplasmic Reticulum-Resident Protein Recognized by HLA-A24-Restricted Tumor-Infiltrating Lymphocytes of Lung Cancer", Cancer Research, vol. 60, pp. 3550-3558, Jul. 1, 2000.

P. Esper et al., "Measuring Quality of Life in Men with Prostate Cancer Using the Functional Assessment of Cancer Therapy-Prostate Instrument", Urology, vol. 50, No. 6, pp. 920-928, 1997.

S. J. Coons et al., "Assessing Health-Related Quality of Life: Application to Drug Therapy", Clinical Therapeutics, vol. 14, No. 6, pp. 850-858, 1992.

* cited by examiner

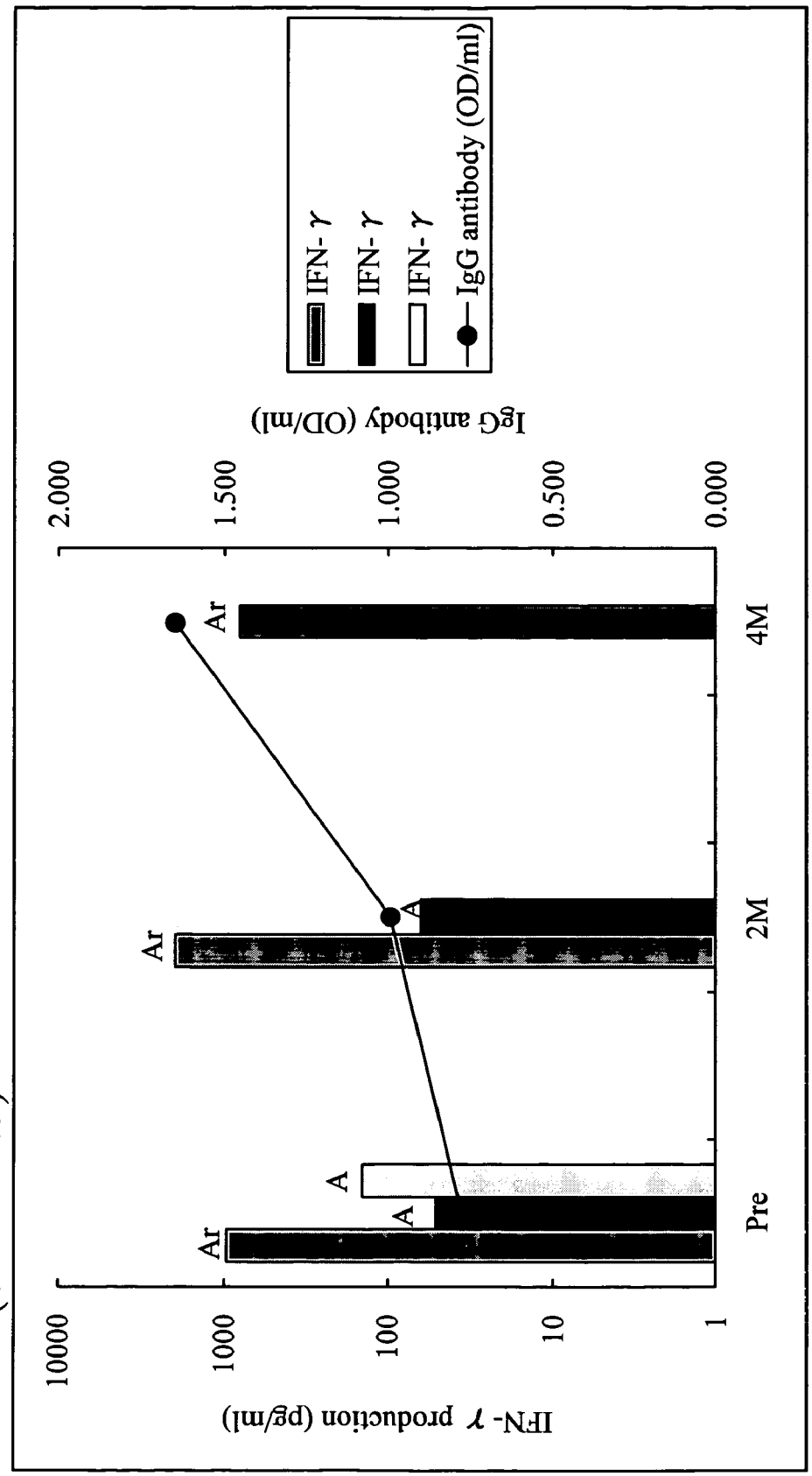

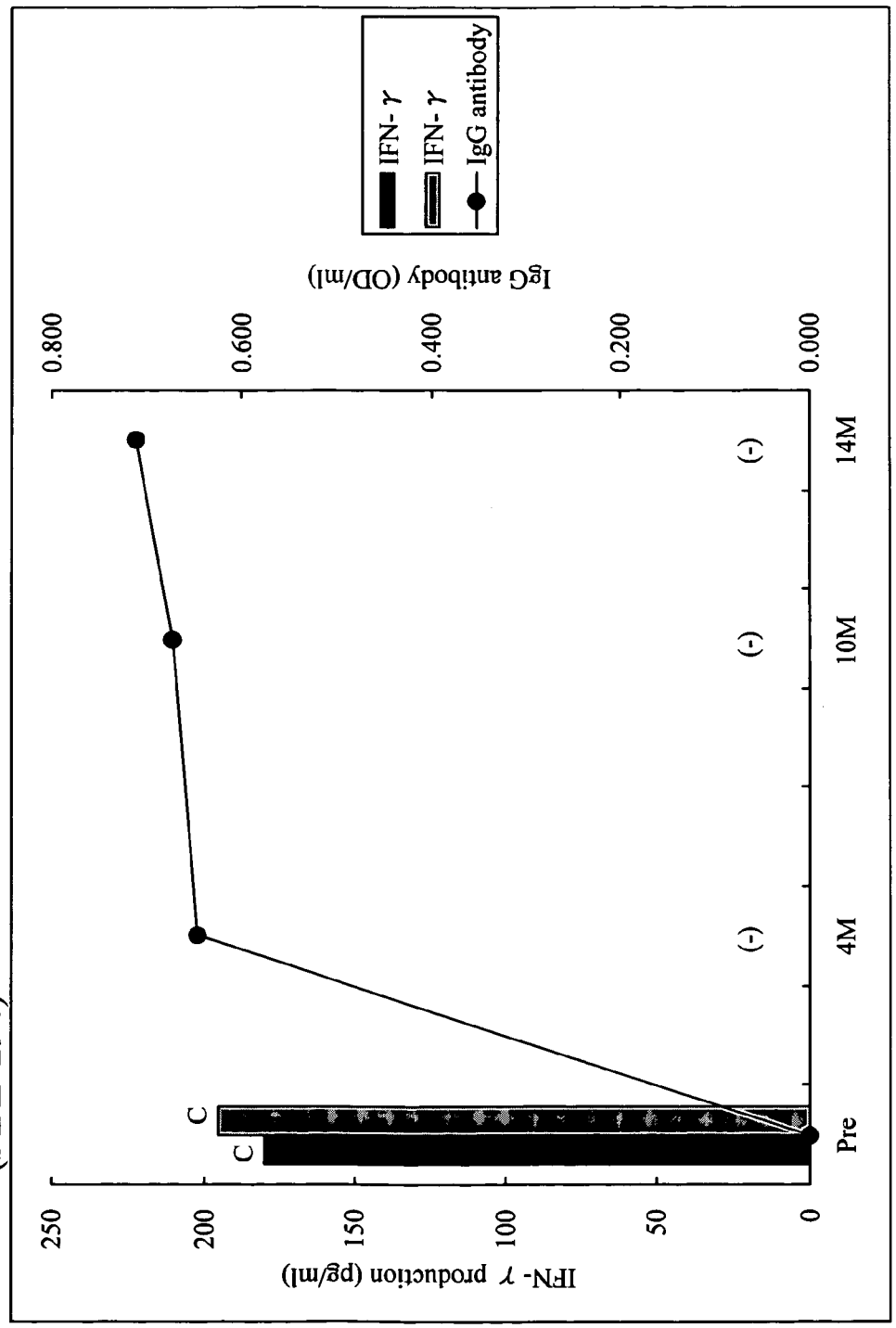

Case 10 (SART3 309)

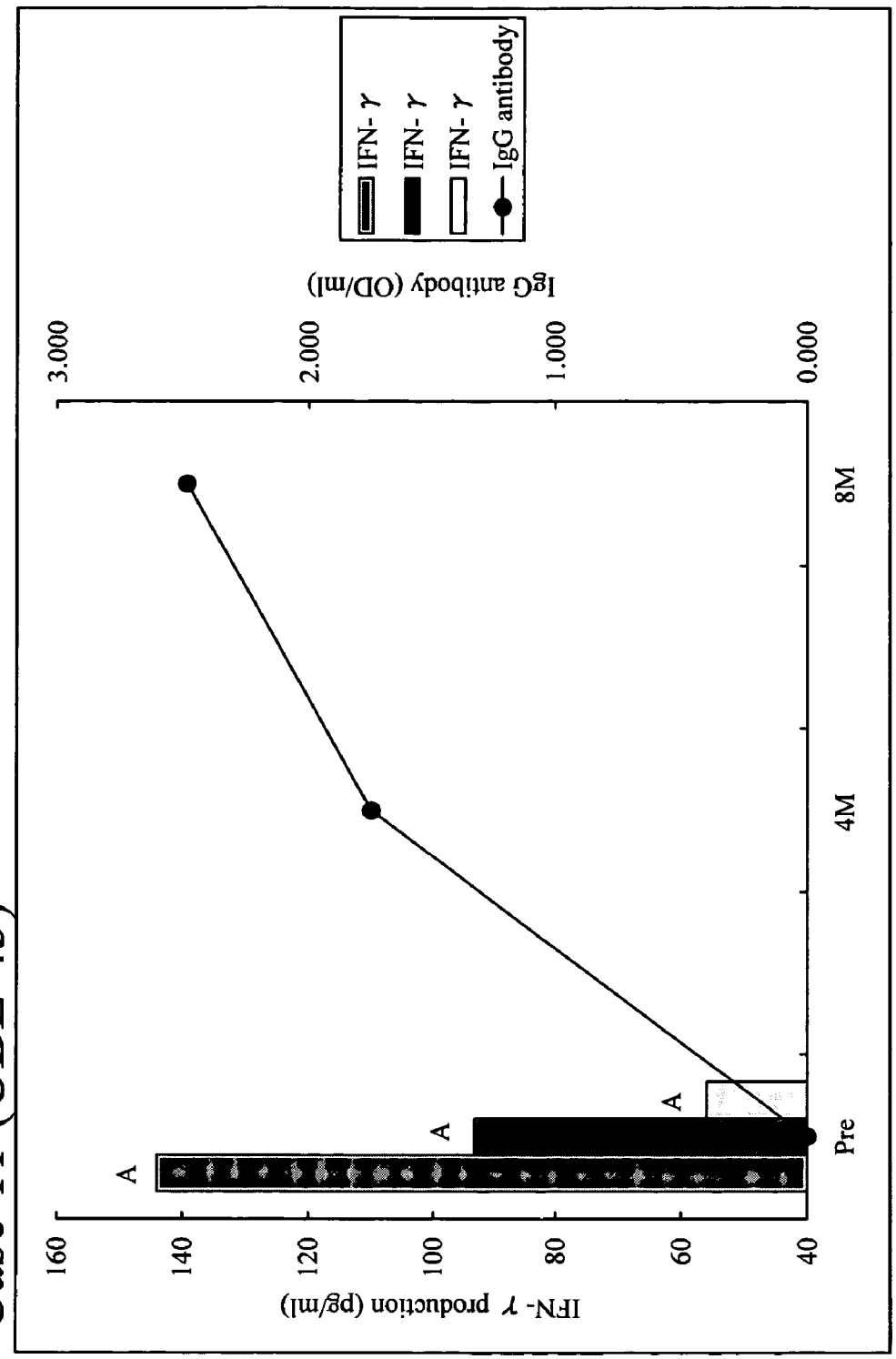

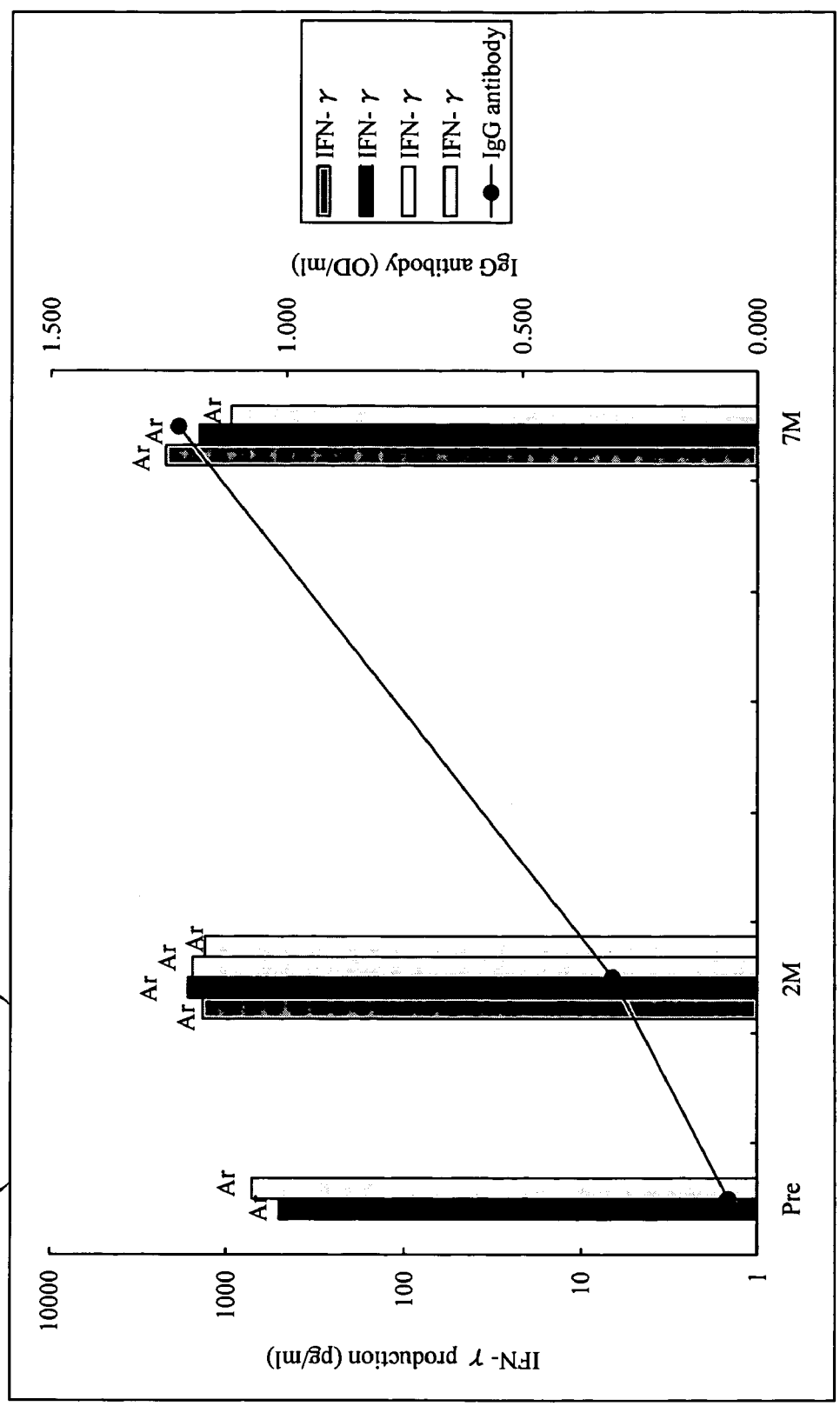

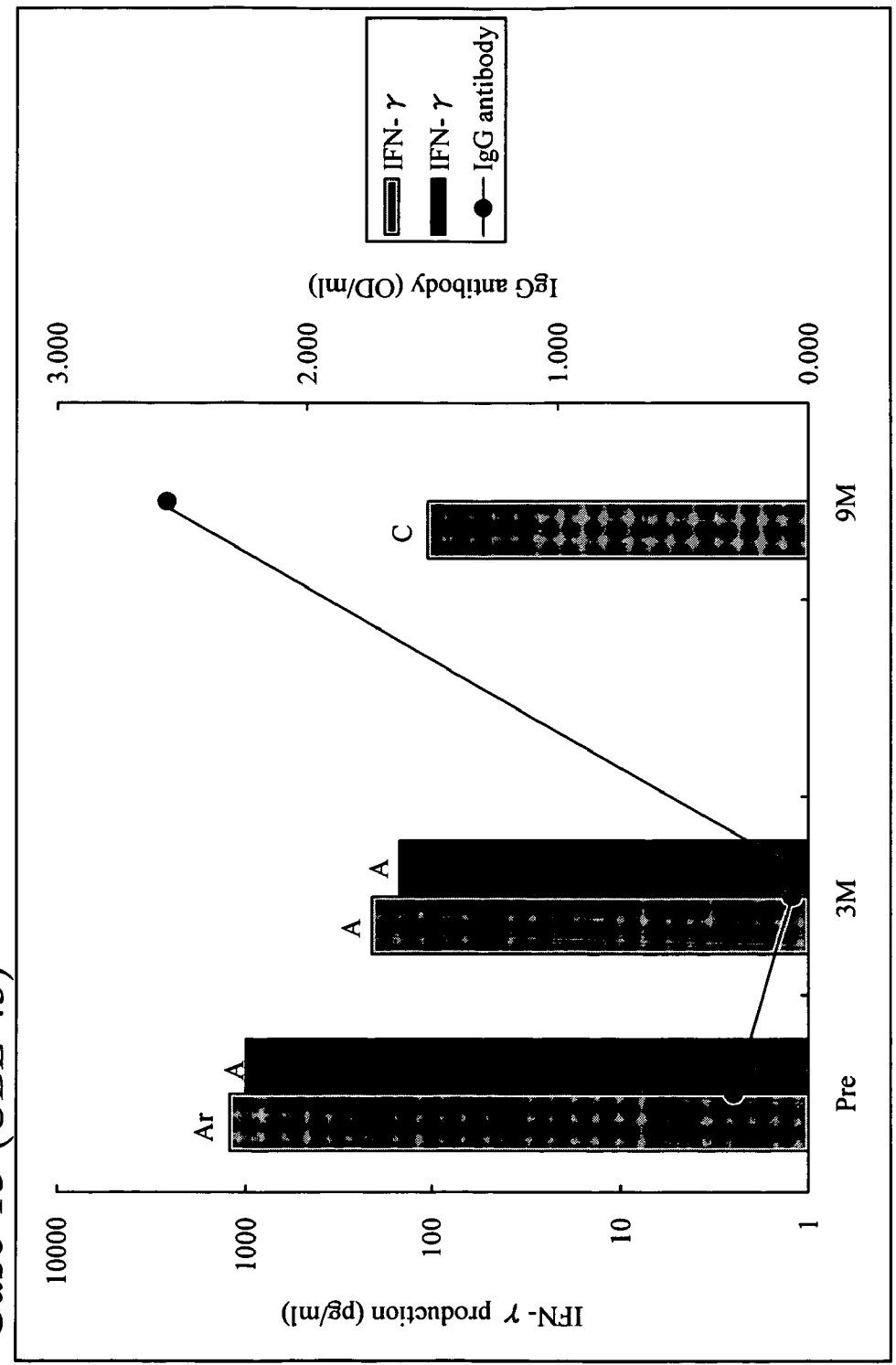

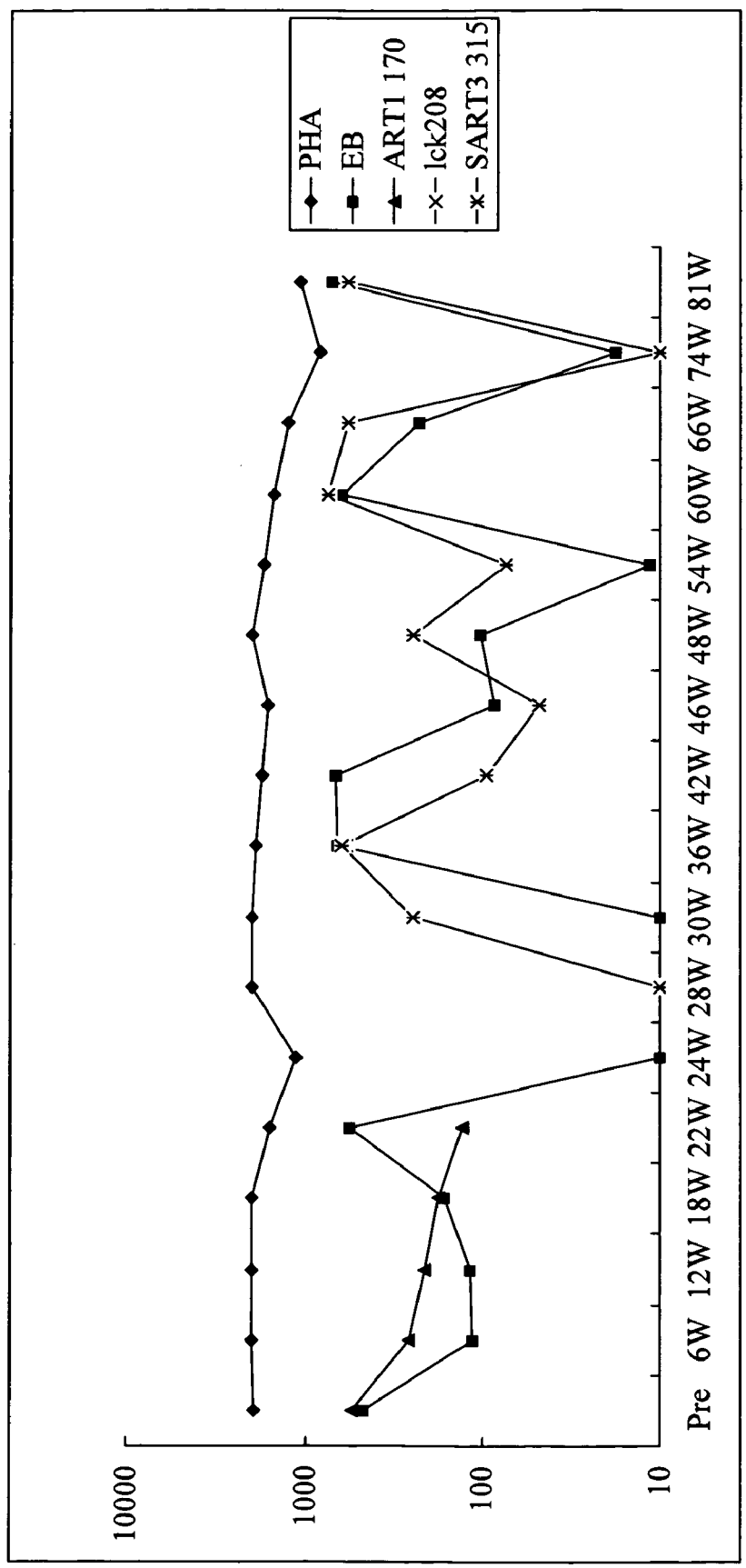
Fig. 2A Case 2

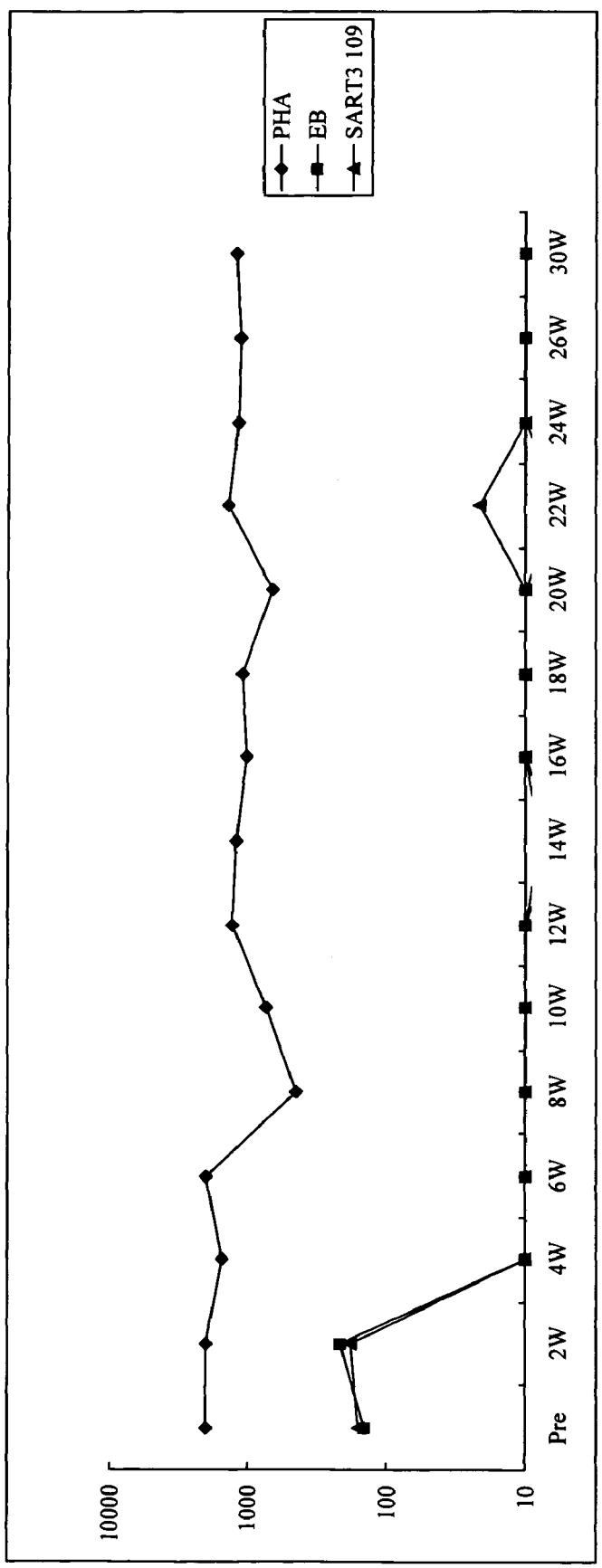

Case 4

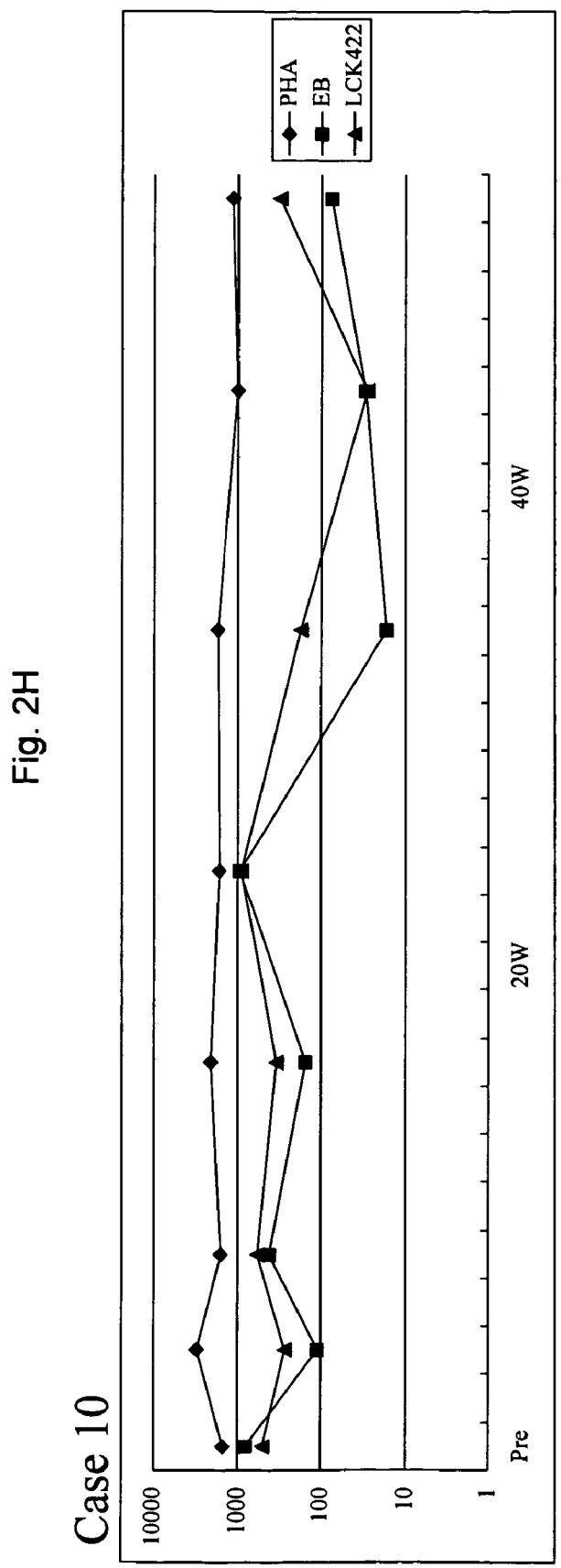

Case 2

Case 3

Case 11

Case 12

Patient 7

Patient 11

Patient 13

COMBINATION THERAPY OF PEPTIDE VACCINATION AND ESTRAMUSTINE TREATMENT

CROSS-REFERENCE TO RELATED APPLICATIONS

This application is a continuation-in-part application of International application Nos. PCT/JP03/14010 filed on Oct. 31, 2003 and PCT/JP2004/016497 filed Oct. 29, 2004 claiming the benefit of PCT/JP03/14010, the whole contents and disclosure of which are herein incorporated by reference.

TECHNICAL FIELD

The present invention relates to immunotherapy for cancers, and specifically it relates to treatment for hormone-refractory prostate cancers.

BACKGROUND ART

The optimal treatment strategy for patients with metastatic hormone-refractory prostate cancer (HRPC) continues to represent a challenge for oncologists. The median survival duration of patients with metastatic HRPC is about 12 months [1-3]. Although chemotherapy with mitoxantrone offers a palliative benefit [1, 2], no treatment has been shown to prolong survival. Recently, phase II trials of estramustine-based or taxane-based regimes reported a≧50% decrease in levels of serum prostate-specific antigen (PSA) in 45% to 67% of patients [4-8]. However, these combinations were associated with a significant degree of nausea, diarrhea, leukopenia, and cumulative fluid retention and an increased risk for thrombotic events, precluding its use in patients with a poor performance status. In addition, none of these regimes is associated with prolonged survival and the number of patients in these studies was limited.

Many tumor antigens recognized by human leukocyte-associated antigens (HLA) class I-restricted cytotoxic T lymphocytes (CTLs) have been identified in the past decade [9, 10], and new approaches for HRPC with tumor vaccines have been investigated. Phase I/II clinical trials with dendritic cell-based immunotherapy have been conducted, and also a vaccine comprising a recombinant prostate-specific membrane antigen (PSMA) and an adjuvant has been tested in prostate cancer patients [11, 12]. Our approach in the immunotherapy for HRPC patients is a pre-vaccination measurement of peptide-specific CTL precursors in the circulation of cancer patients reactive to 30 kinds of vaccine candidates with the ability to induce CTLs, followed by administration of only reactive peptides (patient-oriented peptide vaccination) as reported previously [13, 14]. We recently completed our phase I clinical trial for HRPC to assess the safe administration of these peptides [15]. The adverse events of this immunotherapy were less severe than those of conventional therapies although the clinical responses of this trial have been limited. It is suggested that additive anti-tumor effects could be achieved by combination of peptide vaccination and cytotoxic agents when the cytotoxic agents had minimum suppression of immune system.

Estramustine phosphate is a stable conjugate of estradiol and nitrogen mustard that possesses anti-mitotic properties and causes disruption of microtubule organization [16]. Estramustine phosphate has been subjected to many Phase II and III clinical trials in the last 25 years as a second-line treatment of HRPC in addition to primary treatment. The advantage of estramustine phosphate over other cytotoxic drugs is its ease of administration (oral) and relatively good tolerability at the effective dose.

Combination of immunotherapy and cytotoxic drugs is not a new concept [27], but there have been major concerns about a negative interaction which might take place due to the myelosuppressive properties of many cytotoxic drugs. Cytotoxic drugs also preferentially kill cells in division, a hallmark of an activated immune system, and therefore could inhibit immune responses. However, myelosuppression has rarely been reported as a toxicity of estramustine phosphate in patients treated for HRPC [16]. In a phase III study of estramustine phosphate combined with vinblastine versus vinblastine alone, the rate of neutropenia was lower in the combination arm versus the monotherapy arm (grades 2, 3, 4: 7%, 1% and 1% versus 27%, 18% and 9%, respectively)[3].

DISCLOSURE OF THE INVENTION

The aim of the present invention is to evaluate the clinical and immunological responses of a combination of patient-oriented peptide vaccination and oral estramustine phosphate in patients with HRPC by analyzing serially measured serum PSA, bone turnover marker together with clinical bone scan recordings, peptide-specific CTL precursors by IFN-γ-release assay, and peptide-reactive IgG by an enzyme-linked immunosorbent assay.

Thus, the present invention relates to:

(1) A method for treating a prostate cancer, which comprises administering a therapeutically effective amount of a cancer antigen peptide-associated agent and a lower dose of an estramustine or a salt thereof to a patient in need thereof;

(2) The method of (1), wherein the lower dose of an estramustine or a salt thereof is 140 to 560 mg/day;

(3) The method of (1) or (2), wherein the cancer antigen peptide-associated agent is patient-oriented;

(4) The method of (3), wherein the cancer antigen peptide-associated agent is selected from a group consisting of a cancer antigen protein, a cancer antigen peptide thereof, a gene thereof, and a derivative of their substances;

(5) The method of any one of (1) to (4), wherein the cancer is a hormone-refractory prostate cancer;

(6) A pharmaceutical composition for treating a prostate cancer which comprises a lower dose of an estramustine or a salt thereof, said composition being administered together with a cancer antigen peptide-associated agent;

(7) The pharmaceutical composition of (6), wherein the lower dose of an estramustine or a salt thereof is 140 to 560 mg/day;

(8) The pharmaceutical composition of (6) or (7), wherein the cancer antigen peptide-associated agent is patient-oriented;

(9) The pharmaceutical composition of (8), wherein the cancer antigen peptide-associated agent is selected from a group consisting of a cancer antigen protein, a cancer antigen peptide thereof, a gene thereof, and a derivative of their substances;

(10) The pharmaceutical composition of any one of (6) to (9), wherein the cancer is a hormone-refractory prostate cancer; and

(11) Use of an estramustine or a salt thereof for preparation of a medicament for treating a prostate cancer, wherein the estramustine or a salt thereof is in a lower dose, and wherein the medicament is administered together with a cancer antigen peptide-associated agent.

BRIEF DESCRIPTION OF DRAWINGS

FIG. 1A to 1J depict the graphs showing the serial changes of IFN-γ productions and IgG levels specific for the peptides administered in each case. Augmentation of peptide-specific CTL precursors was observed in cases 2, 5, 7, 8, 10 and 12, while induction of peptide-specific IgG was observed in cases 3, 4, 5, 7, 8, 10, 11, 12 and 13.

FIG. 2A to 2J depict the graphs showing the monitoring of the treatment-induced immune suppression. Cases 2 and 3 revealed severe immune suppression and their immune suppressions were recovered by discontinuing administration of full dose (560 mg/day) estramustine phosphate. There was no immune suppression in any of 8 cases when the peptide and low dose (280 mg/day) estramustine phosphate was administered.

BEST MODE FOR CARRYING OUT THE INVENTION

Figure 1A:
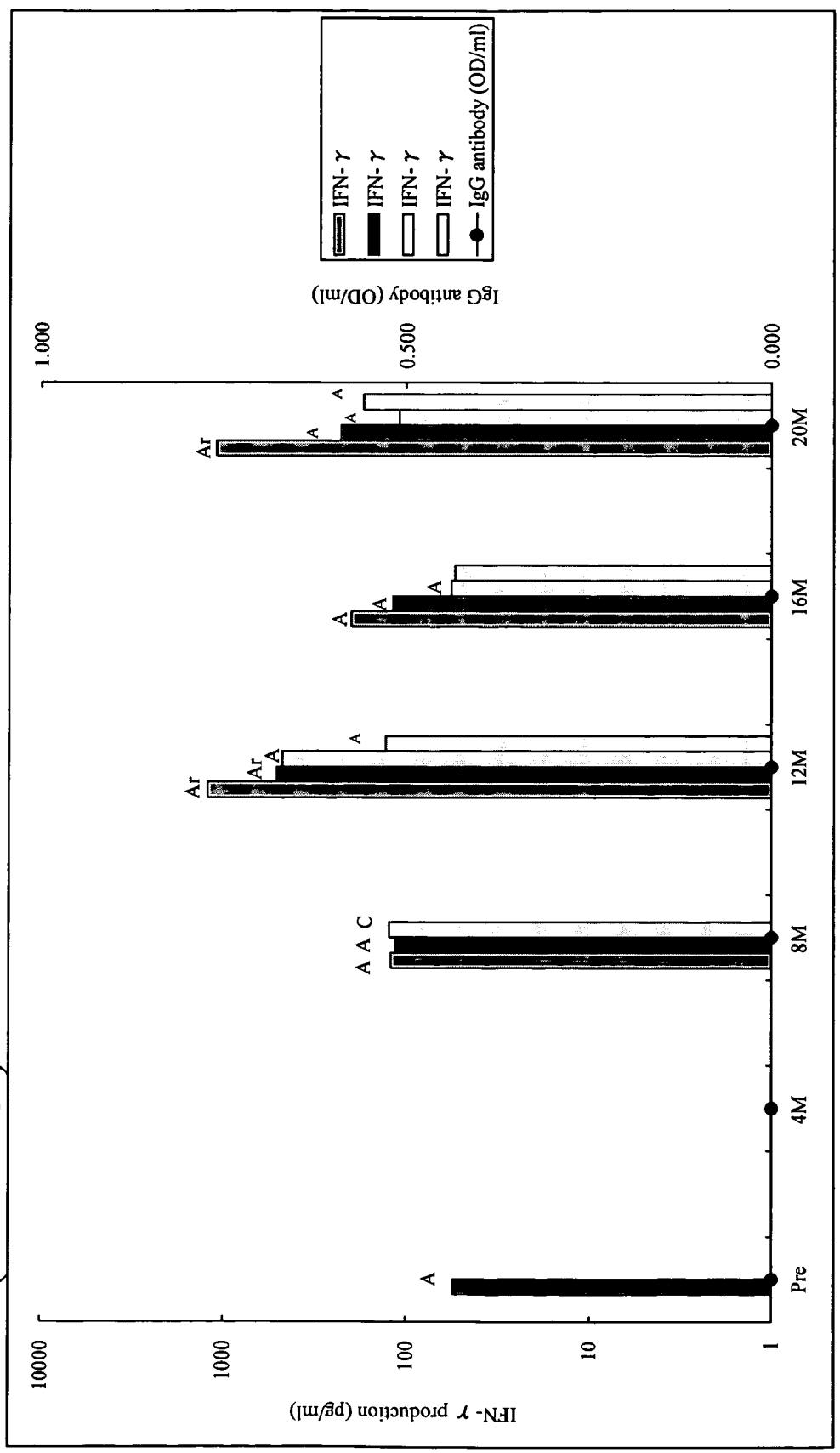
Figure 1C:
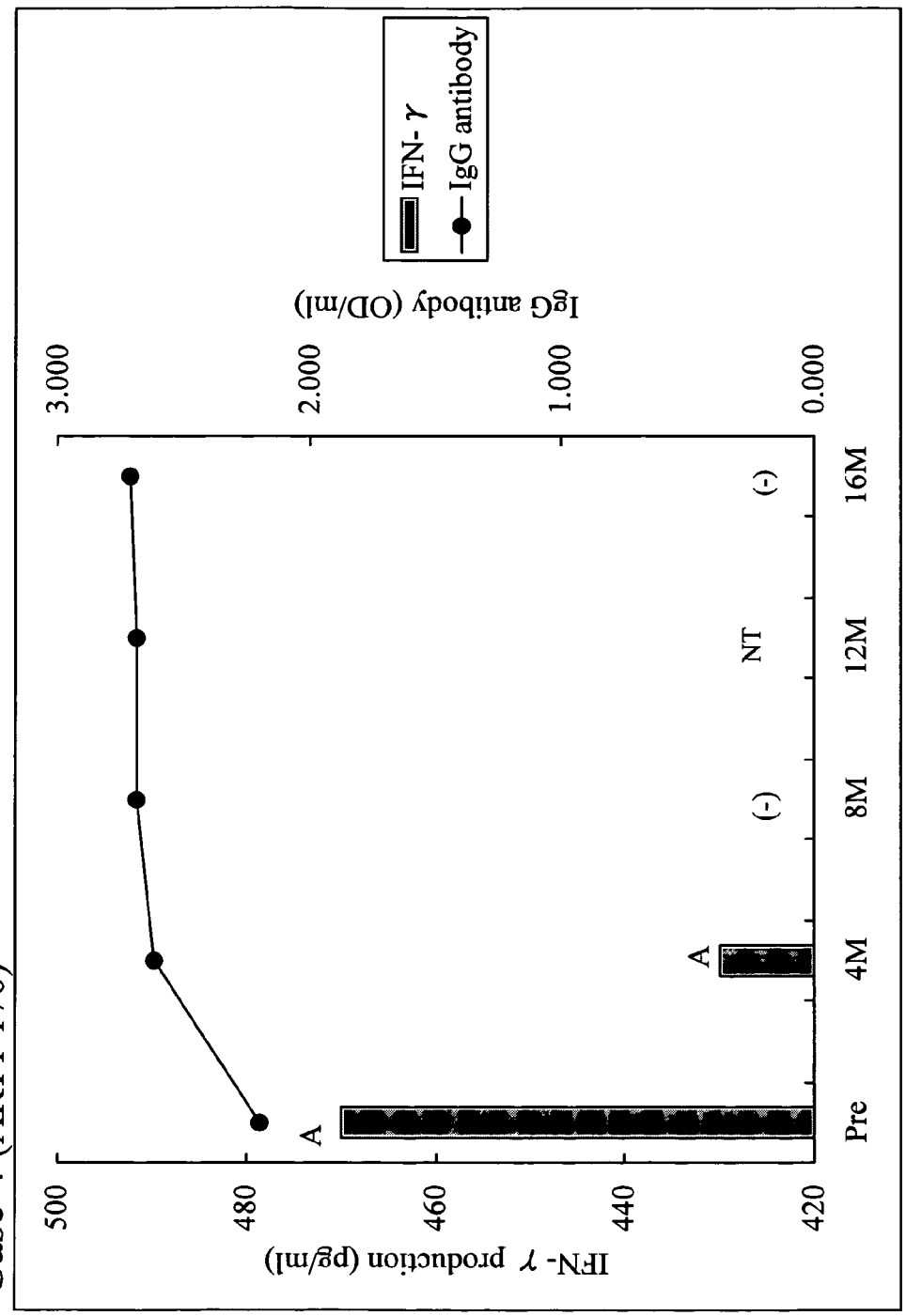
Figure 1D:
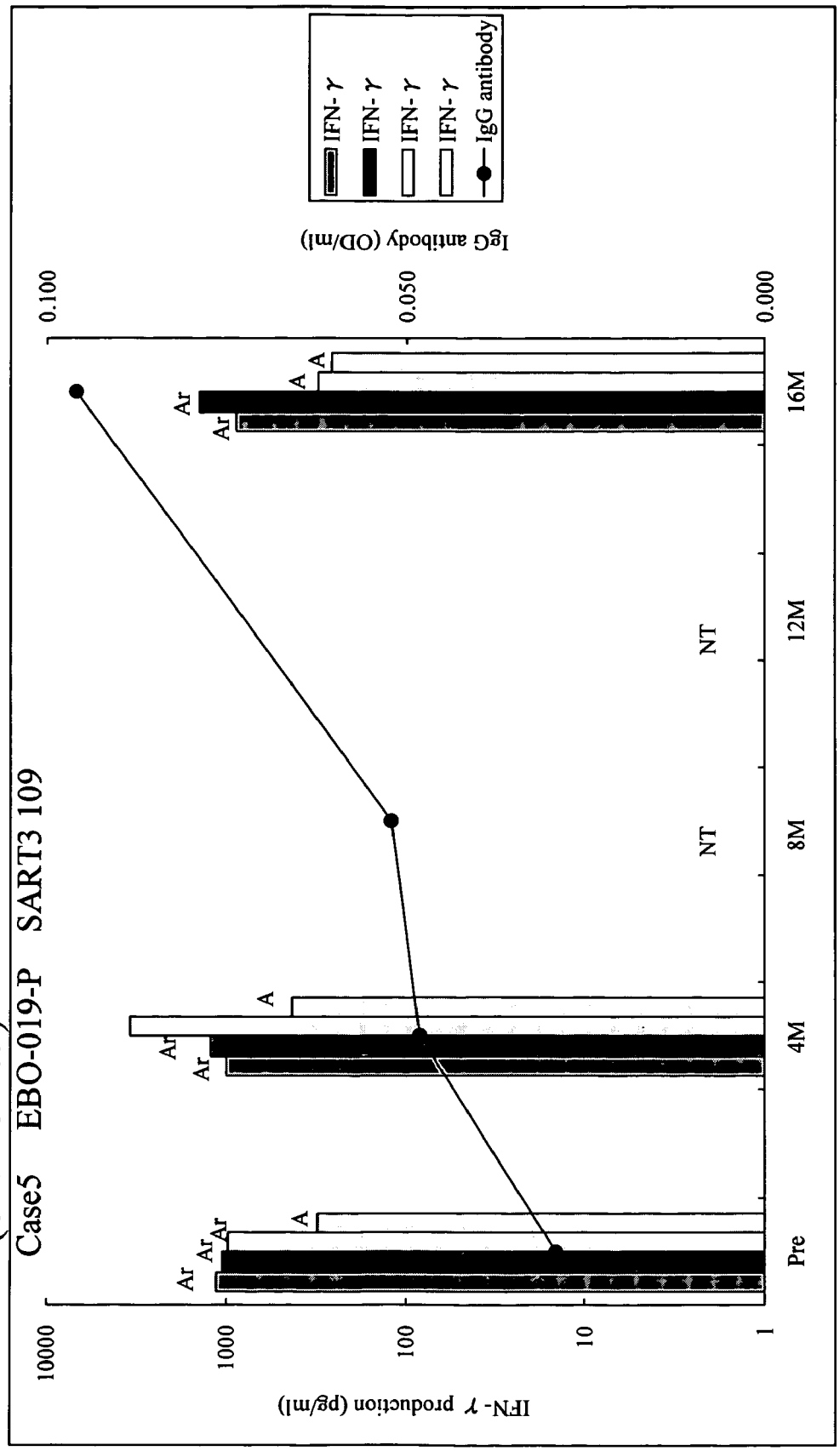
Figure 1E:
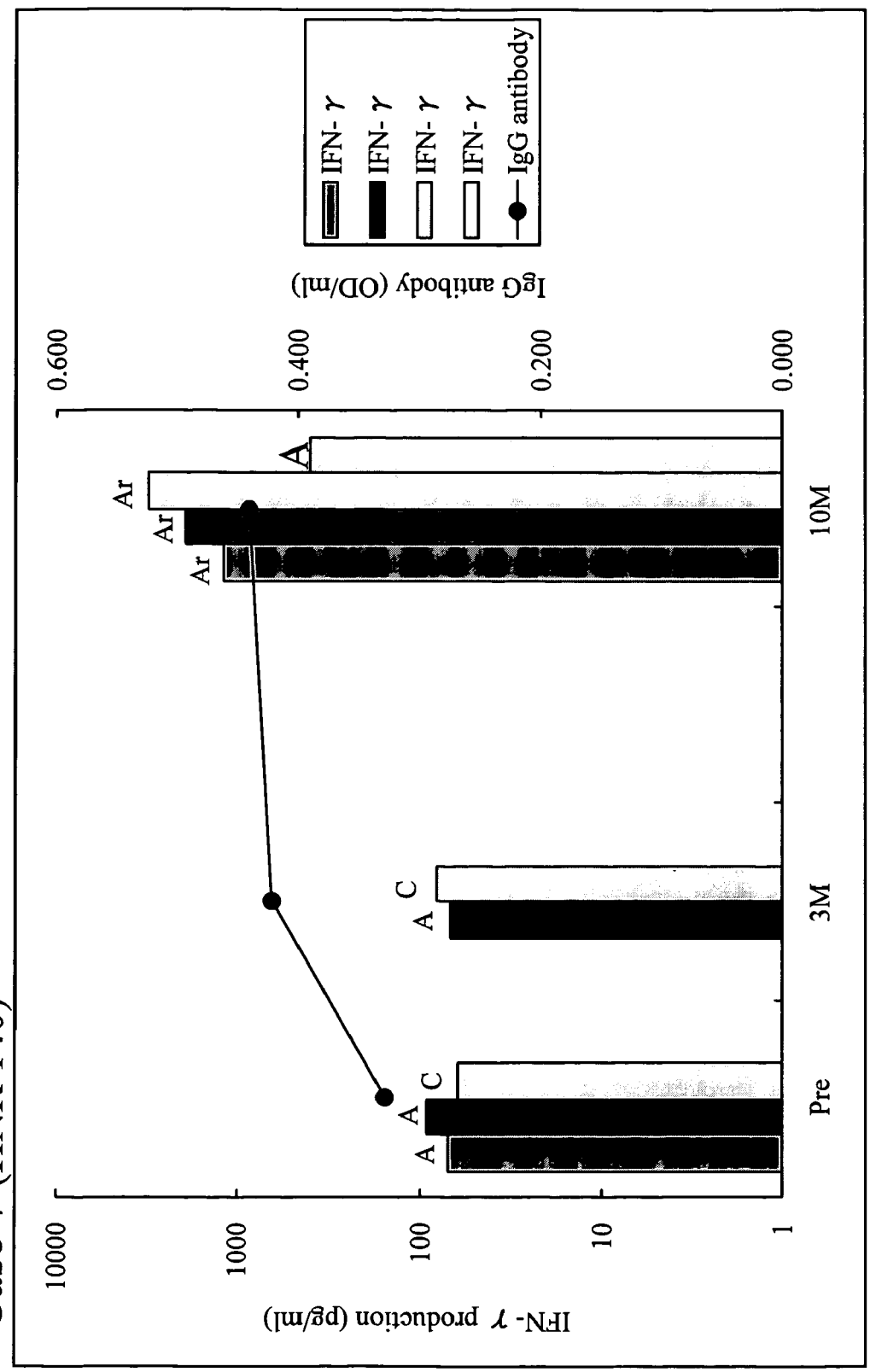
Figure 1G:
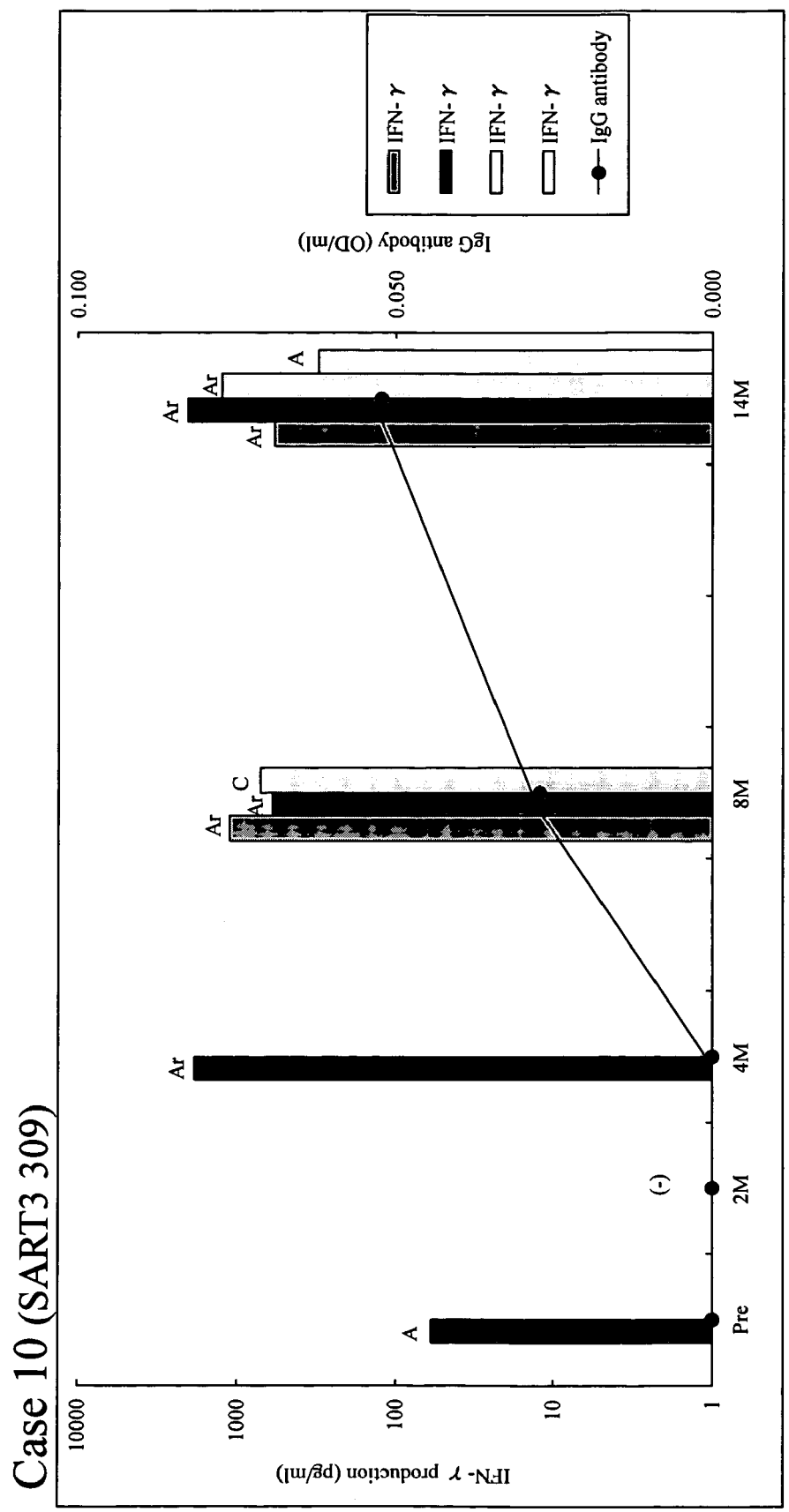
Figure 2C:
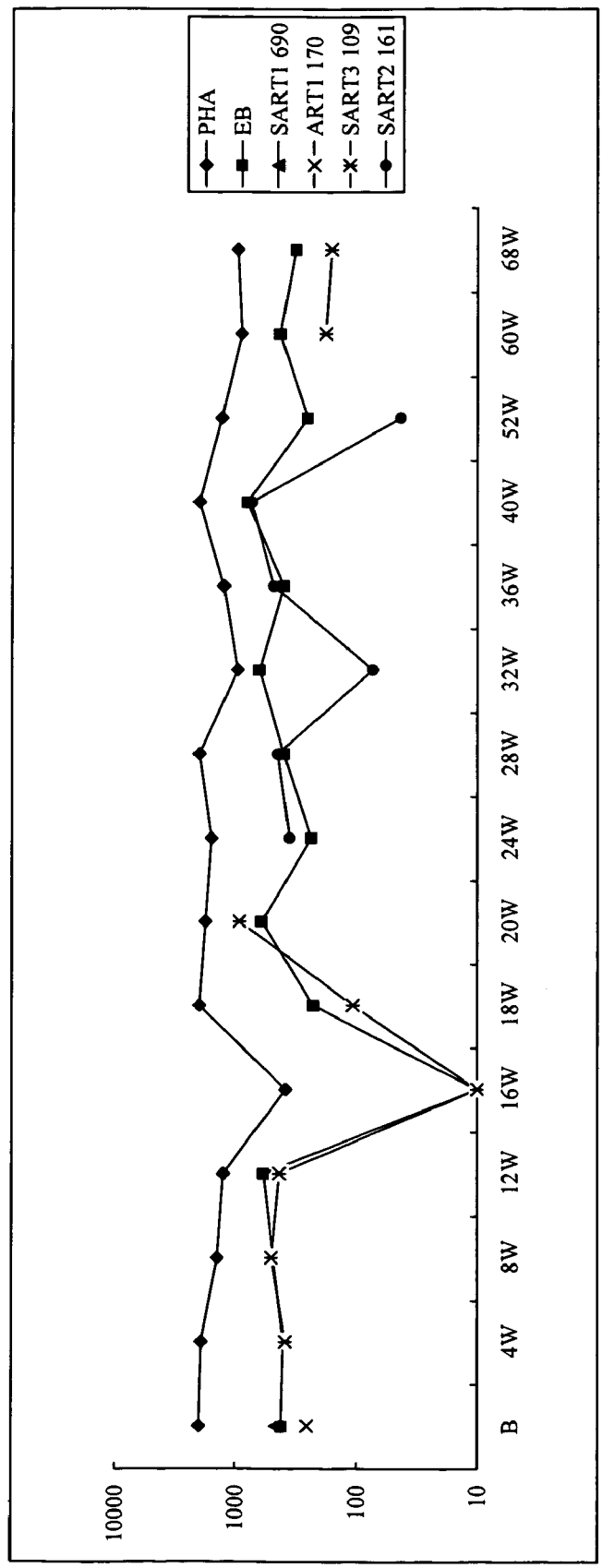
Figure 2D:
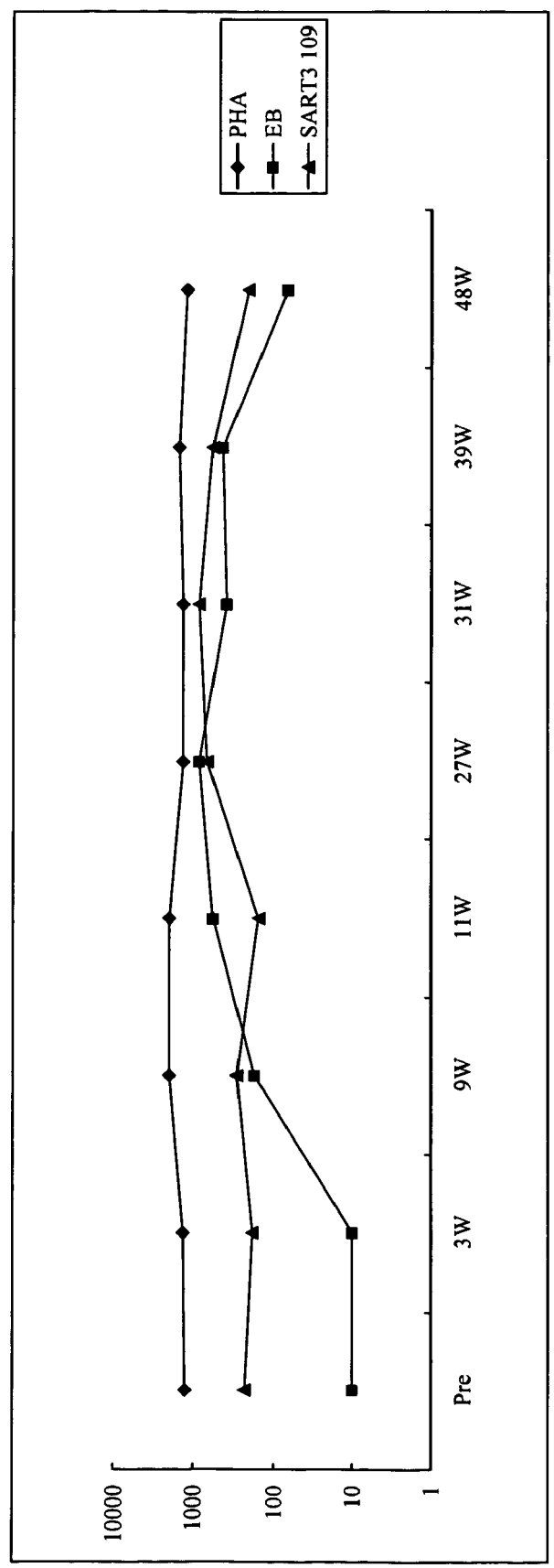
Figure 2E:
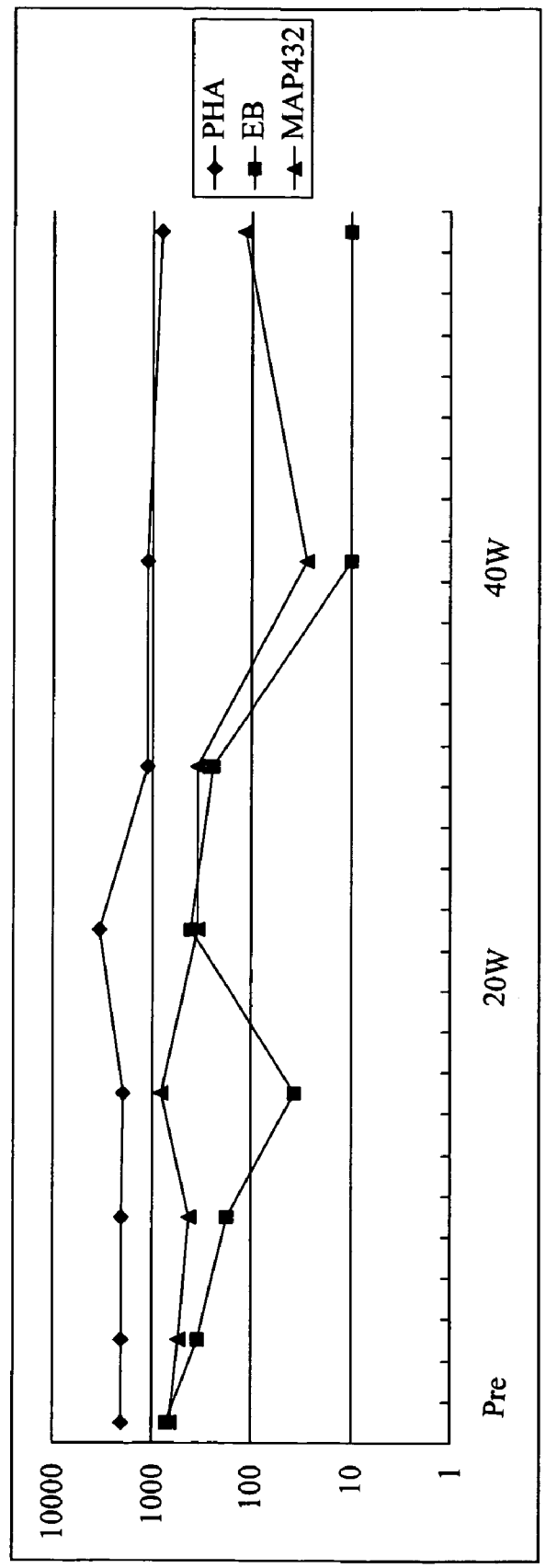
Figure 2F:
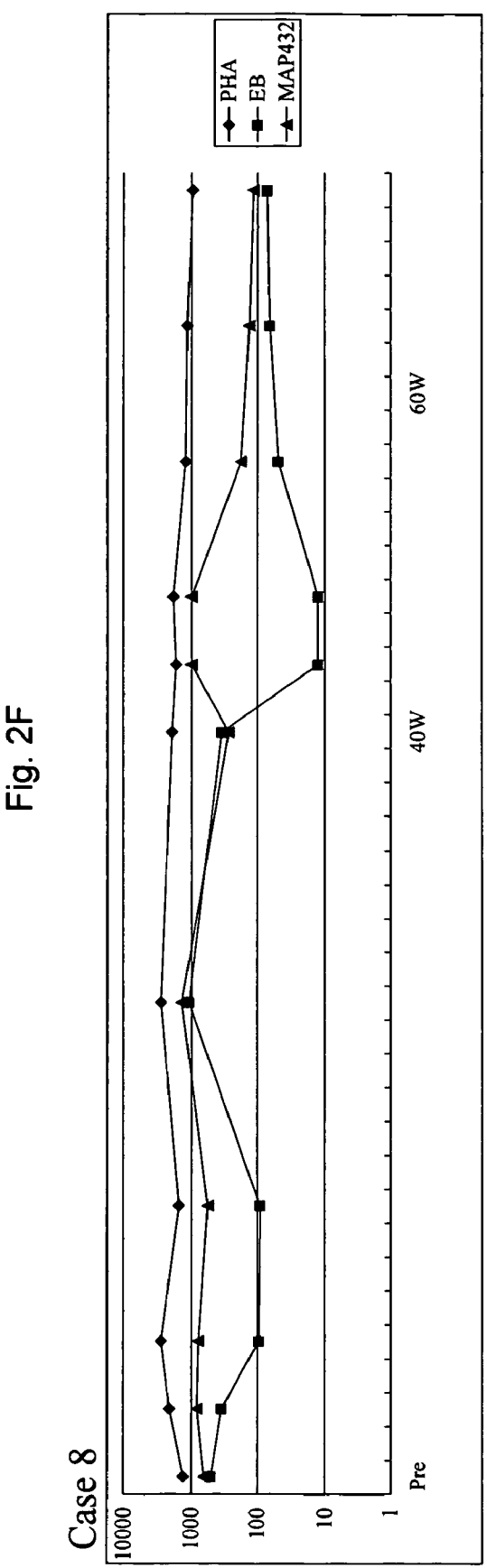
Figure 2G:
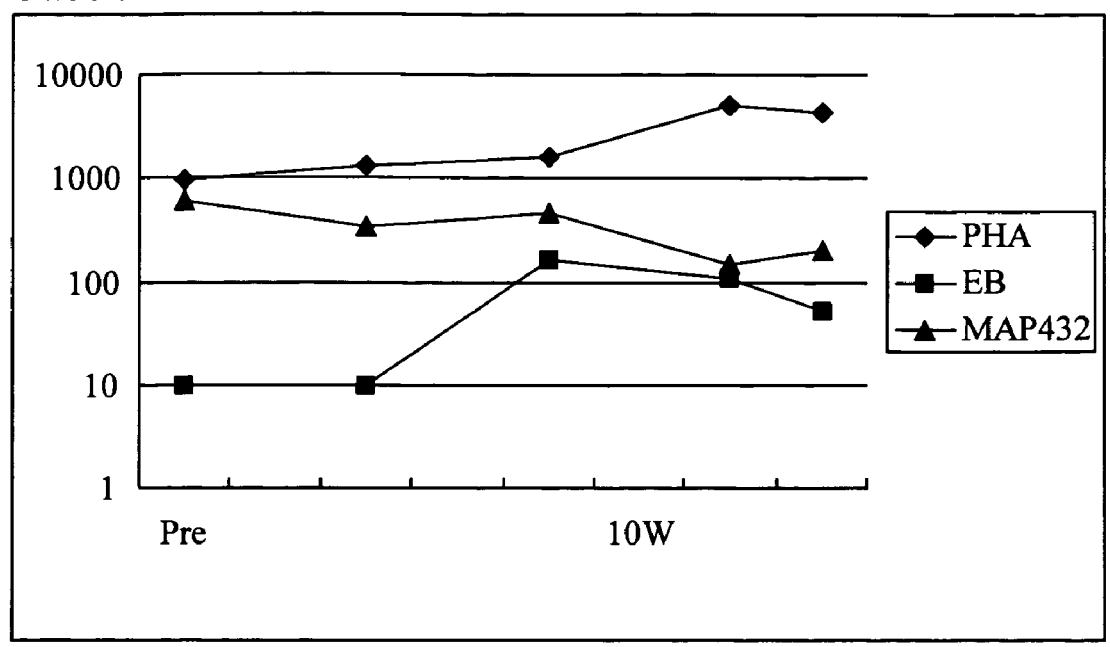
Figure 2I:
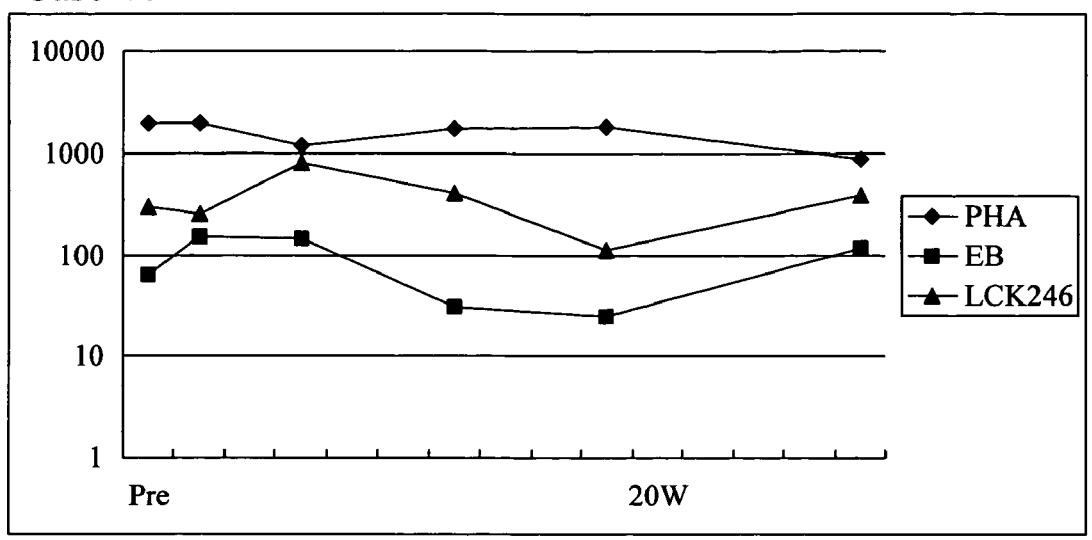
Figure 2J:
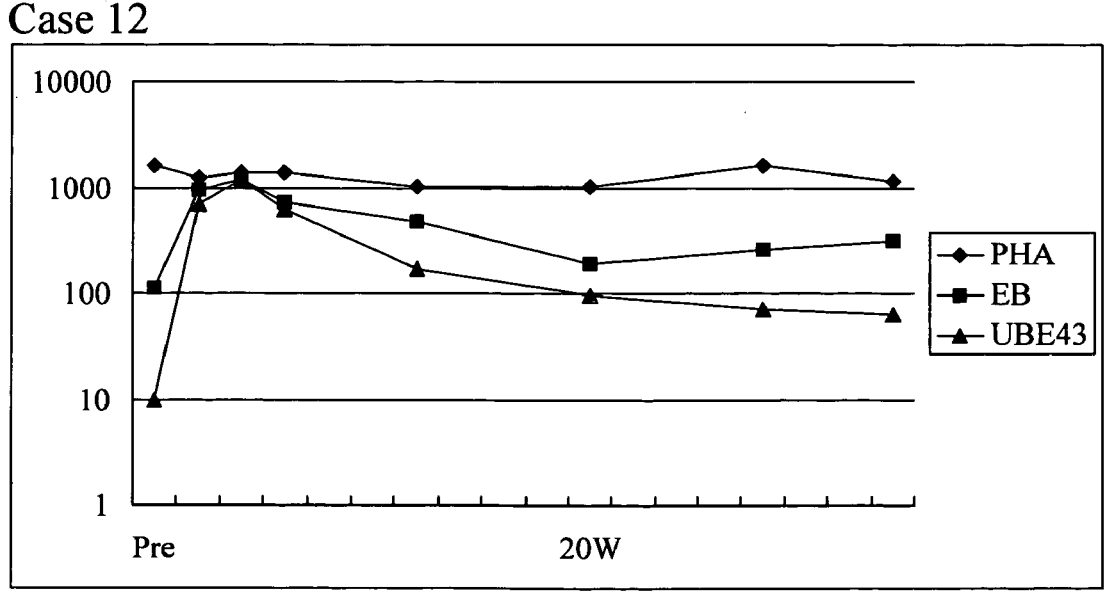
Figure 3A:
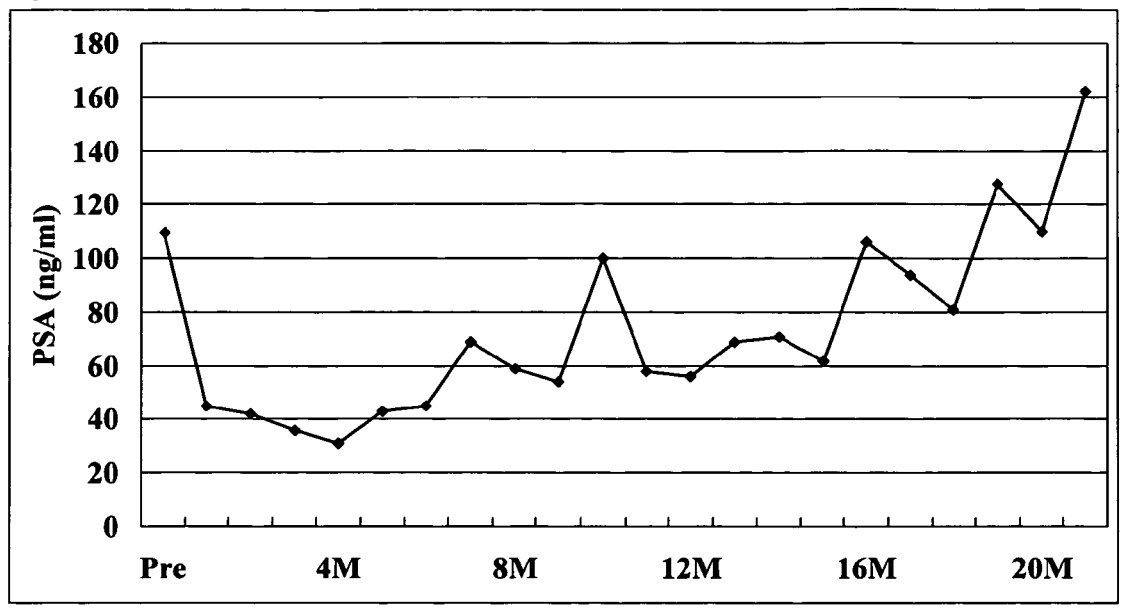
FIG. 3A to 3K depict the graphs showing the serial changes of PSA levels in 11 patients during the study. Ten of 11 (94%) patients showed serum PSA level decrease from baseline during the combination therapy.
Figure 3B:
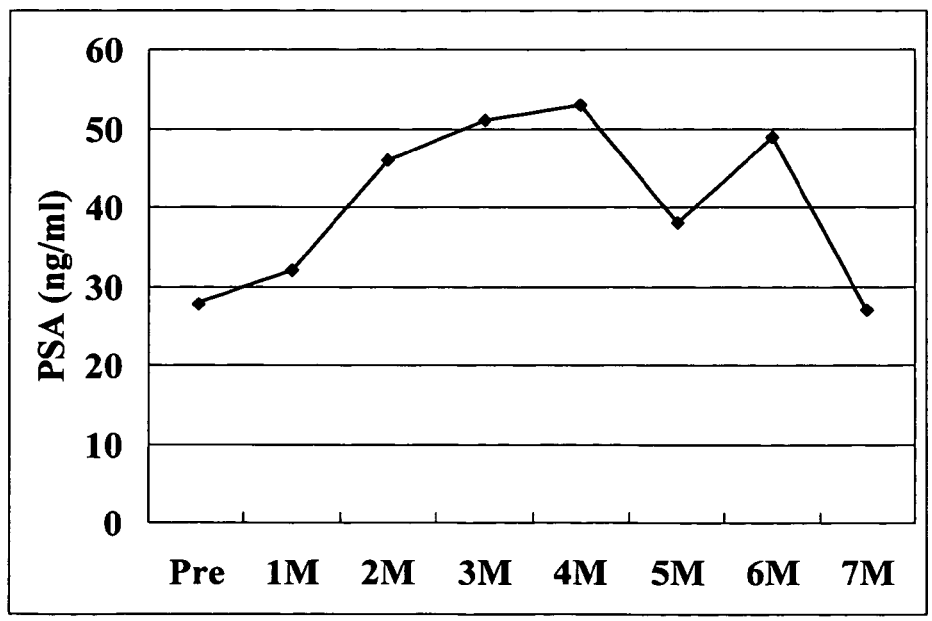
Figure 3C:
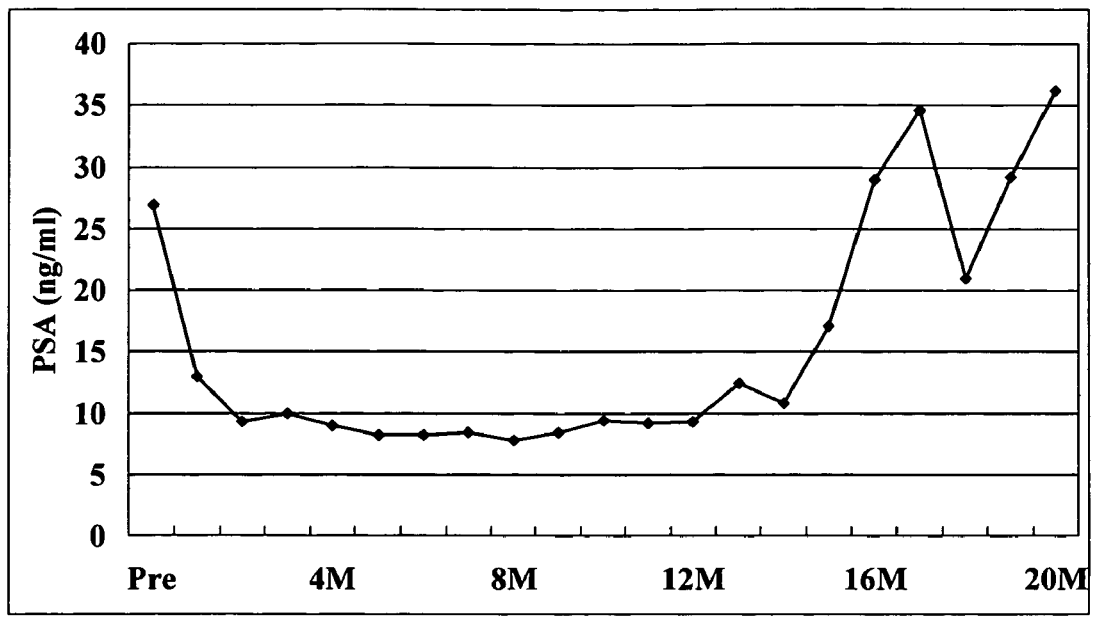
Figure 3D:
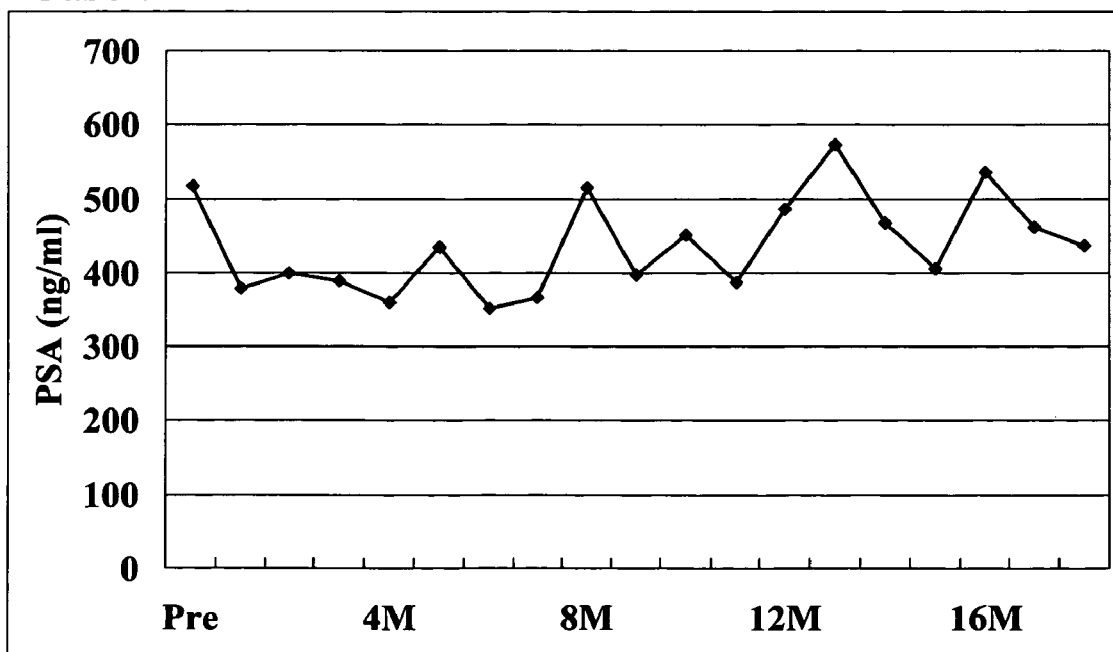
Figure 3E:
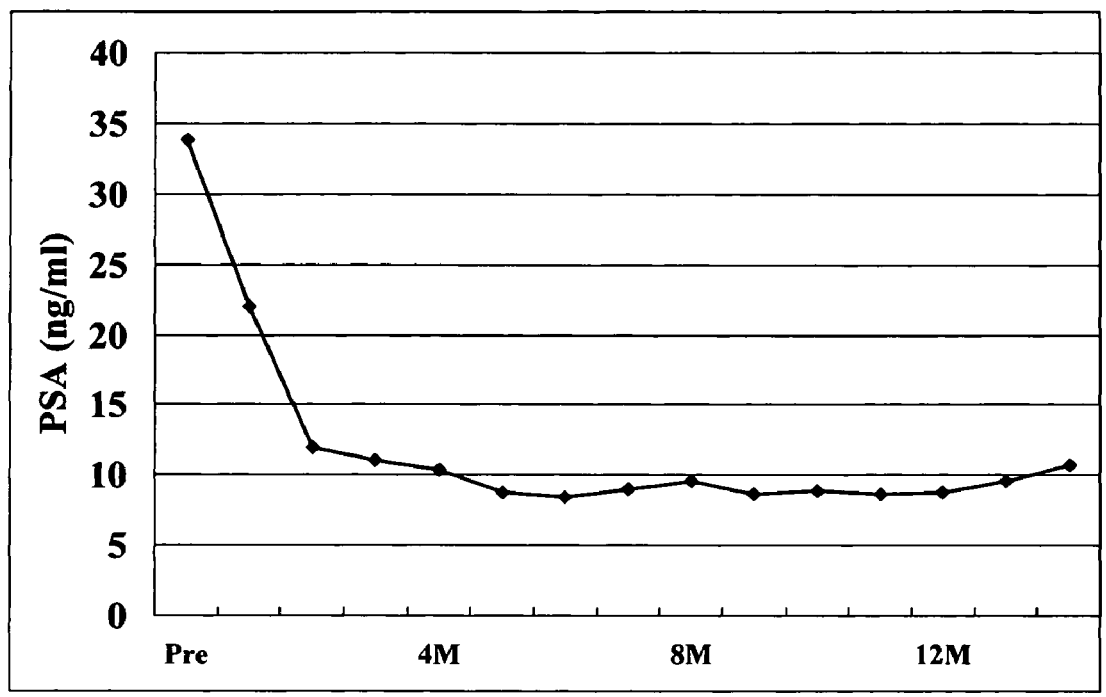
Figure 3F:
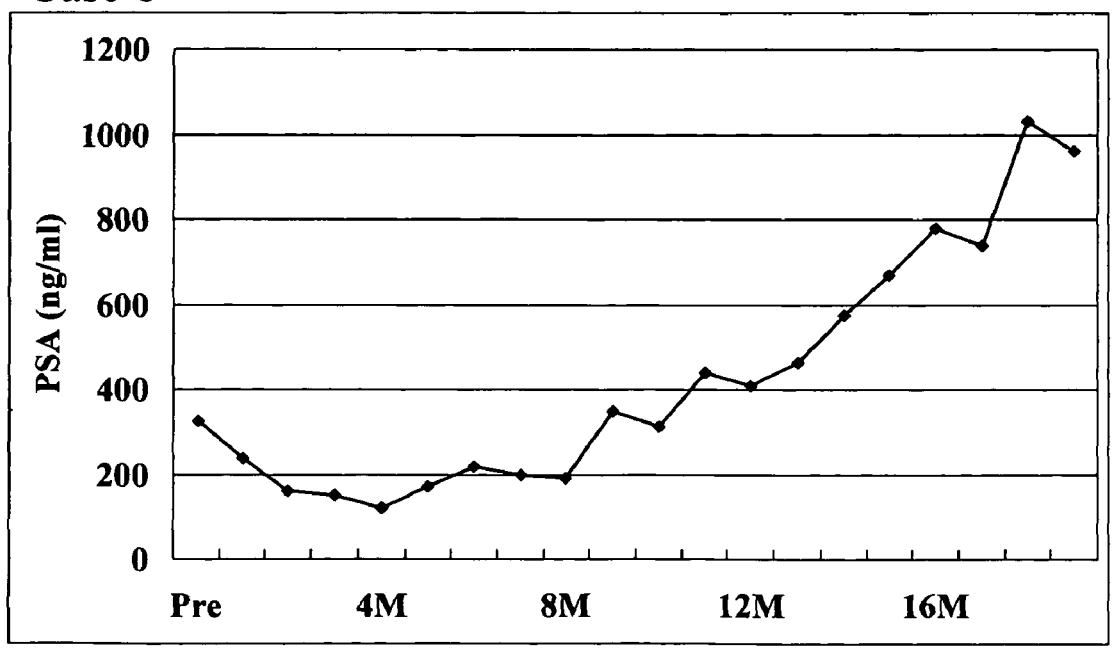
Figure 3G:
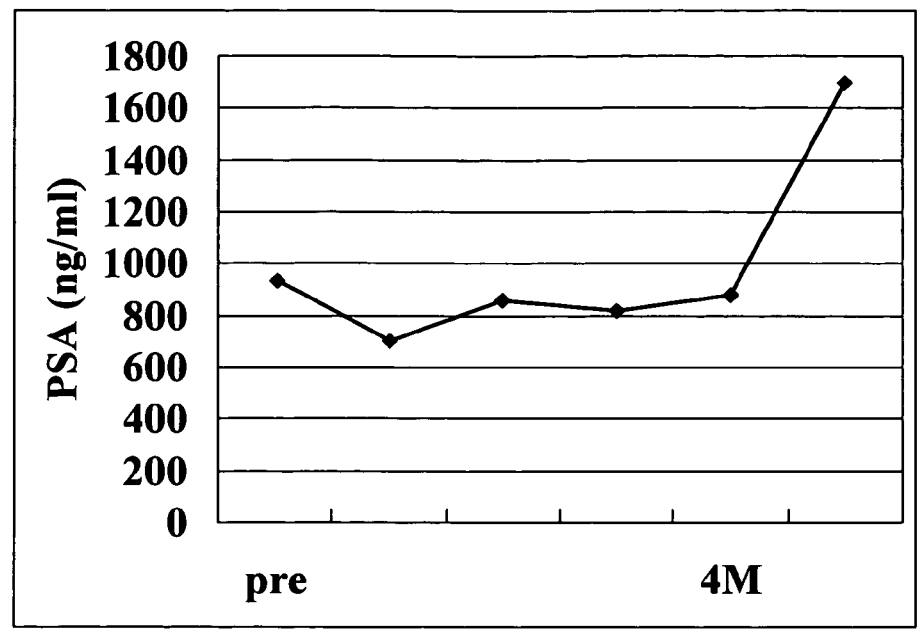
Figure 3H:
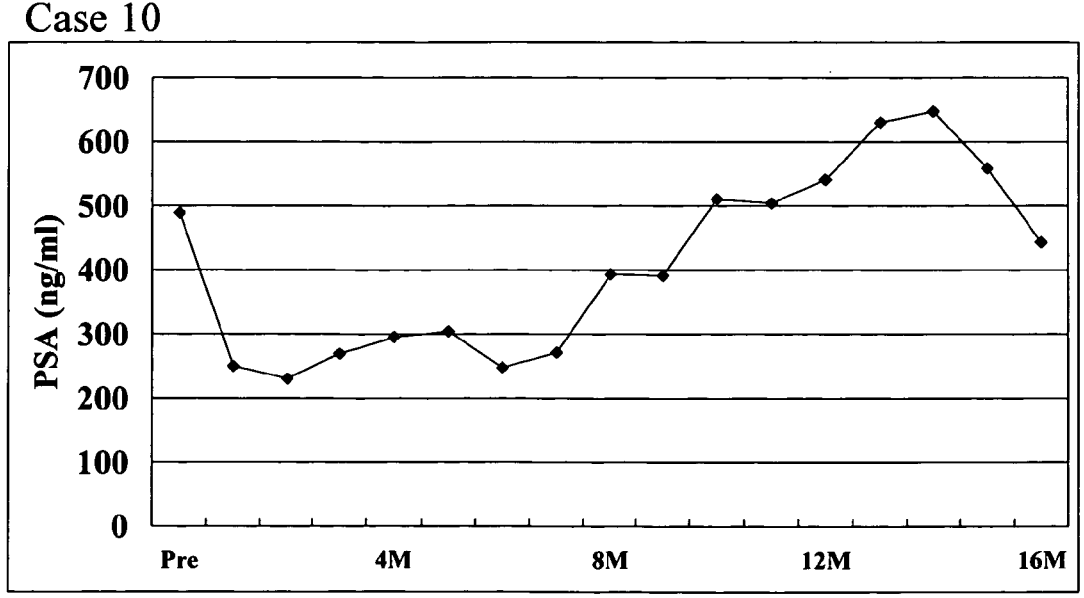
Figure 3I:
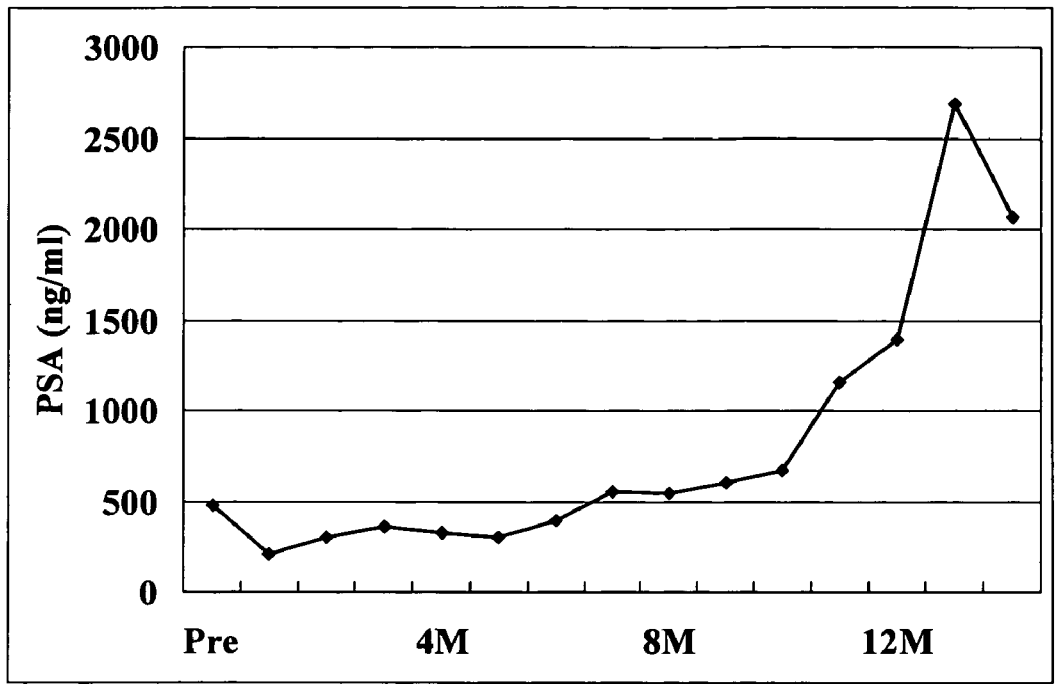
Figure 3J:
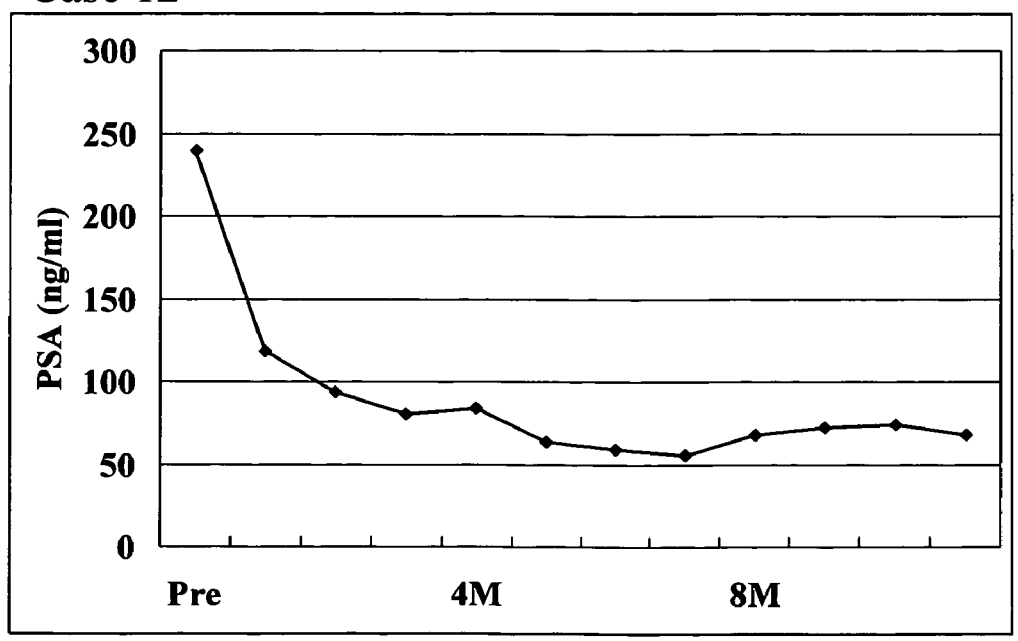
Figure 3K:
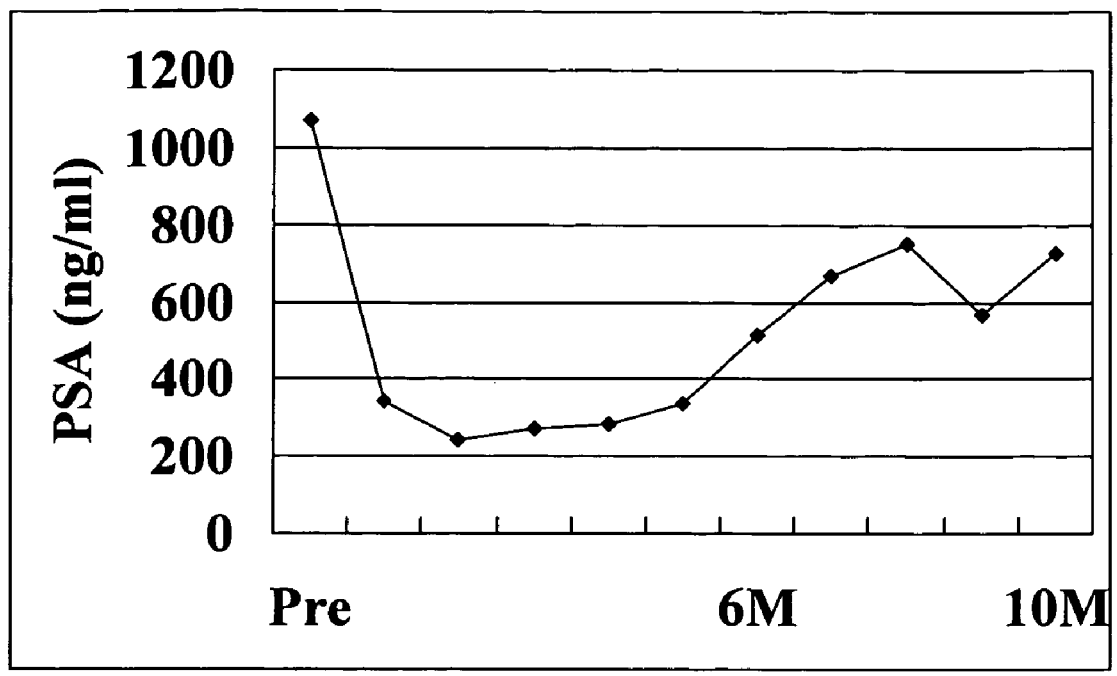

In accordance with the invention, we conducted combined peptide vaccination and estramustine phosphate treatment on patients positive for human leukocyte antigen (HLA)-A24 or A2 with metastatic hormone refractory prostate cancer (HRPC) who had failed to respond to the prior-peptide vaccination, and found that the combination therapy successfully augmented peptide-specific CTL precursors or peptide-specific IgG, and decreased serum PSA level in the patients.

In the first embodiment, the invention provides a method for treating a prostate cancer, which comprises administering a therapeutically effective amount of a cancer antigen peptide-associated agent and a lower dose of an estramustine or a salt thereof to a patient in need thereof.

Prostate cancers to be treated by the invention include a hormone-responsive prostate cancer, a hormone-refractory prostate cancer, and a hormone-insensitive prostate cancer. The present invention preferably treat or prevent a hormone-refractory prostate cancer, particularly a metastatic hormone refractory prostate cancer.

Estramustine belongs to the general group of medicines called antineoplastics, and is worldwide used to treat some cases of prostate cancer. Estramustine is a combination of estradiol with nitrogen mustard. In the invention, estramustine may be orally administered to a patient in a form of salt, which is preferably a phosphate.

The term "lower dose" as used in connection with estramustine means a dose that is lower than the usual dosage of estramustine, and specifically 140 to 560 mg/day, preferably 210 to 490 mg/day, more preferably 210 to 420 mg/day, and still more preferably 280 mg/day. The lower dose particularly includes 100 to 150 mg/day, 100 to 200 mg/day, 100 to 250 mg/day, 120 to 170 mg/day, 120 to 220 mg/day, 120 to 270 mg/day, 140 to 190 mg/day, 140 to 240 mg/day, 140 to 290 mg/day, 160 to 210 mg/day, 160 to 260 mg/day, 180 to 230 mg/day, and 180 to 280 mg/day.

The term "cancer antigen peptide-associated agent" as used herein means a tumor antigen protein and the gene thereof, a tumor antigen peptides derived from the tumor antigen protein and the gene thereof, and a derivative of their substances. Tumor antigen peptides are generated by degradation of tumor antigen proteins, which are proteins specific for tumors, in cells with proteasomes, which peptides are intracellularly synthesized. The tumor antigen peptides thus generated bind to MHC class I antigens (HLA antigens) in endoplasmic reticulum to form complexes, and the complexes are transported to the cell surface to be presented as an antigen.

Tumor antigen proteins as used herein include a protein named MAGE from human melanoma cells (*Science*, 254: 1643, 1991); melanosomal proteins such as a melanocytic tissue-specific protein, gp100 (*J. Exp. Med.*, 179:1005, 1994), MART-1 (*Proc. Natl. Acad. Sci. USA*, 91:3515, 1994), and tyrosinase (*J. Exp. Med.*, 178:489, 1993); MEGE-related proteins (*J. Exp. Med.*, 179:921, 1994); β-catenin having a tumor-specific amino acid mutation (*J. Exp. Med.*, 183:1185, 1996); and CDK4 (*Science*, 269:1281, 1995); HER2-neu (*J. Exp. Med.*, 181:2109, 1995), p53 (variant) (*Proc. Natl. Acad. Sci. USA*, 93:14704, 1996); tumor markers such as CEA (*J. Natl. Cancer Inst.*, 87:982, 1995), PSA (*J. Natl. Cancer Inst.*, 89:293, 1997); and viral proteins such as HPV (*J. Immunol.*, 154:5934, 1995) and EBV (*Int. Immunol.*, 7:653, 1995). Detailed descriptions of these substances can be found in published reviews (e.g. *Immunol. Today*, 18:267, 1997; *J. Exp. Med.*, 183:725, 1996; and *Curr. Opin. Immunol.*, 8:628, 1996).

Typical examples of tumor antigen peptides as used herein include, but not limited to, tumor antigen peptides described in WO97/46676, WO99/29715 and WO99/33977; tumor antigen peptides derived from cyclophilin B (WO99/67288); tumor antigen peptides derived from SART-1 (WO00/06595); tumor antigen peptides derived from SART-3 (WO00/12701); tumor antigen peptides derived from ART-1 (WO00/32770); tumor antigen peptides derived from SART2 (*J. Immunol.*, 164:2565, 2000); tumor antigen peptides derived from lck (*Eur. J. Immunol.*, 31:323, 2001); tumor antigen peptides derived from ART4 (*Cancer Res.*, 60:3550, 2000); and tumor antigen peptides derived from ppMAPkk, WHSC2, UBE2V, HNRPL, EIF (*Cancer Res.*, 61:2038, 2001).

Genes as used herein of a cancer antigen protein and a cancer antigen peptide can be prepared according to the well-known method such as those described in for example Molecular Cloning 2nd Edt. Cold Spring Harbor Laboratory Press (1989) with consulting the references as described above.

Derivatives as used herein of a cancer antigen protein, a cancer antigen peptide and a gene thereof mean artificial proteins and peptides that are prepared on the basis of the amino acid sequence of the cancer antigen protein and peptide, as well as genes thereof. Typical examples of derivatives include a protein and a peptide which have an amino acid sequence having a substitution, a deletion and/or an addition of a few amino acid residue in the amino acid sequence of naturally-occurring cancer antigen proteins and peptides, and which have a similar activity for inducing immunoresponses as the naturally-occurring cancer antigen proteins and peptides.

In accordance with the invention, the cancer antigen peptide-associated agent that is patient-oriented is administered. For example, in order to select patient-oriented cancer antigen peptides, cancer patients are administered with vaccine candidates comprising antigen peptides, and the ability of the vaccine candidates to induce CTLs is determined by the conventional methods [13, 14]. The cancer antigen peptide-associated agents are usually administered subcutaneously.

In the second embodiment, the invention provides a pharmaceutical composition for treating a prostate cancer which comprises a lower dose of an estramustine or a salt thereof, said composition being administered together with a cancer antigen peptide-associated agent. In another aspect, the invention provides a pharmaceutical composition for treating a prostate cancer which comprises a lower dose of an estramustine or a salt thereof, said composition augmenting CTL precursors specific for a cancer antigen peptide-associated agent, and/or augmenting immunoglobulin G specific for a cancer antigen peptide-associated agent. Meanings of the terms "prostate cancers", "estramustine", "lower dose", and "cancer antigen peptide-associated agent" are as shown above.

EXAMPLES

The present invention is further illustrated by the following examples, but is not limited by these examples in any respect.

Abbreviations as used in Examples stand for the following terms: cytotoxic T lymphocyte (CTL); peripheral blood mononuclear cells (PBMCs); human leukocyte antigen (HLA); hormone refractory-prostate cancer (HRPC); prostate-specific antigen (PSA); bone turnover marker (pyridinoline cross-linked carboxyterminal telopeptide of type I collagen: ICTP); enzyme-linked immuno-sorbent assay (ELISA); delayed-type hypersensitivity (DHT); computed tomography (CT); complete response (CR); partial response (PR); progression (PD); Armed response (Ar).

Example 1

Patients and Method

Patients

Between February, 2001 and September, 2002, 20 patients positive for human leukocyte antigen (HLA)-A24 or A2 with metastatic HRPC were entered into a phase I study in which patients were treated by peptide-specific cytotoxic T lymphocyte (CTL) precursor oriented vaccination [15]. Thirteen patients were entered in the combined peptide vaccination and estramustine phosphate treatment when the disease progressed after at least 3 peptide vaccinations in the phase I study. The disease progression was defined by at least one of three criteria: two consecutive 25% increase from baseline PSA levels at least 2 weeks apart, a greater than 25% increase in bidimensionally measurable soft tissue metastases, and the appearance of new foci on radionuclide bone scans. Serum PSA levels were determined using Tandem-R (Hybritech Inc., San Diego, Calif.) assays with a normal range between 0-4.0 ng/ml. Other eligibility included an Eastern Cooperative Oncology Group performance status of 0 or 1, age 79 years or less, granulocyte count greater than 3,000/mm$^3$, hemoglobin greater than 10 g/dl, platelets greater than 100,000/mm$^3$, bilirubin equal to or less than the institutional limit of normal, and creatinine less than 1.4 mg/dl. Negative serologic tests for hepatitis B and hepatitis C were required. Patients with a serious illness or an active secondary malignancy within the prior 5 years were excluded from the study entry. Exclusion criteria also included evidence of immunosuppression or autoimmune disease. All patients gave informed consent in accordance with institutional guidelines. This study was approved by the Kurume University School of Medicine ethics committee.

Among the 13 patients, two patients were withdrawn from the immunological and clinical evaluation because of incompletion of the intended course of therapy (6th vaccination) and there was no sample for the immunological analysis. Therefore, 11 patients were assessable for immunological and clinical evaluation. Baseline characteristics of 11 patients treated by the combination therapy are summarized in Table 1 hereinafter.

At the time of enrollment in the study, median % PABS in patients with bone metastases was 6.0 (range, 1.5 to 8.4). Prior treatments included hormonal therapy (11 patients), radiation therapy to bone metastases (2 patients), and chemotherapy with estramustine phosphate (8 patients: 5 patients were treated with estramustine alone; 3 patients were treated with estramustine plus a combination of etoposide). All 11 patients also received more than 3 (median 6, range 3 to 23 times) peptide vaccinations before the start of the combination therapy. The median duration of the combination therapy was 13 months (range, 6 to 21 months).

Patient-Oriented Peptide Vaccination

Our approach in the immunotherapy for HRPC patients is a pre-vaccination measurement of peptide-specific CTL precursors in the circulation of cancer patients reactive to 30 kinds of vaccine candidates (14 peptides for HLA-A24 positive patients, and 16 peptides for HLA-A2 positive patients) with the ability to induce CTLs, followed by administration of only reactive peptides (CTL precursor-oriented peptide vaccine) as reported previously [13-15]. The peptides used in the present study are listed in Table 2 hereinafter. These peptides were prepared under conditions of Good Manufacturing Practice by a Multiple Peptide System (San Diego, Calif.). All of these peptides have the ability to induce HLA-A24 or HLA-A2-restricted and tumor-specific CTL activity in peripheral blood mononuclear cells (PBMCs) of the cancer patients [17-23]. Before the first vaccination and 7 days after every 6th vaccination, 30 ml of peripheral blood was obtained, and PBMCs were isolated by means of Ficoll-Conray density gradient centrifugation. Peptide-specific CTL precursors in PBMCs were detected using a previously reported culture method [24]. Briefly, PBMCs (1×10$^5$ cells/well) were incubated with 10 μM of each peptide in U-bottom-type 96-well microculture plates (Nunc, Roskilde, Denmark) in 200 μl of culture medium. The culture medium contained 45% RPMI-1640 medium, 45% AIM-V™ medium (Invitrogen Corp., Carlsbad, Calif.), 10% FCS, 100 U/ml of interleukin-2 (IL-2) and 0.1 mM MEM nonessential amino acid solution (Invitrogen Corp.). Half of the medium was removed and replaced with the new medium containing a corresponding peptide (20 µM) every 3 days for up to 12 days. On the 12th day of the culture, 24 hr after the last stimulation, these cells were harvested, washed 3 times and then tested for their ability to produce IFN-$\gamma$ in response to C1R-A2402 or T2 cells preloaded with either a corresponding peptide or HIV peptide (RYLRQQLLGI (SEQ ID NO: 32)) as a negative control in HLA-A24 or HLA-A2 PBMCs, respectively. The target cells (C1R-A2402 or T2, $1\times10^4$/well) were pulsed with each peptide (10 µM) for 2 hr, and then effector cells ($1\times10^5$/well) were added to each well with the final volume of 200 µl. After incubation for 18 hr, the supernatants (100 µl) were collected, and the amounts of IFN-$\gamma$ were measured using an enzyme-linked immuno-sorbent assay (ELISA) (limit of sensitivity: 10 pg/ml). All experiments were performed in the four different wells with duplicate assays. Pre-vaccination PBMCs were provided for screening of the CTL precursors reactive to 30 peptides (14 peptides for HLA-A24 positive patients, and 16 peptides for HLA-A2 positive patients) for different wells with duplicate assays in each well, and the results of each well were classified into 4 groups in accordance with the p values (by two-tailed Students' t test) and the amounts of IFN-$\gamma$ (a mean value response to a corresponding peptide minus that to an HIV peptide) as follows: Armed response (Ar): $p\leq0.1$ and $500\leq$net; A level of response (A): $p\leq0.05$ and $50\leq$net; B: $p\leq0.05$ and $25\leq$net$<50$; C: $0.05<p\leq0.1$ and $50\leq$net. Peptides were chosen based upon evaluation of all 4 wells by the order shown above.

Combination Therapy

The peptide vaccination schedule was as follows. For the skin test, 10 µg of each selected peptide for up to 4 peptides were independently injected intradermally with a tuberculin syringe with a 27-gauge needle. Immediate- and delayed-type hypersensitivity (DHT) reactions were determined at 20 min and 24 hr after the skin test, respectively. A positive skin-test reaction was defined as >30-mm diameter erythema and induration, when saline was a negative control for assessment of the hypersensitivity. If immediate-type hypersensitivity was negative, the peptide was injected. Before the combination therapy, 3 mg/ml of each of the peptides was injected subcutaneously in the lateral thigh of each patient a total of 6 times at 2-week intervals. During the combination therapy, 1 mg/ml of each of the peptides was injected at 4- to 6-week intervals.

Estramustine phosphate was initially administered orally as 140 mg capsules, 2 capsules twice daily for a total daily dose of 560 mg for the first 2 cases, but severe immunosuppression was observed in these patients. To avoid severe immnosuppression, estramustine phosphate was reduced to 280 mg/day for the remaining 11 cases.

Immunological Monitoring

For evaluation of immune responses during the combination therapy, peptide specific CTL precursors in PBMCs and serum levels of peptide-specific antibodies were measured every 6th vaccination. Peptide-specific CTL precursors in PBMCs were detected using a previously reported culture method [24], while an ELISA was used to detect the serum IgG levels specific for the peptides administrated, as reported previously [13-15]. In addition, a new monitoring method was conducted to carefully measure the estramustine-induced immunosuppression. Namely, PBMCs were harvested every 2 weeks and were cultured ($10^4$ cells/well) for 2 days in triplicate assays with 10 µl M of phytohemagglutinin (PHA), 10 ng/ml of Epstein-Bar virus (EBV)-derived peptide with HLA-A24 or -A2 binding motif, and 10 ng/ml of two different peptides under vaccination. After 2 days in culture, the amounts of IFN-$\gamma$ in cell free supernatants were measured in triplicate assays, and viable cell numbers were also counted. To avoid biases in each assay, all the PBMCs were once cryopreserved and the four different PBMCs (two from healthy donors, one from patients PBMCs harvested 2 weeks before the latest vaccination, and one from the latest vaccination) were thawed at the same time in the morning of the experiment. The PBMCs from healthy donors were from the same donors throughout the series of immunological monitoring. Responses (IFN-$\gamma$ production) to PHA, EBV-peptide, and the vaccinated peptides were considered to be mediated by resting T cells, memory T cells, and activated T cells, respectively.

Clinical Monitoring

The patients were clinically monitored to evaluate the efficacy of the combination therapy. Specifically, the patients entered in the present trial were observed until disease death or intolerance, or consent was withdrawn. Clinical and laboratory assessments were performed at each visit, and patients were questioned about adverse events, their severity, and frequency. The severity of the adverse events was scored according to the National Cancer Institute (NCI) Toxicity Criteria. Serum PSA and bone turnover marker (pyridinoline cross-linked carboxyterminal telopeptide of type I collagen: ICTP) levels were measured every 4 weeks during the treatment. The serum levels of ICTP were measured using a two-antibody radioimmunoassay (RIA) using the Telopeptide ICTP RIA kit (Orion Diagnostica, Espoo, Finland, provided by Chugai, Tokyo, Japan). The normal range of serum ICTP was 1.8-5.0 ng/ml [25]. Bone scans and Computed tomography (CT) scans of the abdomen were performed every 3 months during this study. The metastatic findings on bone scans were assessed by the extent of the disease using the percentage of positive area on the bone scan (% PABS)[26]. Clinical response was determined by both changes in PSA levels and by imaging studies in patients with measurable disease. PSA response was defined as two consecutive measurements at least 4 weeks apart that showed a 50% or greater decrease from baseline PSA levels (PR) or normalization of the PSA level (CR). Time of PSA progression was registered at the time of the first of 2 consecutive PSA levels 25% above the baseline. Standard definitions were used for response and progression of measurable and evaluable disease. For patients with bidimensionally measurable disease, a complete response (CR) was defined as disappearance of all target lesions for at least 4 weeks; a partial response (PR) was defined as a$\geq$50% decline in bidimensionally measurable disease, and a minor response was defined as a reduction between 25% and 50%. For a response of bone metastasis, a CR was the defined as disappearance of all positive areas on bone scans. A PR was defined as a 50% or greater decrease in the % PABS, and progression (PD) was defined as an increased number of positive sites, increased intensity of the existing lesions or the 2 findings observed concurrently.

Statistical Methods

Progression-free survival was defined as the time from the beginning of the combination therapy to the time of progression for patients whose disease progressed, to the time of death for patients who died progression free, or to the time of the last contact who remain alive and progression free. Cause-specific survival was defined as the time from the beginning of the combination therapy to disease caused death. The Kaplan-Meier method was used to estimate progression-free and cause-specific survival.

Results

Immunological Response During the Combination Therapy

During the combination therapy, peptide-specific CTL precursors and peptide-specific antibodies were measured at 6-week intervals in all 11 patients. Vaccinated peptides and immune responses are summarized in Table 2 hereinafter. All 11 patients monitored for immune response during the combination therapy had either enhanced cellular or humoral responses. Augmentation of peptide-specific CTL precursors was observed in 6 of 11 patients (cases 2, 5, 7, 8, 10 and 12), while induction of peptide-specific IgG was observed in 10 of 11 patients (cases 3, 4, 5, 7, 8, 10, 11, 12 and 13). FIG. 1 demonstrates serial changes of both IFN-γ productions and IgG levels specific for the peptides administrated in each patient.

The estramustine-induced immunosuppression was also analyzed in ten of 11 patients by measurement of IFN-γ productions to PHA, EBV-peptide and the vaccinated peptides. Immunomonitoring was not carried out for case 13 because the available PBMCs were too few for use in the assay. Responses (IFN-γ productions) to PHA, EBV-peptide, and the vaccinated peptides were suggested to be mediated by resting T cells, memory T cells, and activated T cells, respectively. Results of monitoring in each case are shown in FIG. 2. Cases 2 and 3 were initially treated by the combination with a full dose (560 mg/day) of estramustine phosphate, but the immunological monitoring revealed severe immune suppression. These immune suppressions were recovered by discontinuing administration of estramustine phosphate. There was no significant immune suppression in any of 8 cases tested when the peptide and a half dose of estramustine phosphate were administrated (FIG. 2).

The results of this study suggest a benefit of combination of peptide vaccination and a low dose (280 mg/day) of estramustine phosphate in patients with metastatic HRPC. The present study demonstrated that cellular and humoral responses were well maintained in all patients with metastatic HRPC during the combination of peptide vaccination and a low-dose estramustine phosphate. The present results showed that augmentation of peptide-specific CTL precursors was observed in 6 of 11 patients and induction of peptide-specific IgG was observed in 10 of 11 patients. There was no significant immune suppression in any of 11 patients when the peptide and low dose of estramustine phosphate were administered. Further studies with a relatively large number of patients are recommended to confirm the results from this small scale study.

Clinical Response

Figure 4A:
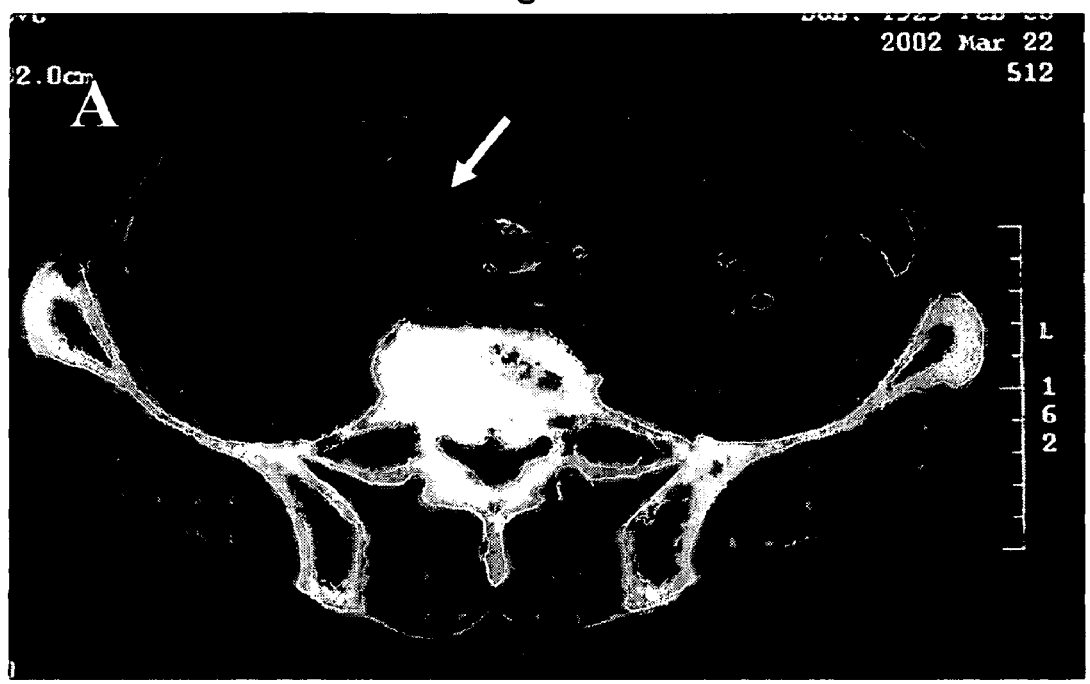
FIG. 4 shows the CT images of case 12. A: Para-aortic lymph node metastasis (arrow) was detected by a CT scan at the beginning of combination therapy. B: A repeat CT scan after 8 months with the combination therapy showed a 44% decrease in the size of lymph node metastasis (arrow).
Figure 4B:
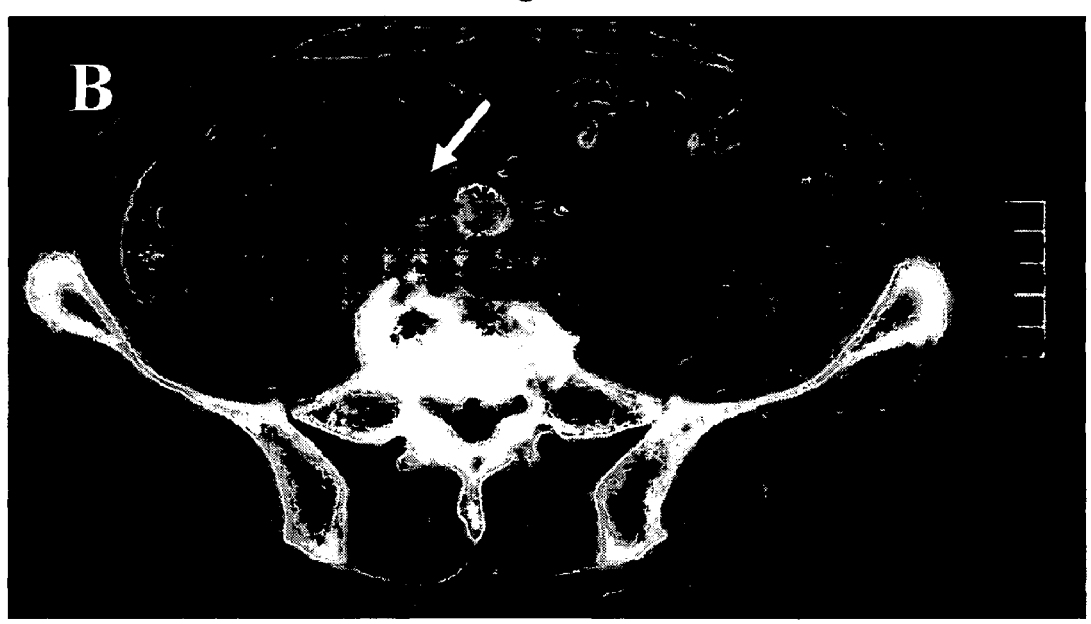
Figure 5A:
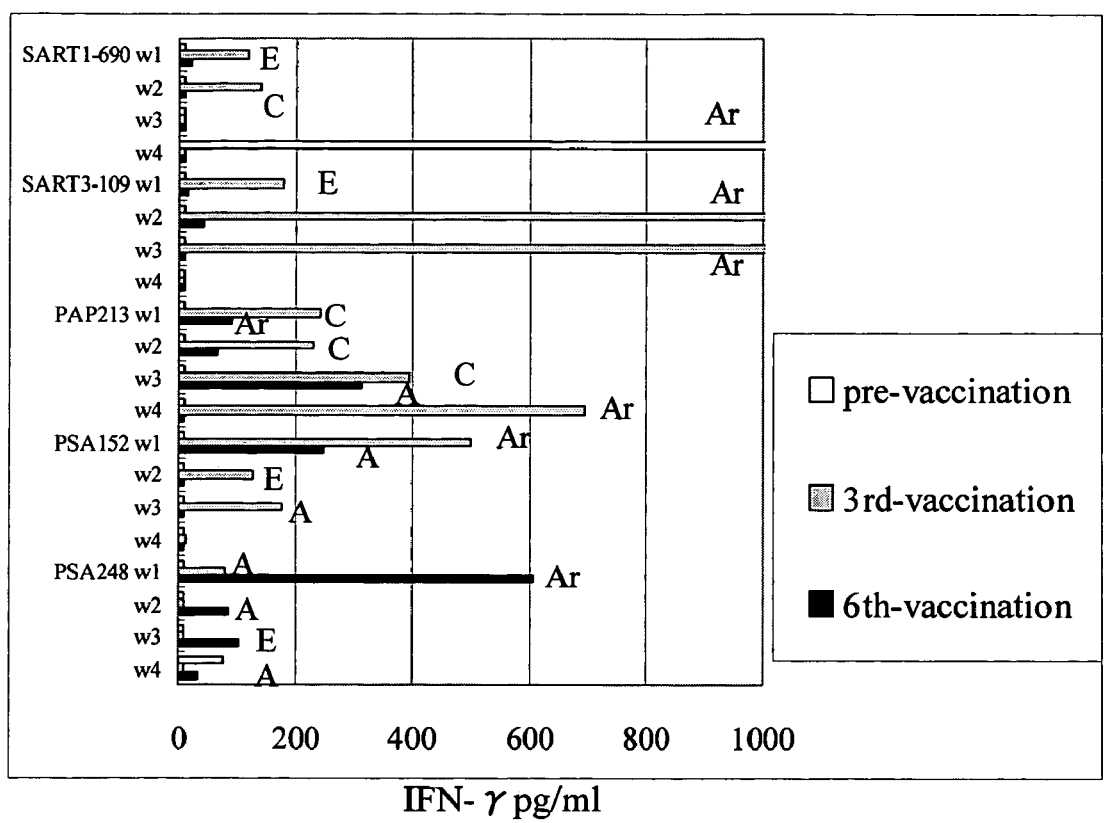
FIG. 5A to 5G depict the graphs showing the representative results of peptide-specific CTL precursors in PBMCs of pre- and post-vaccinations. Augmentation of peptide-specific CTL precursors was observed with the peptide vaccination alone, and with the combination therapy. Armed response (Ar): $p \leq 0.01$ and $500 \leq$ net value (the amount of IFN-γ in response to the corresponding peptide minus that in response to HIV peptide); A level of response (A): $p \leq 0.05$ and $50 \leq$ net; B: $p \leq 0.05$ and $25 \leq$ net $< 50$; C: $0.05 < p \leq 0.1$ and $50 \leq$ net.
Figure 5B:
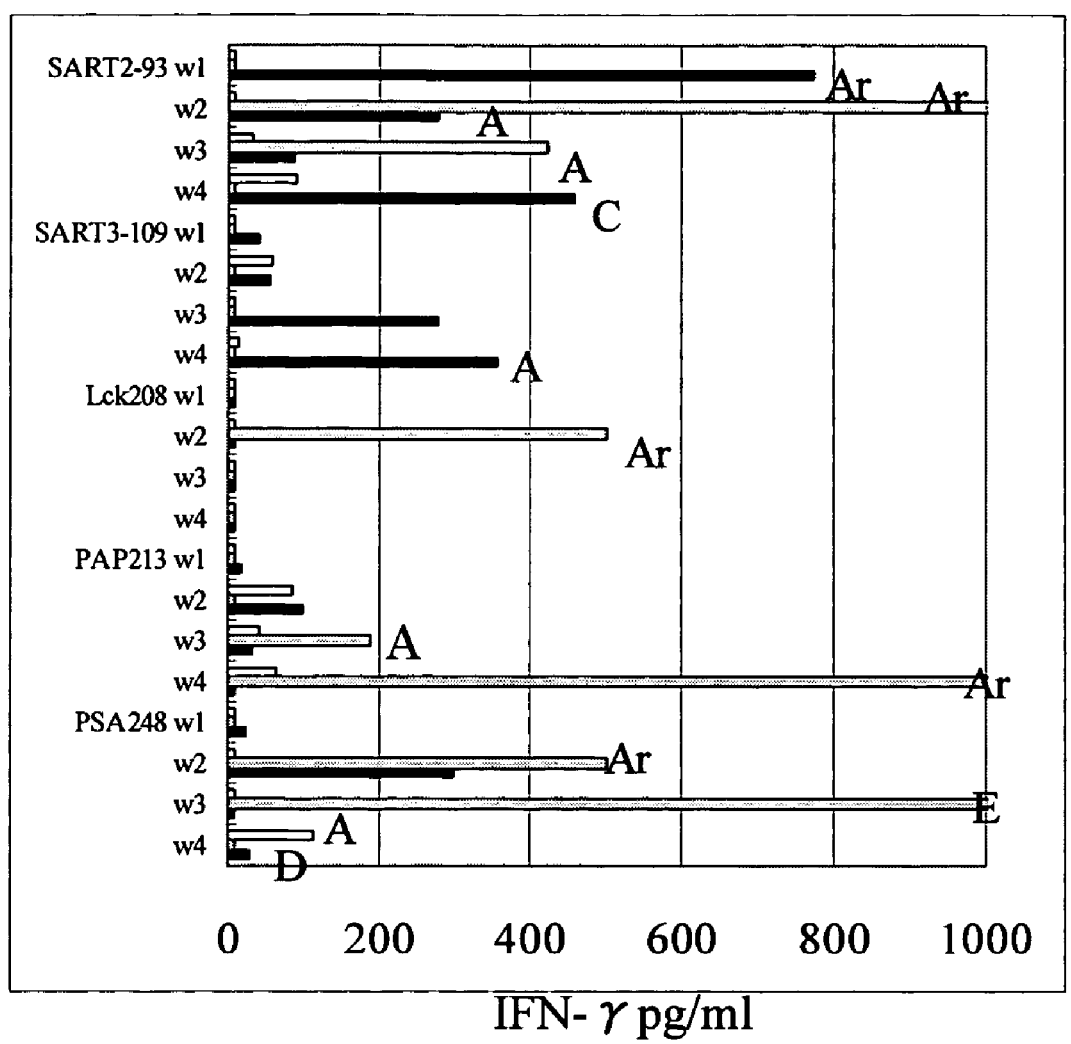
Figure 5C:
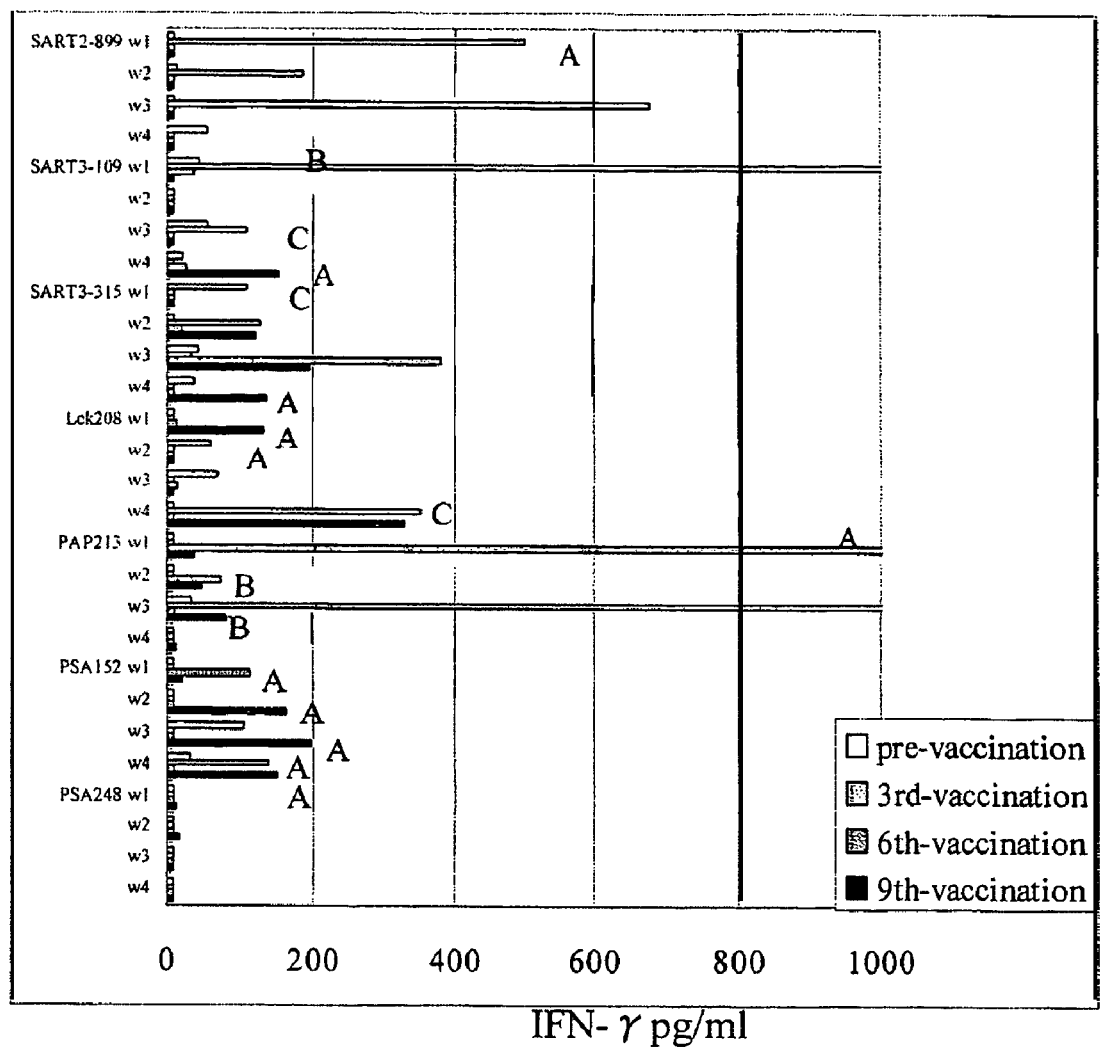
Figure 5D:
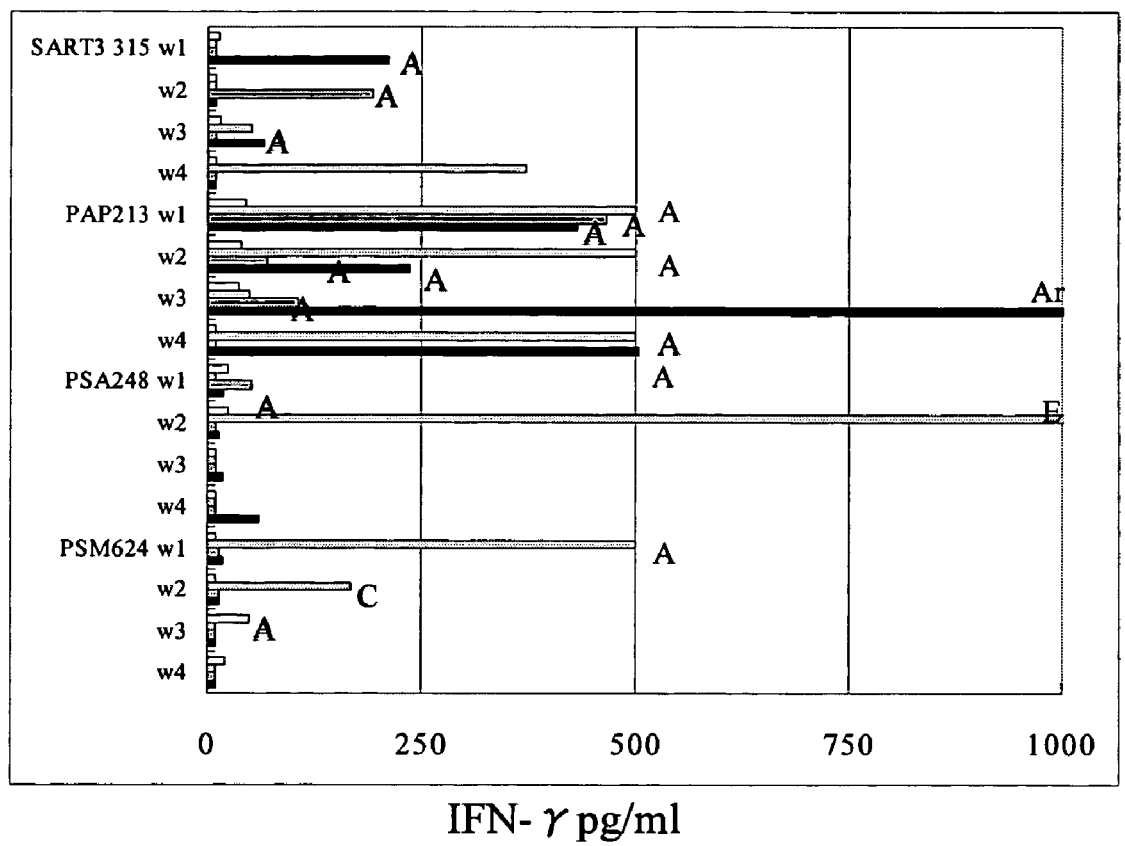
Figure 5E:
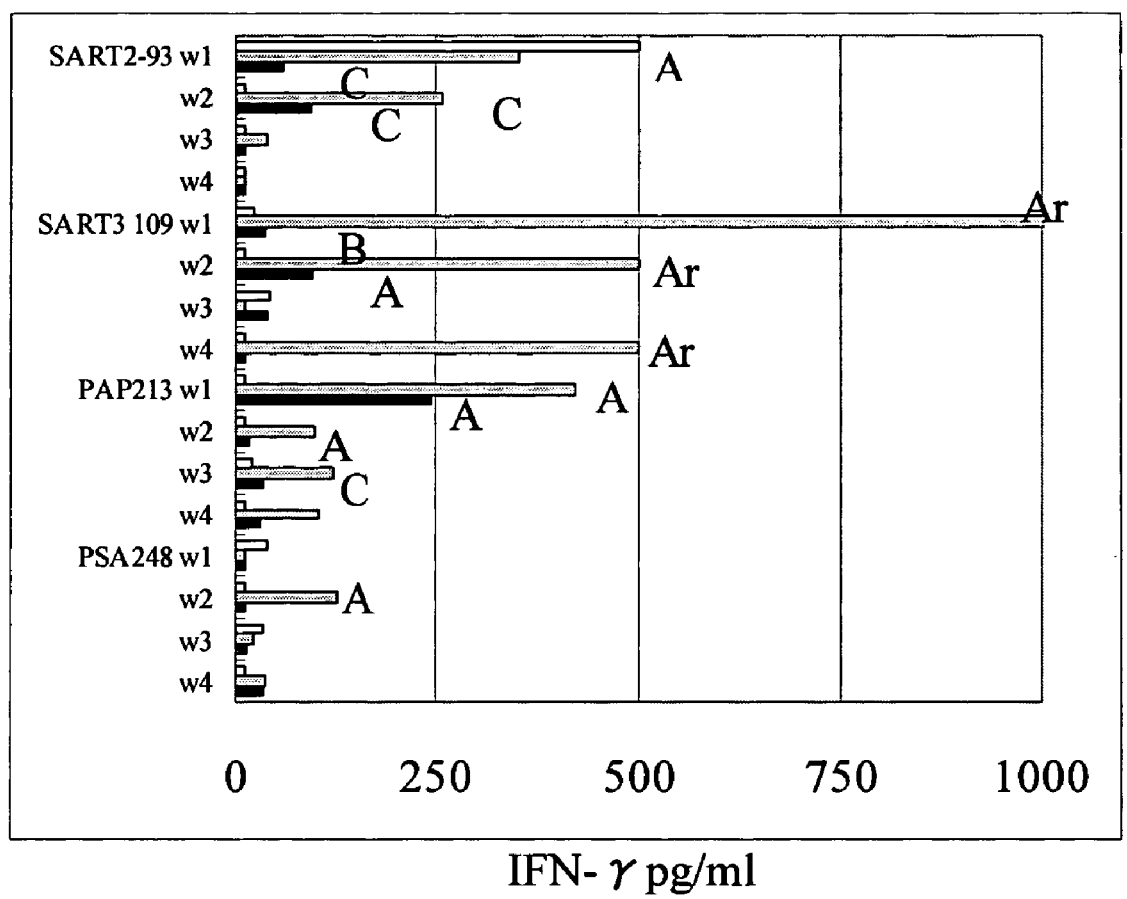
Figure 5F:
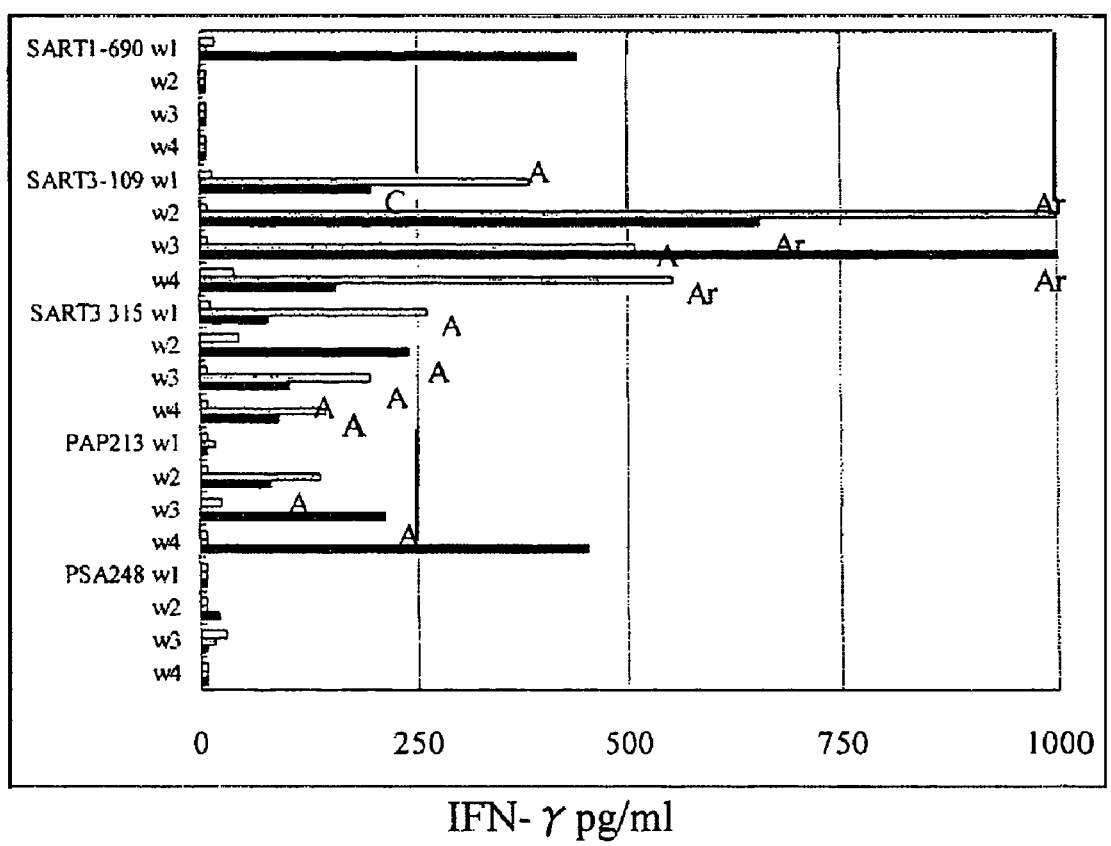
Figure 5G:
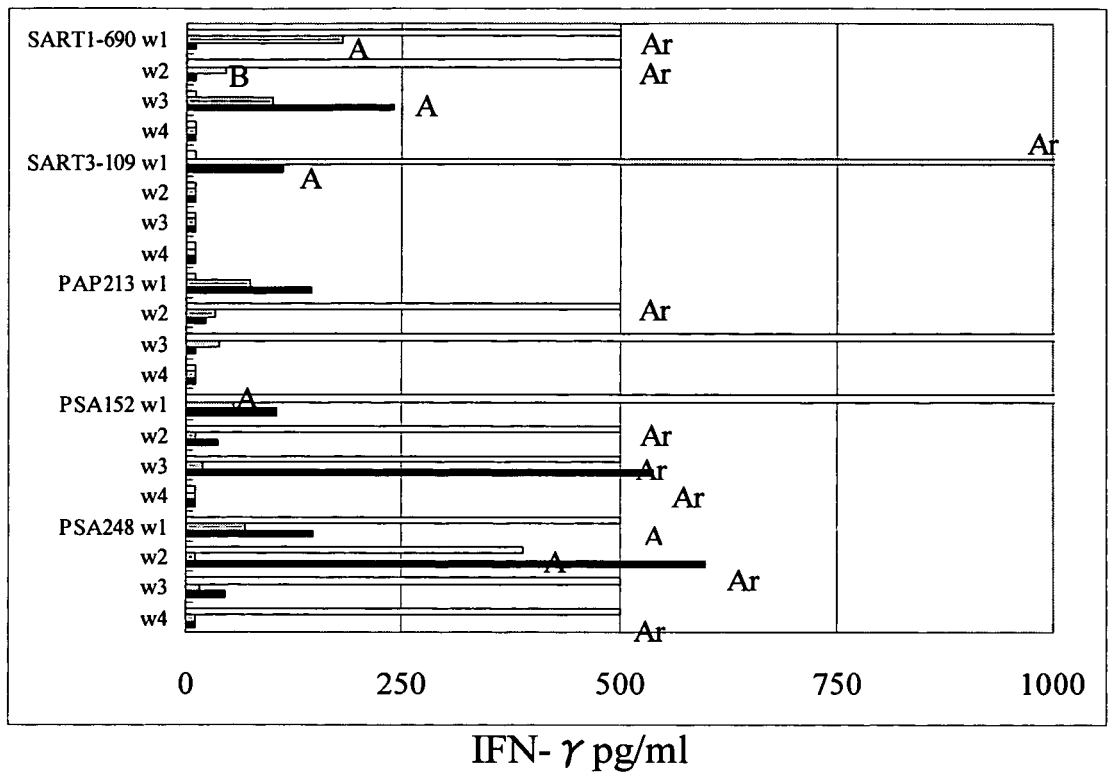
Figure 6A:
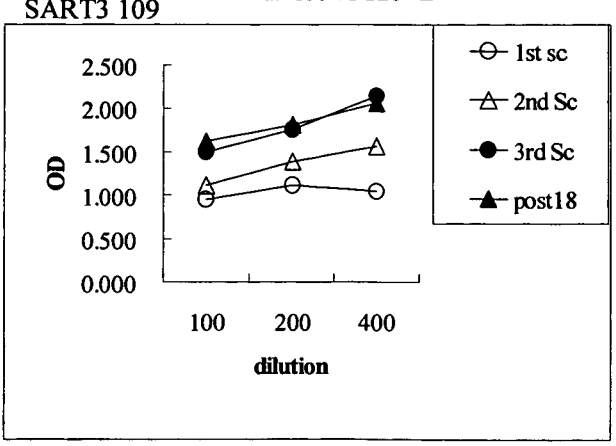
FIG. 6A to 6J depict the graphs showing the serial changes of IgG levels specific to the peptides administrated. Vertical lines indicate OD and horizontal lines indicate dilution of sera. Augmentation of peptide-specific IgG was observed with the peptide vaccination alone, and with the combination therapy. Sc: Subcutaneous injection.
Figure 6B:
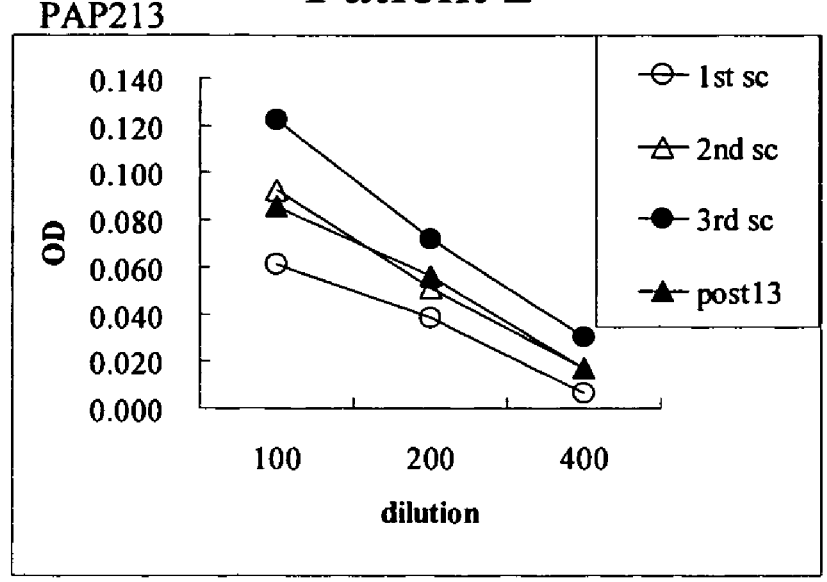
Figure 6C:
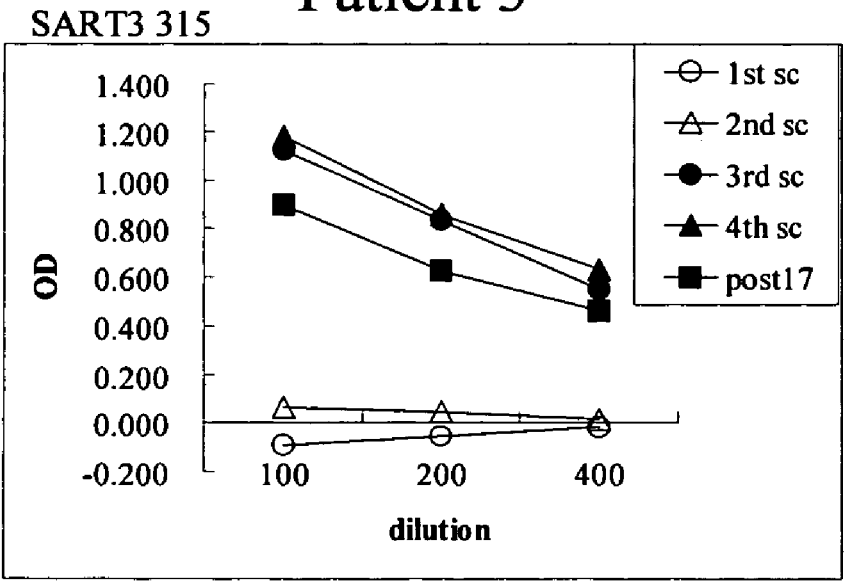
Figure 6D:
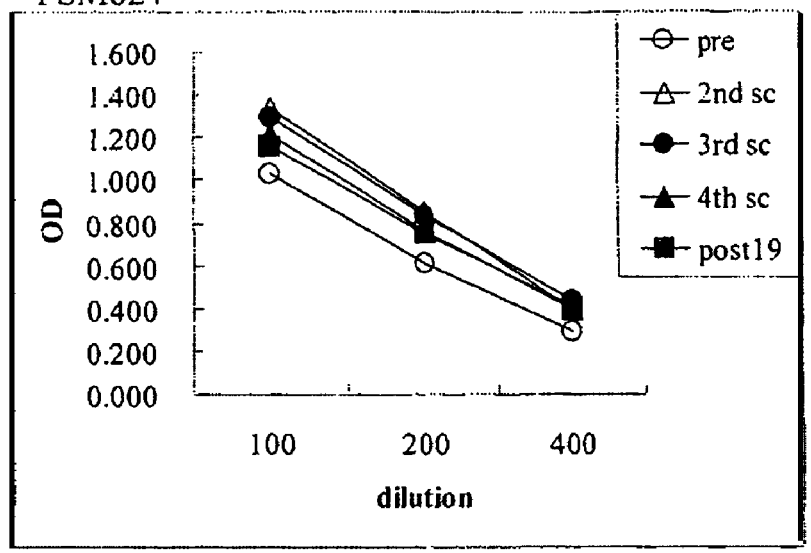
Figure 6E:
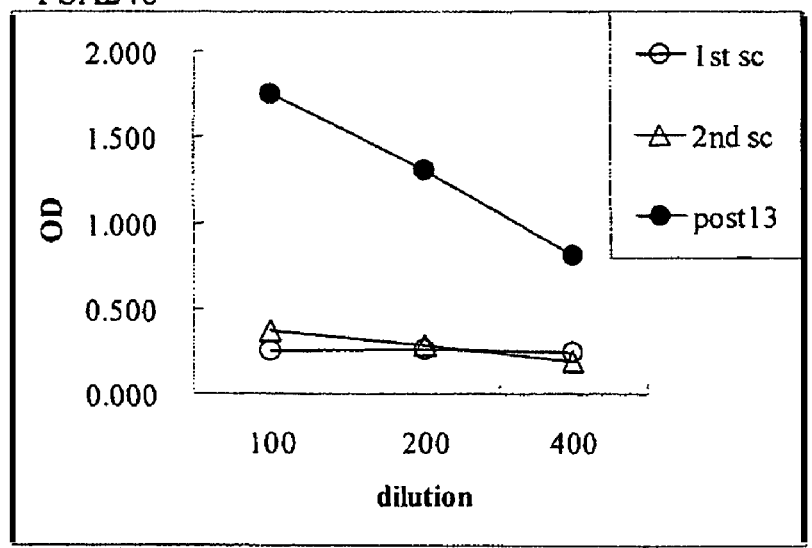
Figure 6F:
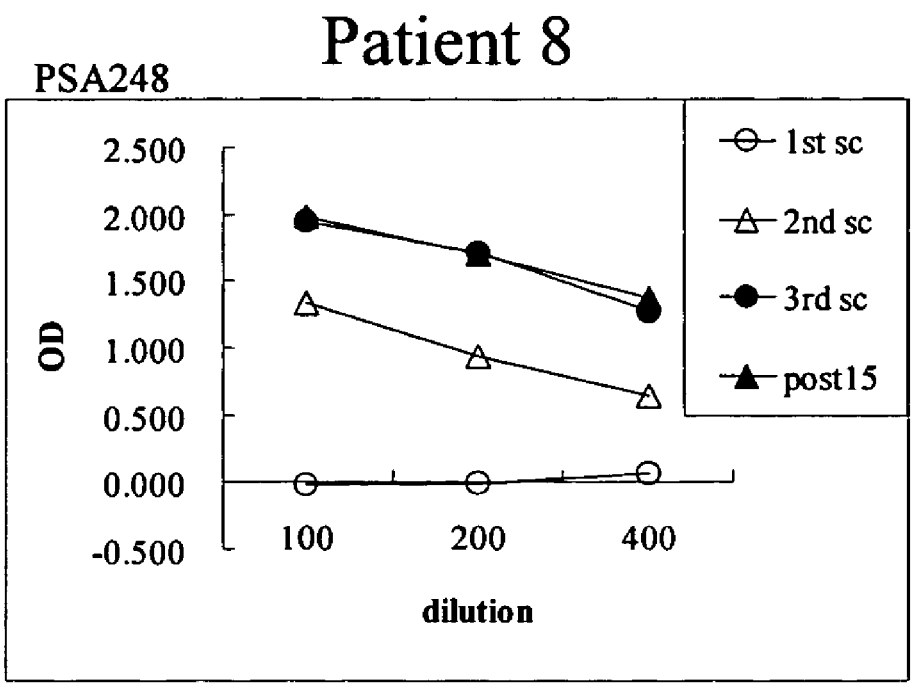
Figure 6G:
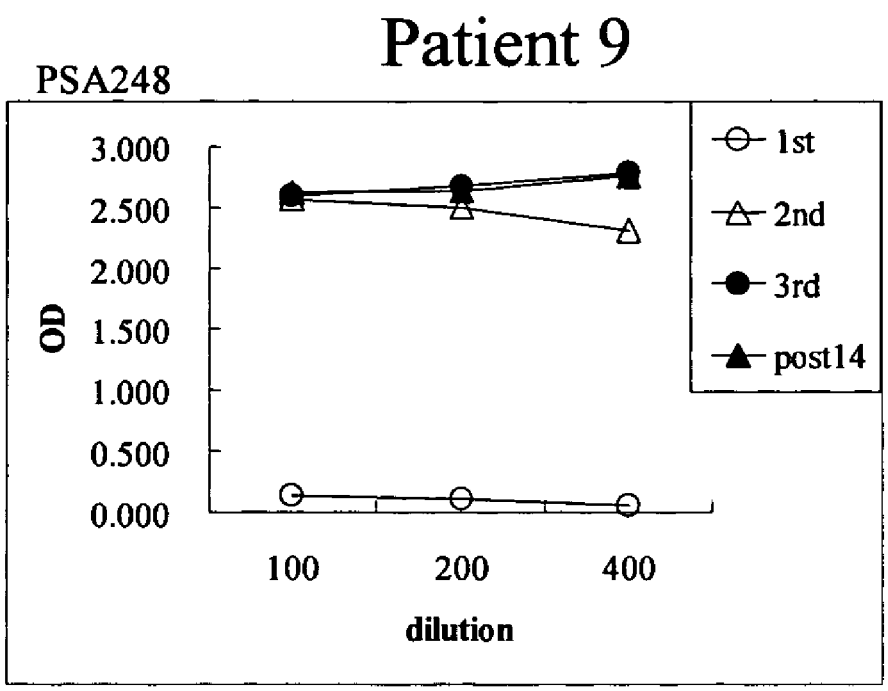
Figure 6H:
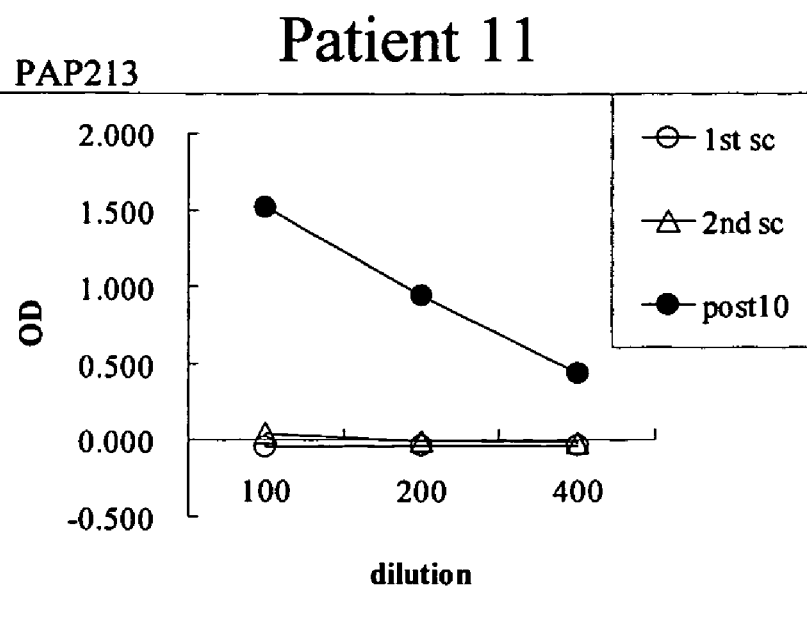
Figure 6I:
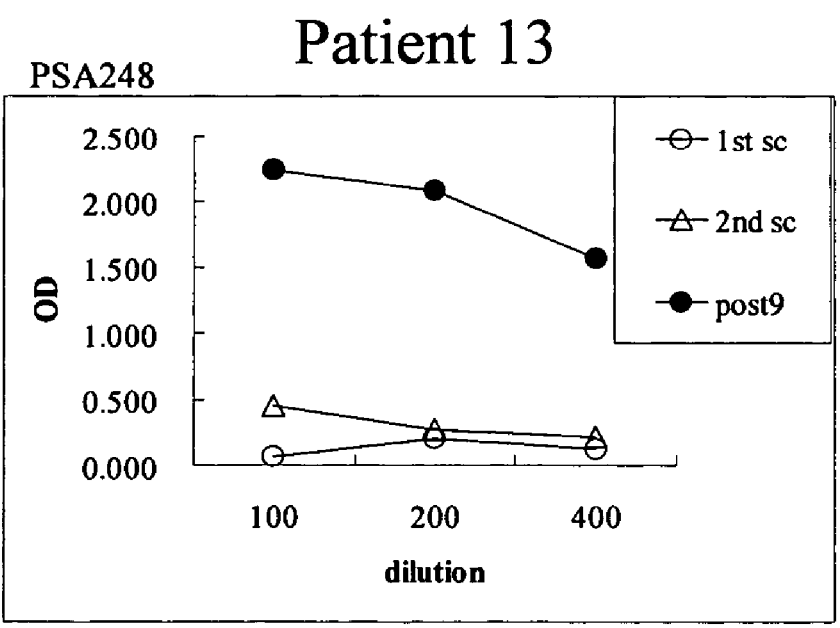
Figure 6J:
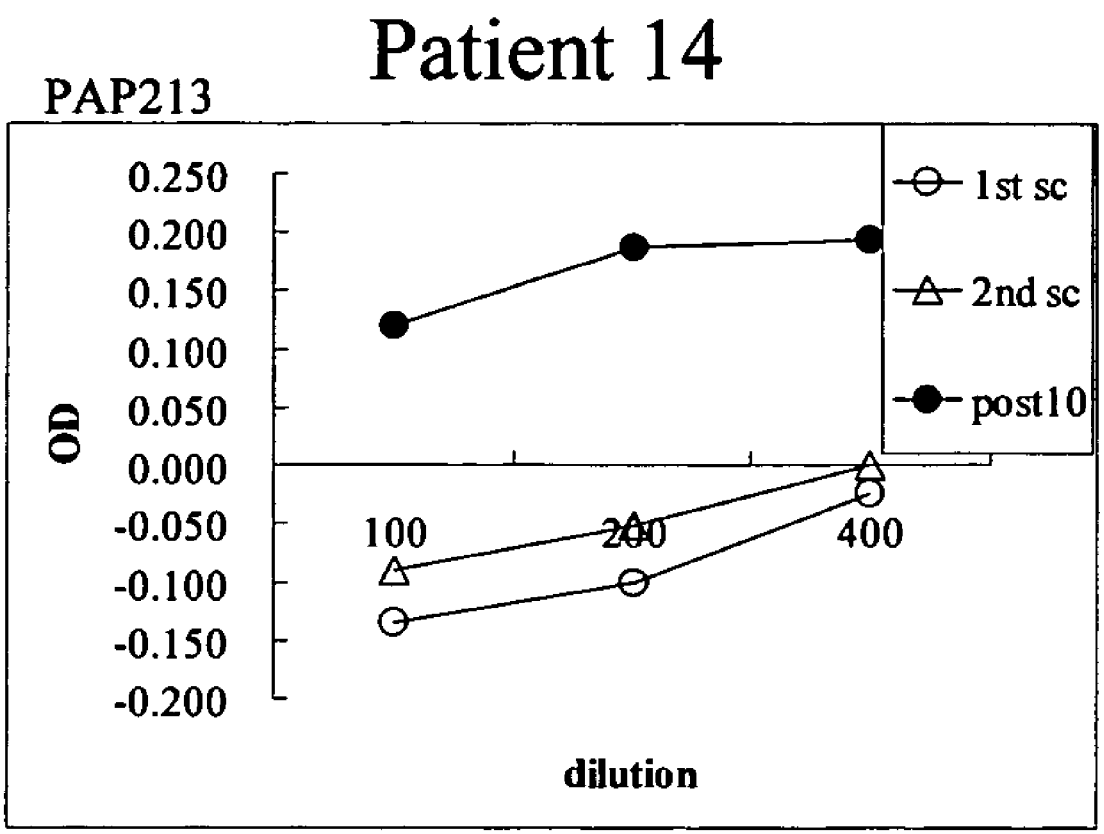
Figure 7A:
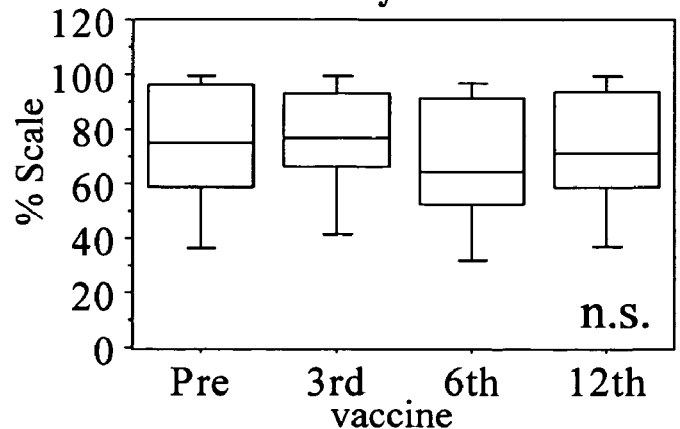
FIG. 7A to 7E depict the graphs showing the evaluation of % QOL scales during vaccination. n.s.; not significant. QOL outcome for all factors were not deteriorated during the treatment.
Figure 7B:
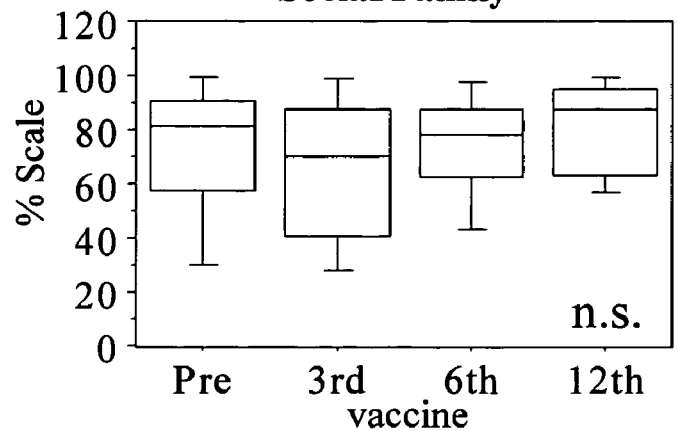
Figure 7C:
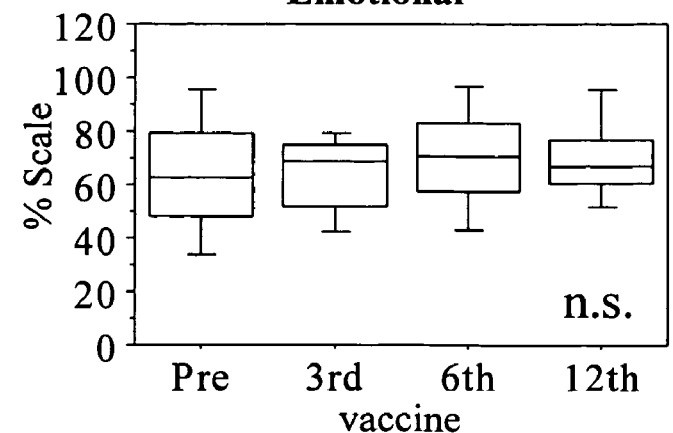
Figure 7D:
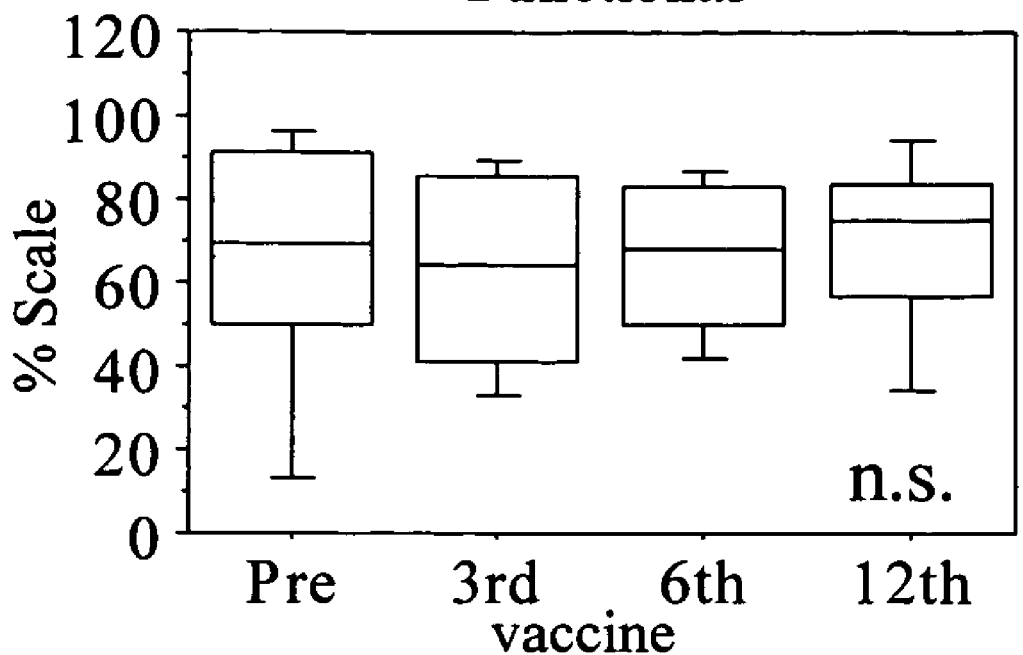
Figure 7E:
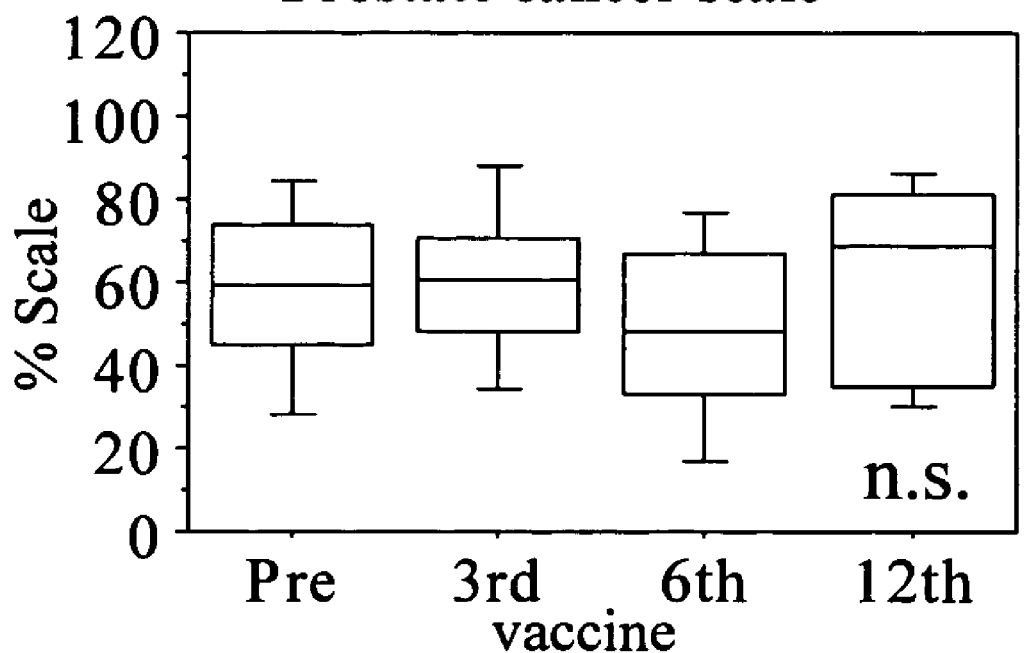

Clinical responses to the combination of peptide vaccination and oral estramustine phosphate are presented in Table 3. Ten of 11 (91%) patients showed a serum PSA level decrease from the baseline after the treatment including 8 patients (73%) who showed a serum PSA level decrease of >50%. Serial changes of PSA levels in each case during the combination therapy are shown in FIG. 3. PSA responses were noted in all 8 patients who had failed prior chemotherapy with estramustine phosphate. One of 2 patients with measurable disease showed a 44% decrease of lymph node metastasis on the CT (FIG. 4). This patient is still alive with a PSA decline of >50% (case 12). Ten patients had bone metastases. There was no improvement of bone metastases although one of 10 patients with bone metastases showed a serum ICTP level decrease of ≧50%.

At present, 3 patients have died and all deaths were attributed to prostate cancer or metastases. The median follow up for all patients was 14 months, ranging from 8 to 24 months. The median survival rate has not been calculated. At 12 months, 64% of patients were still alive.

The overall response rate (73%) defined as a serum PSA level decrease of ≧50% is significantly higher than those seen in previously reported phase I/II studies of immunotherapy such as the combination of interferon-α and interleukin-2 therapy (31%) [32] or the infusion of dendric cells primed with peptides of prostate specific membrane antigen (27%) [11, 12]. Moreover, it is also comparable with the response rate in recently reported chemotherapy trials with combinations such as estramustine and paclitaxel (53%) [6], estramustine and docetaxel (62%) [7], and the three-drug combination of estramustine, peclitaxel and carboplatin (67%) [8]. In terms of measurable disease, the overall response rate appears somewhat lower than that reported with those chemotherapy regimens because few patients in the present study had measurable soft tissue disease. Although the majority of patients showed decreased bone turnover marker (ICTP) which were proposed as a modality for monitoring bone metastasis in patients with prostate cancer with bone metastasis [33], there was no improvement of bone metastasis on bone scans. Possible explanations for this discrepancy are that bone scans are an insensitive tool or that the duration of the treatment was too short to affect the disease in bone where it can be more resistant to therapy.

Toxicity

All 13 patients were included in toxicity assessments. The toxicities reported among the 13 treated patients are summarized in Table 4. The combination therapy was safe and well tolerated with no major adverse effects in most cases, although grade 3 arrhythmia and cerebral infarction was observed in each case. One patient (case 4) developed grade 3 arrhythmia, but his arrhythmia disappeared by discontinuation of the estramustine. The other patient (case 7), who was hospitalized with grade 3 cerebral infarction after the 14-month-combination therapy, was successfully treated with anticoagulants, and was continuing the combination therapy without the other major toxicities. The most common toxicities were dermatologic reactions at the injection site of the vaccination in all cases. All 13 dermatologic reactions were scored as grade 1 or 2 using National Cancer Institute common toxicity criteria. Seven patients complained of bone pain, 4 patients developed grade 2 hematuria and 3 patients complained of fatigue. There was no treatment related hematologic, hepatic, or renal toxicity.

The toxicity of the combination regimen reported here was less and this treatment was considered acceptable in the treatment of elderly (median age 71 years) males with metastatic HRPC. The most common toxicities were dermatologic reactions at the injection site of the vaccination. Importantly, there was no hematologic toxicity nor neuropathy reported in estramustine-based or taxane-based chemotherapy regimens, and they were dose-limiting toxicities [4-8]. The common toxicities of estramustine treatment include nausea, vomiting, peripheral edema, and vascular events [16]. The combination therapy was found safe and well tolerated.

The combination of patient-oriented vaccination and low-dose estramustine phosphate was associated with a serum PSA level decrease of ≧50% in 73% of the study patients and also less toxicity in mainly elderly patients with metastatic HRPC who had received extensive prior therapy. Based on these preliminary findings, larger phase II studies of this combination are warranted.

Example 2

Patients and Method

Except for the following points, substantially the same approach was employed as Example 1.

Patients

Between March, 2002 and January, 2003, 16 patients positive for HLA-A24 with metastatic HRPC entered into the phase I/II study. Thirteen patients were followed by the combined peptide vaccination and a low dose of estramustine phosphate when the disease progressed after at least the 3rd peptide vaccination. The remaining 3 patients had only vaccine therapy because of quick disease progression to death. Table 5 summarizes the clinical characteristics for the 16 patients with HRPC in this study.

Patient-Oriented Peptide Vaccination

The following 16 peptides derived from epithelial cancer-related antigens and prostate-related antigens were used in this study: $SART1_{690-698}$ (EYRGFTQDF (SEQ ID NO: 31)), $SART2_{93-101}$ (DYSARWNEI (SEQ ID NO: 14)), $SART2_{161-169}$ (AYDFLYNYL (SEQ ID NO: 15)), $SART2_{899-907}$ (SYTRLFLIL (SEQ ID NO: 16)), $SART3_{109-118}$ (VYDYNCHVDL (SEQ ID NO: 17)), $SART3_{315-323}$ (AYIDFEMKI (SEQ ID NO: 19)), $Lck_{208-216}$ (HYTNASDGL (SEQ ID NO: 8)), $Lck_{486-494}$ (TFDYLRSVL (SEQ ID NO: 24)), $Lck_{488-497}$ (DYLRSVLEDF (SEQ ID NO: 11)), $ART1_{170-179}$ (EYCLKFTKL (SEQ ID NO: 11), prostate acid phosphate $(PAP)_{213-221}$ (LYCESVHNF (SEQ ID NO: 27)), $PSA_{152-160}$ (CYASGWGSI (SEQ ID NO: 28)), $PSA_{248-257}$ (HYRKWIKDTI (SEQ ID NO: 29)), prostate-specific membrane antigen $(PSMA)_{624-632}$ (TYSVSFDSL (SEQ ID NO: 30)), multidrug resistance-associated protein $(MRP)3_{503-511}$ (LYAWEPSFL (SEQ ID NO: 26)) and $MRP3_{1293-1302}$ (RYLTQETNKV (SEQ ID NO: 25)). All of these peptides have the ability to induce HLA-A24-restricted and tumor-specific CTL activity in PBMC on the cancer patients (15, 19, 20, 34-41). All patients were vaccinated with up to 4 peptides selected from the 16 candidates by pre-vaccination measurements.

Combination Therapy

Estramustine phosphate was administered orally as a 140 mg. capsule, 1 capsule twice daily, for a total daily dose of 280 mg to avoid severe immunosuppression in the combination therapy.

Clinical Monitoring

QOL outcome of patients during this treatment were also evaluated at pre-vaccination, and 3rd, 6th, and 12th vaccination using a Japanese version of the Functional Assessment of Cancer Therapy (FACT-P) subscale, FACT-P (for prostate cancer) (42). The FACT-P questionnaire consists of 5 factors including physical well being (7 items), social/family well being (8 items), emotional well being (6 items), functional well being (7 items) and prostate cancer scale (12 items). QOL outcomes were separately assessed by the percentage of each scale.

Results

Immunological Response During the Combination Therapy

Before the peptide vaccination, peptide-specific CTL precursors were examined, and were detectable in 14 of 16 patients with a median positive number of 1.5 peptides (range, 0-4 peptides) per patient (Table 6). In addition, anti-peptide IgGs were also detectable in 14 of 16 patients with a median positive number of 3 peptides (0-4 peptides) per patient. Four peptides at maximum were selected for the injection to each patient and the results of the selection were listed in Table 6. The most frequently selected peptide was $PSA_{248-257}$ (13/16), followed by $PAP_{213-221}$ (11/16), $SART3_{109-118}$ (11/16), $SART3_{315-323}$ (6/16), $PSA_{152-160}$ (5/16), $Lck_{488-497}$ (5/16), $SART1_{690-698}$ (3/16), $SART2_{93-101}$ (3/16), and $Lck_{208-216}$ (3/16). $PSMA_{624-628}$ and $SART2_{161-169}$ were selected in each patient, while the remaining 5 peptides derived from SART2, Lck, ART1 and MRP3 were not selected in these patients. Augmentation of peptide-specific CTL precursors or peptide-specific IgG was observed in 10 of 14 or 7 of 14 patients at 12 weeks (peptide vaccination alone), and in 6 of 8 or 10 of 12 patients at 24 weeks (during the combination therapy), respectively. Representative results of peptide-specific CTL precursors in PBMCs are shown in FIG. 5. FIG. 6 demonstrates serial changes of IgG levels specific for the peptides administrated in each patient. DTH response was observed in 4 of 16 patients, and a summary is presented in Table 6.

There was no significant immunosuppression in most cases when the peptide and a half dose (280 mg/day) of estramustine were administrated.

Clinical Response

Among the 16 patients, two patients had rapid tumor progression before the combination therapy, and the remaining one patient withdrew his consent from combination therapy after a serum PSA level decrease of ≧50% with vaccination alone. The remaining 13 patients received the combination of vaccinations and a low dose of estramustine phosphate, and were evaluated for clinical responses. All 13 patients showed a serum PSA level decrease from the baseline after the combination therapy, and 6 of 13 (46%) patients showed a serum PSA level decrease of ≧50% with a median duration of 7.5 months (range, 3-13 months). However, none of these 13 patients had objective response to treatment.

For patients with advanced disease who have reduced life expectancy and no immediate hope for a cure, relief of physical symptoms and maintenance of function become primary objectives of medical intervention [43]. In this study, QOL outcomes of 16 patients during this treatment were evaluated at pre-vaccination (16 patients), and 3rd (16 patients), 6th (13 patients), and 12th vaccination (7 patients) using a Japanese version of questionnaire of the FACT-P. FIG. 7 shows an average percentage of scales for each factor at the measuring point. QOL outcomes for all factors were not deteriorated during the treatment.

Toxicity

All 16 patients were evaluated for all common toxicities, and the over all toxicities are shown in table 7. The toxicity of the combination regimen reported here was tolerable and this treatment was considered acceptable in the treatment on the vast majority of metastatic HRPC.

Example 3

As shown in example 1, sever immunosuppression was observed with a full dose (560 mg/day) of estramustine phosphate. Table 8 summarizes the results of the combination therapy according to the present invention in view of the dose of estramustine phosphate. In the combination therapy using 280 mg/day (maximum non-immunosuppressive dose) of estramustine phosphate, an augmentation of the immunological response and an improvement of the clinical response were observed in HRPC patients who had showed disease progression with peptide vaccination alone. These results support an advantageous effect of combination of a low dose of estramustine and peptide vaccination.

Example 4

Table 9 also demonstrates the superior effects of the present combination therapy compared to previous therapies. All cases had not responded to prior estramustine phosphate therapy, and their diseases progressed after vaccination alone (PD). With the combination therapy, the clinical responses were improved to PR (partial response) or SD (stable disease) in most cases, and survival of patients with HRPC was remarkably prolonged (Median survival time: 25 months).

Discussion

Defining the expression of tumor antigens on prostate cancers of different stages is the crucial first step in selecting targets for specific immunotherapy [28-30]. The present approach in immunotherapy for HRPC patients used a new strategy of a pre-vaccination measurement of peptide-specific CTL precursors in the circulation of cancer patients, followed by administration of up to 4 peptides that had been reactive for pre-vaccination measurement among vaccine candidates (patient-oriented vaccination). Previous results from a phase I study demonstrated that patient-oriented vaccination is feasible, safe and immunologically active but the clinical response has been largely limited [15]. It has been known for some time that the malignant transformation of cells is associated with altered HLA class I expression and/or function, and that these abnormalities can provide tumor cells with avenues of escape from immune recognition. In contrast to the normal HLA class I expression of the benign tissue, complete loss of HLA class I expression was reported in 34% of primary prostate cancer cells and 80% of prostate cancer cells of lymph node metastases [31]. Therefore, HLA class I antigen down-regulation in prostate cancer may have a negative impact on the outcome of T-cell-based immunotherapy because they provide malignant cells with a mechanism by which to escape T-cell recognition. It is suggested that additive anti-tumor effects could be achieved by the combination of T-cell-based immunotherapy and cytotoxic agents with minimum immunosuppression. In the present study, PSA responses were observed in patients who experienced disease progression prior to estramustine phosphate or peptide vaccination, supporting the hypothesis that this combination works by additive anti-tumor effects. However, the exact mechanism of this interaction is unclear. Further studies on this mechanism are needed.

REFERENCES

1. Tannock I F, Osoba D, Stockler M R, Ernst D S, Neville A J, Moore M J, Armitage G R, Wilson J J, Venner P M, Coppin C M, Murphy K C. Chemotherapy with mitxantrone plus prednisone or prednisone alone for symptomatic hormone-resistant prostate cancer: A Canadian randomized trial with palliative end points. J Clin Oncol 1996; 14: 1756-1764.
2. Kantoff P W, Halabi S, Conaway M, Picus J, Kirshner J, Hars V, Trump D, Winer E P, Vogelzang N J. Hydrocortisone with or without mitoxantrone in men with hormone-refractory prostate cancer: Results of the cancer and leukemia group B 9182 study. J Clin Oncol 1999; 17: 2506-2513.
3. Hudes G, Einhorn L, Ross E, Balsham A, Loehrer P, Ramsey H, Sprandio J, Entmacher M, Dugan W, Ansari R. Monaco F. Hanna M, Roth B. Vinblastine versus vinblastine plus oral estramustine phosphate for patients with hormone-refractory prostate cancer: a Hoosier Oncology Group and Fox Chase Network phase III trial. J Clin Oncol 1999; 17: 3160-3166.
4. Smith D C, Esper P, Strawderman M, Redman B, Pienta K J. Phase II trial of oral estramustine, oral etoposide, and intravenous paclitaxel in hormone-refractory prostate cancer. J Clin Oncol 1999; 17: 1664-1671.
5. Beer T M, Pierce W C, Lowe B A, Henner W D. Phase II study of weekly docetaxel in symptomatic androgen-independent prostate cancer. Ann Oncol 2001; 12: 1273-1279.
6. Hudes G R, Nathan F, Khater C, Haas N, Cornfield M, Giantonio B, Greenberg R, Gomella L, Litwin S, Ross E, Roethke S, McAleer C. Phase II trial of 96-hour paclitaxel plus oral estramustine phosphate in metastatic hormone-refractory prostate cancer. J Clin Oncol 1997; 15: 3156-3163.
7. Ellerhorst J A, Tu S M, Amato R J, Finn L, Millikan R E, Pagliaro L C, Jackson A, Logothetis C J. et al: Phase II trial of alternating weekly chemohormonal therapy for patients with androgen-independent prostate cancer. Clin Cancer Res 1997; 3: 2371-2376.
8. Kelly W K, Curley T, Slovin S, Heller G, McCaffrey J, Bajorin D, Ciolino A, Regan K, Schwartz M, Kantoff P, George D, Oh W, Smith M, Kaufman D, Small E J, Schwartz L, Larson S, Tong W, Scher H. Paclitaxel, estramustine phosphate, and carboplatin in patients with advanced prostate cancer. J Clin Oncol 2001; 19: 44-53.
9. van der Bruggen P, Traversari C, Chomez P, Lurquin C, De Plaen E, Van den Eynde B, Knuth A, Boon T. A gene encoding an antigen recognized by cytolytic T lymphocytes on a human melanoma. Science 1991; 254:1643-1647.
10. Kawakami Y, Eliyahu S, Sakaguchi K, Robbins P F, Rivoltini L, Yannelli J R, Appella E, Rosenberg S A. Identification of the immunodominant peptides of the MART-1 human melanoma antigen recognized by the majority of HLA-A2-restricted tumor infiltrating lymphocytes. J Exp Med 1994; 180: 347-352.
11. Tjoa B A, Simmons S J, Bowes V A, Ragde H, Rogers M, Elgamal A, Kenny G M, Cobb O E, Ireton R C, Troychak M J, Salgaller M L, Boynton A L, Murphy GP. Evaluation of phase I/II clinical trials in prostate cancer with dendritic cells and PSMA peptides. Prostate 1998; 36: 39-44.
12. Salgaller M L, Lodge P A, McLean J G, Tjoa B A, Loftus D J, Ragde H, Kenny G M, Rogers M, Boynton A L, Murphy G P. Report of immune monitoring of prostate cancer patients undergoing T-cell therapy using dendritic cells pulsed with HLA-A2-specific peptides from prostate-specific membrane antigen (PSMA). Prostate 1998; 35: 144-151.
13. Mine T, Gouhara R, Hida N, Imai N, Azuma K, Rikimaru T, Katagiri K, Nishikori Misa, Sukehiro A, Nakagawa M, Yamada A, Aizawa H, Shirozu K, Itoh K, and Yamana H. Immunological evaluation of CTL precursor-oriented vaccine for advanced lung cancer patients. Cancer Sci 2003; 94: 548-556.
14. Tanaka S, Harada M, Mine T, Noguchi M, Gohara R, Azuma K, Yamada A, Morinaga A, Nishikori M, Katagiri K, Itoh K, Yamana H and Hashimoto T.: Peptide vaccination for patients with melanoma and other types of cancers based on pre-existing peptide-specific cytotoxic T lymphocyte precursors in periphery. J Immunother (in press)

15. Noguchi M, Kobayashi K, Suetugu N, Tomiyasu K, Suekane S, Yamada A, Itoh K, Noda S. Induction of cellular and humoral immune responses to tumor cells and peptides in HLA-A24 positive hormone-refractory prostate cancer patients by peptide vaccination. Prostate (in press)
16. Perry C A and McTavish D. Estramustine phosphate sodium. A review of its pharmacodynamic and pharmacokinetic properties, and therapeutic efficacy in prostate cancer. Drugs and Aging 1995; 7: 49-74.
17. Shichijo S, Nakao M, Imai Y, Takasu H, Kawamoto M, Niiya F, Yang D, Toh Y, Yamana H, Itoh K. A gene encoding antigenic peptides of human squamous cell carcinoma recognized by cytotoxic T lymphocytes. J Exp Med 1998; 187: 277-288.
18. Nakao M, Shichijo S, Imaizumi T, Inoue Y, Matsunaga K, Yamada A, Kikuchi M, Tsuda N, Ohta K, Takamori S, Yamana H, Fujita H, Itoh K. Identification of gene coding for a new squamous cell carcinoma antigen recognized by the CTLs. J Immunol 2000; 164: 2565-2574.
19. Yang D, Nakao M, Shichijo S, Sasatomi T, Takasu H, Matsumoto H, Mori K, Hayashi A, Yamana H, Shirouzu K, Itoh K. Identification of a gene coding for a protein possessing shared tumor epitopes capable of inducing HLA-A24-restructed cytotoxic T lymphocytes in cancer patients. Cancer Res 1999; 59: 4056-4063.
20. Gomi S, Nakao M, Niiya F, Imamura Y, Kawano K, Nishizaka S, Hayashi A, Sobao Y, Oizumi K, Itoh K. A cyclophilin B gene encodes antigenic epitopes recognized by HLA-A24-restricted and tumor-specific cytotoxic T lymphocytes. J Immunol 1999; 163: 4994-5004.
21. Maeda Y, Ito M, Harashima N, Nakatsura T, Hida N, Imai N, Sato Y, Shichijo S, Todo S, Itoh K. Cleavage and polyadenylation specificity factor (CPSF)-derived peptides can induce HLA-A2-restricted and tumor-specific CTLs in the majority of gastrointestinal cancer patients. Int J Cancer 2002; 99: 409-417.
22. Suzuki N, Maeda Y, Tanaka S, Hida N, Mine T, Yamamoto K, Oka M, Itoh K. Detection of peptide-specific cytotoxic T lymphocyte precursors used for specific immunotherapy of pancreatic cancer. Int J Cancer 2002; 98: 45-50.
23. Miyagi Y, Imai N, Sasatomi T, Yamada A, Mine T, Katagiri K, Nakagawa M, Muto A, Okouchi S, Isomoto H, Shirouzu K, Yamana H, Itoh K. Induction of cellular immune response to tumor cells and peptides in colorectal cancer patients by vaccination with SART3 peptides. Clin Cancer Res 2001; 7: 3950-3962.
24. Hida N, Maeda Y, Katagiri K, Takasu H, Harada M, Itoh K. A simple culture protocol to detect peptide-specific cytotoxic T lymphocyte precursors in circulation. Cancer Immunol Immunotherapy 2002; 51: 219-228.
25. Noguchi M and Noda S: Pyridinoline cross-linked carboxyterminal telopeptide of type I collagen as a useful marker for monitoring metastatic bone activity in men with prostate cancer. J Urol 2001; 166: 1106-1110.
26. Noguchi M, Kikuchi H, Ishibashi M, Noda S. Percentage of the positive area of bone metastasis is an independent predictor of the disease death in advanced prostate cancer. Br J Cancer 2003; 88: 195-201.
27. Mitcell M S. Chemotherapy in combination with biomodulation: a 5 year experience with cyclophosphamide and IL-2. Semin Oncol 1992; 19 (suppl 2): 80-87.
28. Zhang S, Cordon-Cardo C, Zhang H S, Reuter V E, Adluri S, Hamilton W B, Lloyd K O, and Livingston P O. Selection of tumor antigens as targets for immune attack using immunohistochemistry. I. Focus on gangliosides. Int J Cancer 1997; 73: 42-49.
29. Zhang S, Zhang H S, Cordon-Cardo C, Reuter V E, Singhal A K, Lloyd K O, and Livingston P O. Selection of tumor antigens as targets for immune attack using immunohistochemistry. II. Blood group-related antigens. Int J Cancer 1997; 73: 50-56.
30. Zhang S, Zhang H S, Reuter V E, Slovin S F, Scher H I, Livingston PO. Expression of potential target antigens for immunotherapy on primary and metastatic prostate cancers. Clin Cancer Res 1998; 4: 295-302.
31. Blades R A, Keating P J, McWilliam L J, George N J, Stern P L. Loss of HLA class I expression in prostate cancer: implications for immunotherapy. Urology 1995; 46: 681-687.
32. Maffezzini M, Simonato A, Fortis C. Salvage immunotherapy with subcutaneous recombination interleukin 2 (rIL-2) and alpha-interferon (A-INF) for stage D3 prostate carcinoma failing second-line hormonal treatment. Prostate 1996; 28: 282-286.
33. Noguchi M, Yahara J, and Noda S: Serum levels of bone turnover markers parallel the results of bone scintigraphy in monitoring bone activity of prostate cancer. Urology 2003; 61: 993-998.
34. Noguchi M, Itoh K, Suekane S, Yao A, Suetsugu N, Katagiri K, Yamada A, Yamana H, and Noda S. Phase I trial of patient-oriented vaccination in HLA-A2 positive patients with metastatic hormone refractory prostate cancer. Cancer Sci 2004; 95:77-84.
35. Noguchi M, Itoh K, Suekane S, Morinaga A, Sukehiro A, Suetsugu N, Katagiri K, Yamada A, and Noda S. Immunological Monitoring during Combination of Patient-Oriented Peptide Vaccination and Estramustine Phosphate in Patients with Metastatic Hormone Refractory Prostate Cancer. Prostate 2004; 60:32-45.
36. Inoue Y, Takaue Y, Takei M, Kato K, Kanai S, Harada Y, Tobisu K, Noguchi M, Kakizoe T, Itoh K, and Wakasugi H. Induction of tumor specific cytotoxic T lymphocytes in prostate cancer using prostatic acid phosphatase derived HLA-A2402 binding peptide. J Urol 2001; 166:1508-1513.
37. Harada M, Kobayashi K, Matsueda S, Nakagawa M, Noguchi M, and Itoh K. Prostate-specific antigen-derived epitopes capable of inducing cellular and humoral responses in HLA-A24+ prostate cancer patients. Prostate 2003; 57:152-159.
38. Kobayashi K, Noguchi M, Itoh K, and Harada M. Identification of a prostate-specific membrane antigen-derived peptide capable of eliciting both cellular and humoral immune responses in HLA-A24+ prostate cancer patients. Cancer Sci 2003; 94:622-627.
39. Harada M, Noguchi M, Itoh K. Target molecules in specific immunotherapy against prostate cancer. Int J Clin Oncol 2003; 8: 193-199.
40. Harashima N, Tanaka K, Sasatomi T, Shimizu K, Miyagi Y, Yamada A, Tamura M, Yamana H, Itoh K, and Shichijo S. Recognition of the Lck tyrosine kinase as a tumor antigen by cytotoxic T lymphocytes of cancer patients with distant metastases. Eur J Immunol 2000; 31:323-332.
41. Kawano K, Gomi S, Tanaka K, Tsuda N, Kamura T, Itoh K, and Yamada A. Identification of a new endoplasmic reticulum-resident proteine recognized by HLA-A-24 restricted tumor infiltrating lymphocytes of lung cancer. Cancer Res 2000; 60:3550-3558.
42. Esper PMoF, Chodak G., Sinner M, Cella D, and Pienta K J. Measuring quality of life in men with prostate cancer using the functional assessment of cancer therapy-prostate instrument. Urology 1997; 50:920-928.

43. Coons S J, Kaplan R M. Assessing health-related quality-of-life: application to drug therapy. Clin Ther 1992; 14:850-858.

TABLE 1

| Patient characteristics | |
|---|---|
| No. of patients | 11 |
| Age, year | |
| median | 71 |
| range | 57-75 |
| EOCG performance status, n | |
| 0 | 8 |
| 1 | 3 |
| HLA typing, n | |
| A24 | 4 |
| A2 | 7 |
| Serum PSA level, ng/ml | |
| median | 330 |
| range | 27-1072 |
| Serum ICTP level, ng/ml | |
| median | 6.2 |
| range | 3.0-15.3 |
| Site of metastases, n | |
| Bone only | 9 |
| Bone and nodal/organ | 1 |
| Nodal/organ | 1 |
| Prior use of estramustine phosphate, n | |
| Yes | 8 |
| No | 3 |

TABLE 2

Immune response during the combination therapy

| Case (Pts. No) | HLA type | Peptide | Sequence | (SEQ ID NO.) | Cellular response to peptide[a] during the combination therapy | | | | Anti-peptide IgG[b] during the combination therapy | | | | DTH Induction |
|---|---|---|---|---|---|---|---|---|---|---|---|---|---|
| | | | | | Pre | 6th | 12th | 18th | Pre | 6th | 12th | 18th | |
| 2 (010) | A-24 | lck$_{488-497}$ | DYLRSVLEDF | (11) | ArAB | — | AC | — | − | − | − | − | − |
| | | SART 2$_{93-101}$ | DYSARWNEI | (14) | C | — | — | — | − | − | − | − | − |
| | | SART 2$_{161-169}$ | AYDFLYNYL | (15) | A | — | AAC | ArArAA | − | − | − | − | + (20) |
| | | ART 1$_{170-179}$ | EYCLKFTKL | (1) | A | C | AAA | A | ++ | ++ | ++ | ++ | + (17) |
| | | lck$_{208-216}$ | HYTNASDGL | (8) | — | — | — | — | − | − | − | − | + (16) |
| | | SART 3$_{315-323}$ | AYIDFEMKI | (19) | — | — | Ar | ArArArB | − | − | − | − | − |
| 3 (014) | A-24 | SART 2$_{93-101}$ | DYSARWNEI | (14) | — | — | n.a. | n.a. | − | − | n.a. | n.a. | − |
| | | SART 3$_{109-118}$ | VYDYNCHVDL | (17) | ArAA | ArA | n.a. | n.a. | + | ++ | n.a. | n.a. | − |
| | | SART 3$_{315-323}$ | AYIDFEMKI | (19) | AC | A | n.a. | n.a. | + | + | n.a. | n.a. | − |
| | | CyB$_{91-99}$ | DFMIQGGDF | (2) | — | C | n.a. | n.a. | − | − | n.a. | n.a. | − |
| | | lck$_{208-216}$ | HYTNASDGL | (8) | A | — | n.a. | n.a. | − | − | n.a. | n.a. | − |
| | | lck$_{488-497}$ | DYLRSVLEDF | (11) | C | — | n.a. | n.a. | − | − | n.a. | n.a. | − |
| 4 (016) | A-24 | ART 1$_{170-179}$ | EYCLKFTKL | (1) | A | A | — | — | ++ | ++ | ++ | ++ | + (21) |
| | | lck$_{488-497}$ | DYLRSVLEDF | (11) | B | — | — | — | − | − | − | + | + (23) |
| | | SART 3$_{109-118}$ | VYDYNCHVDL | (17) | — | — | B | — | − | + | ++ | ++ | + (21) |
| | | SART 2$_{161-169}$ | AYDFLYNYL | (15) | — | Ar | B | — | − | − | − | − | − |
| 5 (019) | A-24 | SART 2$_{161-169}$ | AYDFLYNYL | (15) | A | — | — | ArA | − | − | − | − | + (8) |
| | | SART 2$_{899-907}$ | SYTRLFLIL | (16) | A | — | — | A | − | − | − | − | + (7) |
| | | SART 3$_{109-118}$ | VYDYNCHVDL | (17) | ArArArA | ArArArA | ArArArA | ArArAA | − | − | − | + | + (8) |
| | | lck$_{208-216}$ | HYTNASDGL | (8) | A | AA | — | — | − | − | − | + | + (5) |
| | | lck$_{488-497}$ | DYLRSVLEDF | (11) | — | ABB | — | — | − | + | + | + | + (6) |
| 7 (104) | A-2 | ppMAPkkk$_{432-440}$ | DLLSHAFFAI | (13) | — | C | — | n.a. | + | ++ | ++ | n.a. | + (32) |
| | | lck$_{246-254}$ | KLVERLGAA | (9) | — | — | B | n.a. | ++ | ++ | ++ | n.a. | + (31) |
| | | lck$_{422-430}$ | DVWSFGILL | (10) | A | AB | — | n.a. | − | + | + | n.a. | + (31) |
| | | UBE2V$_{43-51}$ | RLQEWCSVI | (20) | — | ACC | ArArArA | n.a. | ++ | ++ | ++ | n.a. | + (11) |
| | | HNRPL$_{140-148}$ | ALVEFEDVL | (6) | AAC | AC | ArArAA | n.a. | − | ++ | + | n.a. | − |
| | | HNRPL$_{501-510}$ | NVLHFFNAPL | (7) | — | AAA | ArArAc | n.a. | − | ++ | ++ | n.a. | − |
| 8 (108) | A-2 | lck$_{422-430}$ | DVWSFGILL | (10) | Ar | — | — | C | − | − | − | − | + (3) |
| | | ppMAPkkk$_{294-302}$ | GLLFLHTRTI | (12) | CC | — | — | — | − | + | + | + | + (2) |
| | | ppMAPkkk$_{432-440}$ | DLLSHAFFAI | (13) | ArA | A | — | — | − | − | + | + | + (3) |
| | | HNRPL$_{501-510}$ | NVLHFFNAPL | (7) | — | AB | E | ArA | − | − | − | + | + (17) |
| | | CypB$_{172-179}$ | VLEGMEVV | (4) | A | — | — | B | − | + | + | + | − |
| | | EIF4EBP1$_{51-59}$ | RIIYDRKFL | (5) | — | — | A | B | − | − | − | + | − |
| 9 (111) | A-2 | lck$_{422-430}$ | DVWSFGILL | (10) | C | — | n.a. | n.a. | − | − | n.a. | n.a. | + (5) |
| | | ppMAPkkk$_{294-302}$ | GLLFLHTRTI | (12) | A | — | n.a. | n.a. | − | − | n.a. | n.a. | + (5) |
| | | ppMAPkkk$_{432-440}$ | DLLSHAFFAI | (13) | A | — | n.a. | n.a. | − | − | n.a. | n.a. | + (6) |
| | | WHSC2$_{103-111}$ | ASLDSDPWV | (22) | CC | — | n.a. | n.a. | − | − | n.a. | n.a. | − |
| | | HNRPL$_{501-510}$ | NVLHFFNAPL | (7) | A | — | n.a. | n.a. | − | − | n.a. | n.a. | − |
| | | CypB$_{129-138}$ | KLKHYGPGWV | (3) | A | — | n.a. | n.a. | − | − | n.a. | n.a. | − |
| 10 (112) | A-2 | SART 3$_{309-317}$ | RLAEYQAYI | (18) | A | Ar | Ar | ArAC | − | − | − | + | − |
| | | CypB$_{172-179}$ | VLEGMEVV | (4) | A | — | — | A | − | + | + | + | − |
| | | lck$_{246-254}$ | KLVERLGAA | (9) | — | — | — | ArAAA | − | − | − | − | − |
| | | lck$_{422-430}$ | DVWSFGILL | (10) | — | C | — | ArAAA | − | + | + | − | − |
| | | ppMAPkkk$_{294-302}$ | GLLFLHTRTI | (12) | — | C | — | ArArAA | − | − | − | − | − |
| | | UBE2V$_{85-93}$ | LIADFLSGLI | (21) | — | — | A | AC | − | − | + | + | − |

TABLE 2-continued

Immune response during the combination therapy

| Case (Pts. No) | HLA type | Peptide | Sequence | (SEQ ID NO.) | Cellular response to peptide[a] during the combination therapy | | | | Anti-peptide IgG[b] during the combination therapy | | | | DTH In- duction |
|---|---|---|---|---|---|---|---|---|---|---|---|---|---|
| | | | | | Pre | 6th | 12th | 18th | Pre | 6th | 12th | 18th | |
| 11 (113) | A-2 | CypB$_{129-138}$ | KLKHYGPGWV | (3) | A | — | — | n.a. | − | − | − | n.a. | + (6) |
| | | lck$_{246-254}$ | KLVERLGAA | (9) | A | — | — | n.a. | − | ++ | ++ | n.a. | − |
| | | lck$_{422-430}$ | DVWSFGILL | (10) | A | A | C | n.a. | − | − | − | n.a. | − |
| | | ppMAPkkk$_{294-302}$ | GLLFLHTRTI | (12) | — | — | C | n.a. | + | ++ | ++ | n.a. | + (6) |
| | | UBE2V$_{43-51}$ | RLQEWCSVI | (20) | AAA | — | — | n.a. | − | ++ | ++ | n.a. | + (10) |
| 12 (115) | A-2 | CypB$_{129-138}$ | KLKHYGPGWV | (3) | — | A | — | n.a. | − | − | + | n.a. | − |
| | | lck$_{246-254}$ | KLVERLGAA | (9) | BB | A | B | n.a. | ++ | ++ | ++ | n.a. | − |
| | | WHSC2$_{141-}$ | ILGELREKV | (23) | AB | — | — | n.a. | − | − | − | n.a. | − |
| | | UBE2V$_{43-51}$ | RLQEWCSVI | (20) | AAAB | — | A | n.a. | − | ++ | ++ | n.a. | + (19) |
| | | HNRPL$_{501-510}$ | NVLHFFNAPL | (7) | ArAr | ArArArAr | ArArAr | n.a. | + | + | ++ | n.a. | + (19) |
| | | EIF4EBP1$_{51-59}$ | RIIYDRKFL | (5) | — | — | A | n.a. | + | ++ | ++ | n.a. | − |
| 13 (116) | A-2 | CypB$_{172-179}$ | VLEGMEVV | (4) | — | — | A | n.a. | + | + | + | n.a. | − |
| | | lck$_{246-254}$ | KLVERLGAA | (9) | ArC | AC | ArAA | n.a. | ++ | ++ | ++ | n.a. | − |
| | | lck$_{422-430}$ | DVWSFGILL | (10) | Ar | AAA | — | n.a. | + | − | − | n.a. | − |
| | | UBE2V$_{43-51}$ | RLQEWCSVI | (20) | ArA | AA | C | n.a. | + | + | ++ | n.a. | − |
| | | ppMAPkkk$_{432-440}$ | DLLSHAFFAI | (13) | — | A | — | n.a. | − | + | + | n.a. | + (17) |

[a]The CTL precusor assay was performed and each well was evaluated by the following criteria, and up to 4 peptides were administered;
Ar: p* ≦ 0.1 and 500 ≦ net**;
A: p ≦ 0.05 and 50 ≦ net;
B: p ≦ 0.05 and 25 ≦ net < 50;
C: 0.05 < p < 0.1 and 50 ≦ net.
*p value (Student's t test),
**specific IFN-γ production (pg/ml) was calculated by subtracting the response to HIV-derived irrelevent peptide.
AAAA: all four wells of quadruplicate assay were positive.
AAA: three wells of quadruplicate assay were positive.
AA: two wells of quadruplicate assay were positive.
A: one well of quadruplicate assay were positive.
[b]−: absent; +: present, low titer; ++: present, high titer.

TABLE 3

Best response of PSA, ICTP, bone scan and measurable disease during combination therapy

| Type of response (No. of evaluable pts.) | No. of pts. (%) |
|---|---|
| PSA response (n = 11) | |
| ≧50% decline | 8 (73) |
| <50% decline | 2 (18) |
| Total | 10 (91) |
| ICTP response (n = 10) | |
| ≧50% decline | 1 (10) |
| <50% decline | 8 (80) |
| Total | 9 (90) |
| Bone scan response (n = 10) | |
| ≧50% decline of % PABS | 0 |
| <50% decline of % PABS | 0 |
| Total | 0 |
| Measurable disease response (n = 2) | |
| ≧50% decline | 0 |
| <50% decline | 1 (50) |
| Total | 1 (50) |

TABLE 4

Adverse events of combination of patient-oriented vaccination and oral estramustine

| Toxicity | Grade[a] | | | | Total |
|---|---|---|---|---|---|
| | 1 | 2 | 3 | 4 | |
| Dermatologic | 10 | 3 | | | 13 |
| Bone pain | 3 | 4 | | | 7 |
| Hematuria | | 4 | | | 4 |
| Fatigue | 1 | 2 | | | 3 |
| Nausea | 2 | | | | 2 |
| Diarrhea | 2 | | | | 2 |
| Chest pain | 2 | | | | 2 |
| Edema | 2 | | | | 2 |
| arrhythmia | | | 1 | | 1 |
| Cerebral infarction | | | 1 | | 1 |
| Fever | 1 | | | | 1 |

[a]Toxicities base on the National Cancer Institute common toxicity scale. Some patients had more than 1 toxic reaction.

TABLE 5

Patient Characteristics

| | Vaccine alone | Vaccine plus estramustine phospha | Total |
|---|---|---|---|
| No. of patients | 3 | 13 | 16 |
| Age (year) | | | |
| Median | 69 | 69 | 69 |
| Range | 61-73 | 54-78 | 54-78 |

TABLE 5-continued

Patient Characteristics

| | Vaccine alone | Vaccine plus estramustine phospha | Total |
|---|---|---|---|
| Performance status[a] | | | |
| 0 | 1 | 12 | 13 |
| 1 | 2 | 1 | 3 |
| Serum PSA level (ng/ml) | | | |
| Median | 92.5 | 34.8 | 43.1 |
| Range | 25.1-2269.5 | 6.3-339.6 | 6.3-2269.5 |
| Gleason score (n) | | | |
| 7 | 0 | 6 | 6 |
| 8 | 1 | 3 | 4 |
| 9 | 2 | 4 | 6 |
| Site of metastases (n) | | | |
| Bone only | 2 | 7 | 9 |
| Bone and nodal/organ | 1 | 3 | 4 |
| Nodal/organ | 0 | 3 | 3 |
| Prior use of estramustine phosphate (n) | | | |
| Yes | 2 | 7 | 9 |
| No | 1 | 6 | 7 |

[a]Performance status by EOCG score.

TABLE 6

Immune response during the therapy

| Patients no. | Peptide | Cellular response to peptide[a] Pre | Cellular response to peptide[a] 6th | Anti-peptide IgG[b] Pre | Anti-peptide IgG[b] 6th | DTH induction | Therapy[c] | Best clinical responce | PR duration (M) | Follow up (M) | Prognosis |
|---|---|---|---|---|---|---|---|---|---|---|---|
| 1 | SART1 690 | 449 | 35 | − | − | − | combination | PR[d] | 6 | 17 | Alive |
|   | SART3 109 | 0 | 681.8 | + | + | +(3) | | | | | |
|   | PAP213 | 0 | 392.3* | + | + | − | | | | | |
|   | PSA248 | 19.5 | 100 | + | + | − | | | | | |
| 2 | SART2 93 | 22.8 | 376.8 | + | + | − | combination | PR | 3 | 10 | Death |
|   | SART3 109 | 14.3 | 25 | + | + | − | | | | | |
|   | PAP213 | 0 | 46.8 | + | ++ | − | | | | | |
|   | PSA248 | 28.3 | 505.8 | + | + | − | | | | | |
| 3 | SART3 109 | 26 | 27.3 | − | ++ | − | combination | — | — | 16 | Alive |
|   | SART3 315 | 47.8 | 39.3 | − | + | − | | | | | |
|   | lck208 | 34.8 | 0 | − | − | − | | | | | |
|   | PSA152 | 34.5 | 34.8 | − | − | − | | | | | |
| 4 | SART3 315 | 4 | 12.8 | + | + | − | combination | PR | 10 | 16 | Alive |
|   | PAP213 | 30.8 | 850* | + | + | − | | | | | |
|   | PSA248 | 12.8 | 303.5 | + | ++ | − | | | | | |
|   | PSM624 | 100 | 167 | + | + | − | | | | | |
| 5 | SART3 109 | 12.3 | 534** | + | + | +(5) | combination | — | — | 9 | Death |
|   | lck208 | 5.8 | 676 | + | − | +(5) | | | | | |
|   | lck488 | 29.8 | 99 | + | − | +(5) | | | | | |
|   | PSA248 | 14.3 | 149.8 | + | + | +(5) | | | | | |
| 6 | SART3 109 | 5.3 | 170.8 | + | + | − | vaccine | PR | 3 | 7 | Death |
|   | PAP213 | 5.8 | 0 | + | + | − | | | | | |
|   | PSA152 | 39.5 | 0 | + | − | − | | | | | |
|   | PSA248 | 6.5 | 0 | + | + | − | | | | | |
| 7 | SART2 93 | 125 | 162.5 | − | − | − | combination | PR | 5 | 12 | Death |
|   | SART3 109 | 5.5 | 750** | + | + | − | | | | | |
|   | PAP213 | 0 | 186.8** | − | + | +(6) | | | | | |
|   | PSA248 | 18.5 | 9.3 | + | + | − | | | | | |
| 8 | SART1 690 | 0 | 0 | + | + | − | combination | — | — | 15 | Alive |
|   | SART3 109 | 0 | 610.8* | + | + | − | | | | | |
|   | SART3 315 | 0 | 154** | − | − | − | | | | | |
|   | PSA248 | 0 | 0 | + | ++ | − | | | | | |
| 9 | SART1 690 | 250 | 81.8 | − | + | − | combination | — | — | 14 | Alive |
|   | PAP213 | 375 | 36.5 | − | − | − | | | | | |
|   | PSA152 | 250 | 18.8 | − | − | − | | | | | |
|   | PSA248 | 375 | 21.3 | − | ++ | − | | | | | |
| 10 | SART2 93 | 57.3 | 228.5** | + | − | − | combination | PR | 13 | 14 | Alive |
|   | lck488 | 36.5 | 26.8 | + | − | − | | | | | |
|   | PSA152 | 49.3 | 0 | + | + | − | | | | | |
|   | PSA248 | 17 | 0 | + | + | − | | | | | |
| 11 | SART3 109 | 625 | 250 | + | + | − | combination | — | — | 11 | Death |
|   | lck486 | 375 | 58.5 | − | + | − | | | | | |
|   | PAP213 | 250 | 153.5 | − | − | − | | | | | |
|   | PSA248 | 250 | 38.8 | − | ++ | − | | | | | |

TABLE 6-continued

Immune response during the therapy

| Patients no. | Peptide | Cellular response to peptide[a] Pre | Cellular response to peptide[a] 6th | Anti-peptide IgG[b] Pre | Anti-peptide IgG[b] 6th | DTH induction | Therapy[c] | Best clinical responce | PR duration (M) | Follow up (M) | Prognosis |
|---|---|---|---|---|---|---|---|---|---|---|---|
| 12 | SART3 109 | 35.8 | 496 | + | − | − | vaccine | — | — | 10 | Death |
|  | lck488 | 31.8 | 26.5 | + | − | − |  |  |  |  |  |
|  | PAP213 | 28.8 | 622.3* | + | + | − |  |  |  |  |  |
|  | PSA248 | 18 | 243.5 | + | + | − |  |  |  |  |  |
| 13 | SART3 315 | 112.3 | 26.5 | − | − | +(2) | combination | — | — | 5 | Death |
|  | PAP213 | 80 | 9.5 | − | − | +(2) |  |  |  |  |  |
|  | PSA152 | 168.8 | 15.5 | − | − | +(2) |  |  |  |  |  |
|  | PSA248 | 32.8 | 0 | + | + | +(2) |  |  |  |  |  |
| 14 | SART3 109 | 30.3 | 22.3 | + | + | − | combination | PR | 9 | 11 | Alive |
|  | SART3 315 | 44.8 | 255 | − | − | − |  |  |  |  |  |
|  | lck208 | 26.3 | 58.8 | − | − | − |  |  |  |  |  |
|  | PAP213 | 14.3 | 324.3** | − | − | − |  |  |  |  |  |
| 15 | SART2 161 | 0 | n.a. | + | n.a. | − | vaccine | — | — | 5 | Death |
|  | SART3 109 | 25.3 | n.a. | + | n.a. | − |  |  |  |  |  |
|  | SART3 315 | 15 | n.a. | + | n.a. | − |  |  |  |  |  |
|  | PSA248 | 0 | n.a. | + | n.a. | − |  |  |  |  |  |
| 16 | SART3 109 | 2.8 | 0 | + | n.a. | − | combination | — | — | 8 | Alive |
|  | lck488 | 30.5 | 19.8 | − | n.a. | − |  |  |  |  |  |
|  | PAP213 | 33.8 | 32 | + | n.a. | − |  |  |  |  |  |
|  | PSA248 | 23.8 | 9.8 | + | n.a. | − |  |  |  |  |  |

[a]The CTL precursor response to peptide was performed by quadriduplicate assay. Means of specific IFN-γ production (pg/ml) of pre- and post(6th)-vaccination PBMCs were calculated by subtracting the response to the HIV-derived irrelent peptide, and compared using Student's t-test. Increased IFN-γ production
*$p \leq 0.05$,
**$p \leq 0.10$.
[b]−: absent; +: present, low titer; ++: present, high titer.
[c]combination: vaccine plus estramustine phosphate; vaccine: vaccine only.
[d]PR: partial response.
[e]n.a.: not available.

TABLE 7

Adverse events

| Toxicity[a] | Vaccine alone G1 | G2 | G3 | G4 | Vaccine plus stramustine phosphat G1 | G2 | G3 | G4 | Total |
|---|---|---|---|---|---|---|---|---|---|
| Dermatologic | 3 |  |  |  | 12 | 1 |  |  | 16 |
| Anorexia | 1 |  |  |  | 6 |  |  |  | 7 |
| Bone pain |  |  |  |  | 1 | 5 |  |  | 6 |
| Hematuria |  | 1 |  |  | 1 |  |  |  | 2 |
| Edema |  |  |  |  | 2 |  |  |  | 2 |
| Cerebral infarction |  |  |  |  | 1 |  |  |  | 1 |
| anemia (Hb <8 mg/dl) |  | 1 |  |  |  |  |  |  | 1 |
| Fatigue | 1 |  |  |  |  |  |  |  | 1 |

[a]Toxicities based on the National Cancer Institute common toxicity scale (Version 2). Some patients had more than one toxic reaction.

TABLE 8

| Dose of Estramustine | Case | Cellular Immunity | Humoral Immunity | Dudration of Administration | Clinical Response |
|---|---|---|---|---|---|
| 560 mg/day | 5 | 0/3 | 1/2 | 1 M × 3, 6 M × 2 | 5PD |
| 280 mg/day | 32 | 23/31 | 27/32 | 9 M(Median) | 10PR, 10SD, 12PD |
| 140 mg/day | 4 | 3/4 | 4/4 | 2 M, 3 M, 8 M, 9 M | 1SD, 3PD |

TABLE 9

| Case No. | Clinical Response by Vaccination Alone | Clinical Response by Combination | Overall Survival |
|---|---|---|---|
| 1 | PD | PR | 29 M |
| 2 | PD | PR | 25 M |
| 3 | PD | PR | 42 M+ |
| 4 | PD | PR | 26 M |
| 5 | PD | PR | 29 M+ |
| 6 | PD | PR | 14 M |
| 7 | PD | PR | 15 M+ |
| 8 | PD | SD | 34 M+ |
| 9 | PD | SD | 32 M+ |
| 10 | PD | SD | 15 M |
| 11 | PD | SD | 25 M+ |
| 12 | PD | SD | 23 M+ |
| 13 | PD | PD | 24 M |
| 14 | PD | PD | 12 M |

What is claimed is:

1. A method for treating a prostate cancer, which comprises administering
    i) a therapeutically effective amount of a cancer antigen peptide that binds to HLA class I antigen and has an ability to induce Cytotoxic T Lymphocytes specific to the peptide in a patient in need thereof and
    ii) an amount in the range of 140 to 560 mg/day of estramustine or a salt thereof to the patient in need thereof.

2. The method of claim 1, wherein the cancer is a hormone-refractory prostate cancer.

3. The method of claim 1, wherein the patient does not respond to a therapeutically effective amount of estramustine or a salt thereof when administered without administering a cancer antigen peptide.

4. The method of claim 1, wherein the patient does not respond to a therapeutically effective amount of a cancer antigen peptide when administered without administering estramustine or a salt thereof.

* * * * *

SEQUENCE LISTING

<160> NUMBER OF SEQ ID NOS: 32

<210> SEQ ID NO 1
<211> LENGTH: 9
<212> TYPE: PRT
<213> ORGANISM: Artificial
<220> FEATURE:
<223> OTHER INFORMATION: Synthetic Construct

<400> SEQUENCE: 1

Glu Tyr Cys Leu Lys Phe Thr Lys Leu
1               5

<210> SEQ ID NO 2
<211> LENGTH: 9
<212> TYPE: PRT
<213> ORGANISM: Artificial
<220> FEATURE:
<223> OTHER INFORMATION: Synthetic Construct

<400> SEQUENCE: 2

Asp Phe Met Ile Gln Gly Gly Asp Phe
1               5

<210> SEQ ID NO 3
<211> LENGTH: 10
<212> TYPE: PRT
<213> ORGANISM: Artificial
<220> FEATURE:
<223> OTHER INFORMATION: Synthetic Construct

<400> SEQUENCE: 3

Lys Leu Lys His Tyr Gly Pro Gly Trp Val
1               5                   10

<210> SEQ ID NO 4
<211> LENGTH: 8
<212> TYPE: PRT
<213> ORGANISM: Artificial
<220> FEATURE:
<223> OTHER INFORMATION: Synthetic Construct

<400> SEQUENCE: 4

Val Leu Glu Gly Met Glu Val Val
1               5

<210> SEQ ID NO 5
<211> LENGTH: 9
<212> TYPE: PRT
<213> ORGANISM: Artificial
<220> FEATURE:
<223> OTHER INFORMATION: Synthetic Construct

<400> SEQUENCE: 5

Arg Ile Ile Tyr Asp Arg Lys Phe Leu
1               5

<210> SEQ ID NO 6
<211> LENGTH: 9
<212> TYPE: PRT
<213> ORGANISM: Artificial
<220> FEATURE:
<223> OTHER INFORMATION: Synthetic Construct

<400> SEQUENCE: 6

```
Ala Leu Val Glu Phe Glu Asp Val Leu
1               5
```

<210> SEQ ID NO 7
<211> LENGTH: 10
<212> TYPE: PRT
<213> ORGANISM: Artificial
<220> FEATURE:
<223> OTHER INFORMATION: Synthetic Construct

<400> SEQUENCE: 7

```
Asn Val Leu His Phe Phe Asn Ala Pro Leu
1               5                   10
```

<210> SEQ ID NO 8
<211> LENGTH: 9
<212> TYPE: PRT
<213> ORGANISM: Artificial
<220> FEATURE:
<223> OTHER INFORMATION: Synthetic Construct

<400> SEQUENCE: 8

```
His Tyr Thr Asn Ala Ser Asp Gly Leu
1               5
```

<210> SEQ ID NO 9
<211> LENGTH: 9
<212> TYPE: PRT
<213> ORGANISM: Artificial
<220> FEATURE:
<223> OTHER INFORMATION: Synthetic Construct

<400> SEQUENCE: 9

```
Lys Leu Val Glu Arg Leu Gly Ala Ala
1               5
```

<210> SEQ ID NO 10
<211> LENGTH: 9
<212> TYPE: PRT
<213> ORGANISM: Artificial
<220> FEATURE:
<223> OTHER INFORMATION: Synthetic Construct

<400> SEQUENCE: 10

```
Asp Val Trp Ser Phe Gly Ile Leu Leu
1               5
```

<210> SEQ ID NO 11
<211> LENGTH: 10
<212> TYPE: PRT
<213> ORGANISM: Artificial
<220> FEATURE:
<223> OTHER INFORMATION: Synthetic Construct

<400> SEQUENCE: 11

```
Asp Tyr Leu Arg Ser Val Leu Glu Asp Phe
1               5                   10
```

<210> SEQ ID NO 12
<211> LENGTH: 10
<212> TYPE: PRT
<213> ORGANISM: Artificial
<220> FEATURE:
<223> OTHER INFORMATION: Synthetic Construct

<400> SEQUENCE: 12

```
Gly Leu Leu Phe Leu His Thr Arg Thr Ile
```

```
1               5                  10
```

<210> SEQ ID NO 13
<211> LENGTH: 10
<212> TYPE: PRT
<213> ORGANISM: Artificial
<220> FEATURE:
<223> OTHER INFORMATION: Synthetic Construct

<400> SEQUENCE: 13

```
Asp Leu Leu Ser His Ala Phe Phe Ala Ile
1               5                  10
```

<210> SEQ ID NO 14
<211> LENGTH: 9
<212> TYPE: PRT
<213> ORGANISM: Artificial
<220> FEATURE:
<223> OTHER INFORMATION: Synthetic Construct

<400> SEQUENCE: 14

```
Asp Tyr Ser Ala Arg Trp Asn Glu Ile
1               5
```

<210> SEQ ID NO 15
<211> LENGTH: 9
<212> TYPE: PRT
<213> ORGANISM: Artificial
<220> FEATURE:
<223> OTHER INFORMATION: Synthetic Construct

<400> SEQUENCE: 15

```
Ala Tyr Asp Phe Leu Tyr Asn Tyr Leu
1               5
```

<210> SEQ ID NO 16
<211> LENGTH: 9
<212> TYPE: PRT
<213> ORGANISM: Artificial
<220> FEATURE:
<223> OTHER INFORMATION: Synthetic Construct

<400> SEQUENCE: 16

```
Ser Tyr Thr Arg Leu Phe Leu Ile Leu
1               5
```

<210> SEQ ID NO 17
<211> LENGTH: 10
<212> TYPE: PRT
<213> ORGANISM: Artificial
<220> FEATURE:
<223> OTHER INFORMATION: Synthetic Construct

<400> SEQUENCE: 17

```
Val Tyr Asp Tyr Asn Cys His Val Asp Leu
1               5                  10
```

<210> SEQ ID NO 18
<211> LENGTH: 9
<212> TYPE: PRT
<213> ORGANISM: Artificial
<220> FEATURE:
<223> OTHER INFORMATION: Synthetic Construct

<400> SEQUENCE: 18

```
Arg Leu Ala Glu Tyr Gln Ala Tyr Ile
1               5
```

```
<210> SEQ ID NO 19
<211> LENGTH: 9
<212> TYPE: PRT
<213> ORGANISM: Artificial
<220> FEATURE:
<223> OTHER INFORMATION: Synthetic Construct

<400> SEQUENCE: 19

Ala Tyr Ile Asp Phe Glu Met Lys Ile
1               5

<210> SEQ ID NO 20
<211> LENGTH: 9
<212> TYPE: PRT
<213> ORGANISM: Artificial
<220> FEATURE:
<223> OTHER INFORMATION: Synthetic Construct

<400> SEQUENCE: 20

Arg Leu Gln Glu Trp Cys Ser Val Ile
1               5

<210> SEQ ID NO 21
<211> LENGTH: 10
<212> TYPE: PRT
<213> ORGANISM: Artificial
<220> FEATURE:
<223> OTHER INFORMATION: Synthetic Construct

<400> SEQUENCE: 21

Leu Ile Ala Asp Phe Leu Ser Gly Leu Ile
1               5                   10

<210> SEQ ID NO 22
<211> LENGTH: 9
<212> TYPE: PRT
<213> ORGANISM: Artificial
<220> FEATURE:
<223> OTHER INFORMATION: Synthetic Construct

<400> SEQUENCE: 22

Ala Ser Leu Asp Ser Asp Pro Trp Val
1               5

<210> SEQ ID NO 23
<211> LENGTH: 9
<212> TYPE: PRT
<213> ORGANISM: Artificial
<220> FEATURE:
<223> OTHER INFORMATION: Synthetic Construct

<400> SEQUENCE: 23

Ile Leu Gly Glu Leu Arg Glu Lys Val
1               5

<210> SEQ ID NO 24
<211> LENGTH: 9
<212> TYPE: PRT
<213> ORGANISM: Artificial
<220> FEATURE:
<223> OTHER INFORMATION: Synthetic Construct

<400> SEQUENCE: 24

Thr Phe Asp Tyr Leu Arg Ser Val Leu
1               5
```

```
<210> SEQ ID NO 25
<211> LENGTH: 10
<212> TYPE: PRT
<213> ORGANISM: Artificial
<220> FEATURE:
<223> OTHER INFORMATION: Synthetic Construct

<400> SEQUENCE: 25

Arg Tyr Leu Thr Gln Glu Thr Asn Lys Val
1               5                   10

<210> SEQ ID NO 26
<211> LENGTH: 9
<212> TYPE: PRT
<213> ORGANISM: Artificial
<220> FEATURE:
<223> OTHER INFORMATION: Synthetic Construct

<400> SEQUENCE: 26

Leu Tyr Ala Trp Glu Pro Ser Phe Leu
1               5

<210> SEQ ID NO 27
<211> LENGTH: 9
<212> TYPE: PRT
<213> ORGANISM: Artificial
<220> FEATURE:
<223> OTHER INFORMATION: Synthetic Construct

<400> SEQUENCE: 27

Leu Tyr Cys Glu Ser Val His Asn Phe
1               5

<210> SEQ ID NO 28
<211> LENGTH: 9
<212> TYPE: PRT
<213> ORGANISM: Artificial
<220> FEATURE:
<223> OTHER INFORMATION: Synthetic Construct

<400> SEQUENCE: 28

Cys Tyr Ala Ser Gly Trp Gly Ser Ile
1               5

<210> SEQ ID NO 29
<211> LENGTH: 10
<212> TYPE: PRT
<213> ORGANISM: Artificial
<220> FEATURE:
<223> OTHER INFORMATION: Synthetic Construct

<400> SEQUENCE: 29

His Tyr Arg Lys Trp Ile Lys Asp Thr Ile
1               5                   10

<210> SEQ ID NO 30
<211> LENGTH: 9
<212> TYPE: PRT
<213> ORGANISM: Artificial
<220> FEATURE:
<223> OTHER INFORMATION: Synthetic Construct

<400> SEQUENCE: 30

Thr Tyr Ser Val Ser Phe Asp Ser Leu
1               5
```

```
<210> SEQ ID NO 31
<211> LENGTH: 9
<212> TYPE: PRT
<213> ORGANISM: Artificial
<220> FEATURE:
<223> OTHER INFORMATION: Synthetic Construct

<400> SEQUENCE: 31

Glu Tyr Arg Gly Phe Thr Gln Asp Phe
1               5

<210> SEQ ID NO 32
<211> LENGTH: 10
<212> TYPE: PRT
<213> ORGANISM: Artificial
<220> FEATURE:
<223> OTHER INFORMATION: Synthetic Construct

<400> SEQUENCE: 32

Arg Tyr Leu Arg Gln Gln Leu Leu Gly Ile
1               5                   10
```